(12) United States Patent
Bouzide et al.

(10) Patent No.: US 6,455,587 B1
(45) Date of Patent: Sep. 24, 2002

(54) AMINO ACID DERIVATIVES AS HIV ASPARTYL PROTEASE INHIBITORS

(75) Inventors: Abderrahim Bouzide; Gilles Sauvé, both of Laval; Brent Richard Stranix, Pointe-Claire; Guy Sévigny, Montreal; Jocelyn Yelle, Laval, all of (CA)

(73) Assignee: Pharmacor Inc., Laval (CA)

( * ) Notice: Subject to any disclaimer, the term of this patent is extended or adjusted under 35 U.S.C. 154(b) by 0 days.

(21) Appl. No.: 09/526,209

(22) Filed: Mar. 15, 2000

(51) Int. Cl.⁷ .................. A61K 31/18; C07C 317/00; C07C 315/00
(52) U.S. Cl. .................. 514/602; 514/603; 560/13; 562/430
(58) Field of Search .................. 562/430; 514/602, 514/604; 560/604, 13

(56) References Cited

FOREIGN PATENT DOCUMENTS

| WO | 9206998 | * | 4/1992 |
| WO | WO 95/06998 | | 4/1992 |
| WO | WO 95/24385 | | 9/1995 |
| WO | WO 98/31664 | | 7/1998 |
| WO | WO 99/55687 | | 4/1999 |

OTHER PUBLICATIONS

Chemical Abstracts, vol. 123, No. 7, H. Setsuo: "Preparation of lankacidin derivatives as antibacterials" . . . XP002182864.
Chemical Abstracts, vol. 46, No. 13.N.Izumiya: N . . . Benzoyl . . . XP002182717.
Chemical Abstracts, vol. 46, No. 13.N.Izumiya: N . . . Benzoyl . . . XP002182718.
Chemical Abstracts, vol. 46, No. 13.N.Izumiya: "The walden inverson of amino acids" . . . XP002182719.
Journal of labelled compounds and radiopharmaceuticals, pp. 605–609 T. G. Hamill et al. XP000926587.
Collection Czechoslovak Chem. Commun. vol. 53 "An alternative route" pp 2473–2494 . . . XP001002995.
Polish journal of chemistry A.El–Naggar pp. 637–642 . . . XP000926586.
Acta Pharm. Jugosl.33, A.El–Naggar pp. 103–110 . . . XP000926585.
Chem. Pharm Bull. No. 5, vol. 33 M. Maeda pp. 2137–2141 XP001010687.
Journal of peptide research, Amino acids derived from . . . pp. 183–189 XP000679594.
Int. J.Peptide Protein res. 32, G. Karup pp. 331–343 XP000926584.
Chemical works of Gedeon Richter Ltd. I. Schon pp. 303–305 XP002182716.
Biorganic & Medicinal Chemistry Letters vol. 7, Beta–Amino Acid derivatives . . . pp. 727–732.
Canadian Journal of Chemistry, 46 J. Leclerc "On the selectivity of acylation of unprotected diamino acids" pp. 1047–1057 XP000926722.
Biochem J. 102 pp. 728–734 Kinetics and mechanism . . . D. T. Elmore XP002182865.
Takeda Chemical Industries Ltd. "Preparation of lankacidin derivatives as antibacterials" pp. 1–3 XP002182866.
Physiol. Chem. Phys. Med. The oxidative deamination of . . . p. 1 XP002182868.
Collect. Czech. Chem. Commun. "Amino acids and peptides" Ceskoslov A. p. 1 XP002182867.

* cited by examiner

Primary Examiner—Richard L. Raymond
Assistant Examiner—Subdaker B. Patel
(74) Attorney, Agent, or Firm—Ronald S. Kosie; Robert Brouillette

(57) ABSTRACT

The present invention relates to a class of amino acid derivatives with HIV aspartyl protease inhibitory properties.

27 Claims, No Drawings

AMINO ACID DERIVATIVES AS HIV ASPARTYL PROTEASE INHIBITORS

TECHNICAL FIELD OF THE INVENTION

The present invention relates to a novel class of compounds with aspartyl protease inhibitory properties. This invention in particular relates to a class of amino acid derivatives with HIV aspartyl protease inhibitory properties that have been characterized by specific structural and physicochemical characteristics. In addition, this invention relates to different pharmaceutical compositions comprising these compounds. The compounds and the pharmaceutical compositions of this invention have been demonstrated to inhibit the activity of HIV aspartyl protease. Accordingly, this inhibitory property may be advantageously used to provide compounds with antiviral properties against HIV viruses, including the HIV-1 and HIV-2 viruses.

BACKGROUND OF THE INVENTION

The HIV (human immunodeficiency virus) retrovirus is the causative agent for AIDS (acquired immunodeficiency syndrome). Thus the HIV-1 retrovirus primarily uses the CD4 receptor (a 58 kDa transmembrane protein) to gain entry into susceptible cells, through high-affinity interactions between the viral envelope glycoprotein (gp 120) and a specific region of the CD4 molecule found in CD4 (+) T-helper lymphocytes and other cells carrying the receptor (Lasky L. A. et al., Cell vol. 50, p. 975–985 (1987)). HIV infection is characterized by a period immediately following infection called "asymptomatic" which is devoid of clinical manifestations in the patient. Progressive HIV-induced destruction of the immune system then leads to increased susceptibility to opportunistic infections, which eventually produces a syndrom called AIDS-related complex (ARC) characterized by symptoms such as persistent generalized lymphadenopathy, fever, weight loss, followed itself by full blown AIDS.

After entry of the retrovirus into a cell, viral RNA is converted into DNA, which is then integrated into the host cell DNA. The reverse transcriptase encoded by the viral genome catalyzes the first of these reactions (Haseltine W. A. FASEB J. Vol. 5 2349–2360 (1991)). At least three functions have been attributed to reverse transcriptase: RNA-dependent DNA polymerase activity which catalyzes the synthesis of the minus strand DNA from viral RNA, ribonuclease H (RNase H) activity which cleaves the RNA template from RNA-DNA hybrids, and DNA-dependent DNA polymerase activity which catalyzes the synthesis of a second DNA strand from the minus strand DNA template (Goff S. P. J. Acq. Imm. Defic. Syndr., vol. 3 p. 817–831 (1990)). The double stranded DNA produced by reverse transcriptase, now called provirus, is then able to be inserted into host genomic DNA.

At the end of reverse transcription, the viral genome now in the form of DNA is integrated into host genomic DNA and serves as a template for viral gene expression by the host transcription system, which leads eventually to the production of new viral particles (Sakai, H al., J. Virol. Vol. 67, p. 1169–1174 (1993)). The preintegration complex consists of integrase, reverse transcriptase, p17 and proviral DNA (Bukrinsky et al., Proc. Nat. Acad. Sci. USA vol. 89, p. 6580–6584 (1992)). The phosphorylated p17 protein plays a key role in targeting the preintegration complex into the nucleus of the host cell (Gallay et al., Cell, vol. 80, p. 379–388 (1995)), a necessary step for integration to take place.

The primary RNA transcripts made from the provirus are synthesized by the host cell RNA polymerase II whose activity is modulated by two virus-encoded proteins called Tat and Rev. The viral proteins are formed as polyproteins. Post-translational modifications of viral polyproteins include processing and glycosylation of Env (envelope) proteins, and myristylation of the N-terminal residue of the p17 protein in the Gag and Gag-Pol polyproteins. The Gag and Gag-Pol precursors will give rise after cleavage to structural proteins and viral enzymes. The viral protease is the enzyme responsible for the cleavage of polyproteins Gag and Gag-Pol into mature proteins, a step essential for virus infectivity.

A number of synthetic antiviral agents have been designed to block various stages in the replication cycle of HIV. These agents include compounds which interfere with viral binding to CD4 T-lymphocytes (for example, soluble CD4), compounds which block viral reverse transcriptase (for example, didanosine and zidovudine (AZT)), budding of virion from the cell (interferon), or the viral protease (for example Ritonavir and Indinavir). Some of these agents proved ineffective in clinical tests. Others, targeting primarily early stages of viral replication, have no effect on the production of infectious virions in chronically infected cells. Furthermore, administration of many of these agents in effective therapeutic doses has led to cell-toxicity and unwanted side effects, such as anemia, neurotoxicity and bone marrow suppression.

Anti-protease compounds represent the most recent drugs developed to block HIV replication. These compounds inhibit the formation of infectious virions by interfering with the processing of viral polyprotein precursors. Thus, the antiviral potential of HIV protease inhibition has been demonstrated using peptidic inhibitors. Such peptidic compounds, however, are typically large and complex molecules that tend to exhibit poor bioavailability and are not generally consistent with oral administration. Accordingly, the need exists for compounds that can effectively inhibit the action of viral proteases, for use as agents for preventing and treating chronic and acute viral infections, such as HIV. The problem of viral resistance also underlines the need for new drugs to fight HIV infections.

It would be advantageous to have a class of derivatives that are aspartyl protease inhibitors, and particularly, HIV aspartyl protease inhibitors.

SUMMARY OF THE INVENTION

The present invention relates to a class amino acid derivatives as well as their pharmaceutically acceptable derivatives (e.g. salts).

Accordingly, the present invention in accordance with one aspect thereof provides a compound of formula I

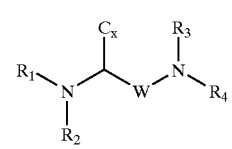

(as well as pharmaceutically acceptable derivatives thereof) and when the compound of formula I comprises an amino group pharmaceutically acceptable ammonium salts thereof, wherein W is selected from the group consisting of
—$(CH_2)_n$—, and —$CH_2$—XX—$CH_2$—$CH_2$—
wherein n is 1, 2, 3, 4 or 5, wherein XX is selected from the group consisting of O, $NR_5$, S, SO and $SO_2$ wherein Cx is selected from the group consisting of —COOM, —$COOR_5$, —$CH_2OH$, —$CONR_5R_6$, —CONHOH, 9-fluorenylmethoxycarbonyl-lysyl-NH—CO, benzyloxycarbonyl, and tetrazolyl, wherein M is an alkali metal (e.g. Na, K, Cs, etc.) or an alkaline earth metal, wherein $R_1$ and $R_3$, the same or different, are selected (i.e. independently) from the group consisting of H, tert-butoxycarbonyl, a straight or branched alkyl group of 1 to 6 carbon atoms, a cycloalkylalkyl group having 3 to 7 carbon atoms in the cycloalkyl part thereof and 1 to 3 carbon atoms in the alkyl part thereof (e.g. cyclopropylmethyl, cyclopentylmethyl, cyclohexylmethyl, cycloheptylmethyl, etc.) an aryalkyl group of formula (2)

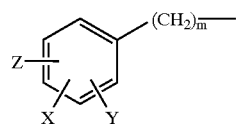

(2)

and a heterocycle-alkyl group of formula heterocycle-$(CH_2)_m$—wherein $R_2$ and $R_4$ the same or different are selected (i.e. independently) from the group consisting of H, CHO—, $CF_3$—, $CH_3CO$—, benzoyl, 9-fluorenylmethoxycarbonyl, tert-butoxycarbonyl, benzyloxycarbonyl, 2-chlorobenzyloxycarbonyl, 4-OH-7-$CF_3$-quinoline-3-CO—, 3-indole-$CH_2CH_2CO$—, 3-indole-$CH_2CO$—, 3-indole-CO—, 2-indole-CO—, $C_6H_5OCH_2CO$—, $(C_6H_5)_2COHCO$—, $C_6H_5SCH_2CO$—, $C_6H_5CH_2CH_2CS$—, cholesteryl-OCO—, 2-quinoline-CO—, xanthene-9-CO—, 4-$C_6H_5CH_2CH_2CONHC_6H_4SO_2$—, 2-$NO_2C_6H_4CHCHCO$—, 3-$C_5H_4NCHCHCO$—, 3-$C_5H_4NCH_2CH_2CO$—, fluorene-$CH_2CO$—, camphor-10-$CH_2$—$SO_2$—, $(C_6H_5)_2CH$—CO—, fluorene-CO—, 1-naphthyl-$SO_2$—, 2-naphthyl-$SO_2$—, fluorenyl-$SO_2$—, phenanthryl-$SO_2$—, anthracenyl-$SO_2$—, quinoline-$SO_2$—, 4-$CH_3COONHC_6H_4$—$SO_2$—, $C_6H_5CHCH$—$SO_2$—, 4-$NO_2C_6H_4$—$SO_2$—, an aryalkyl group of formula (2) as defined above, a sulfonyl group of formula (3)

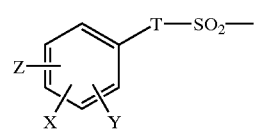

(3)

a heterocycle-alkylsulfonyl group of formula heterocycle-$(CH_2)_m$—$SO_2$— and
a carbonyl group of formula (4)

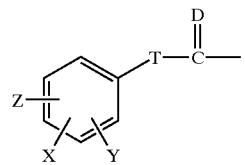

(4)

wherein T is selected from the group consisting of —$(CH_2)_{mm}$—, —CH=CH— and —$CH_2$—CH=CH— wherein D is selected from the group consisting of O, $NR_7$ and S,
wherein m is 1, 2, 3 or 4,
wherein mm is 0, 1, 2, 3 or 4
wherein X, Y and Z, the same or different, are selected (i.e. independently) from the group consisting of H, a straight or branched alkyl group of 1 to 6 carbon atoms, F, Cl, Br, I, —$CF_3$, —$NO_2$, —$NH_2$, —$NHR_5$, —$NR_5R_6$, —$NHCOR_5$, —NHCOheterocycle, heterocycle being as defined above, —$OR_5$, —$SR_5$, —$SOR_5$, —$SO_2R_5$, —$COOR_5$, —$CH_2OH$, —$COR_5$, and —NHCOAryl, Aryl being an unsubstituted phenyl group or a phenyl group substituted by one or more members of the group consisting of a straight or branched alkyl group of 1 to 6 carbon atoms, F, Cl, Br, I, —$CF_3$, —$NO_2$, —$NH_2$—$NHR_5$, —$NR_5R_6$, —$NHCOR_5$, —$OR_5$, —$SR_5$, —$SOR_5$, —$SO_2R_5$, —$COOR_5$, —$CH_2OH$, —$COR_5$,
wherein $R_5$ and $R_6$, are independently selected from the group consisting of H, and a straight or branched alkyl group of 1 to 6 carbon atoms
wherein $R_7$ is selected from the group consisting of HO—, $CH_3O$—, NC—, benzyloxy, and $H_2N$— and
wherein heterocycle is selected from the group consisting of heterocyclic groups comprising 5 to 7 ring atoms, said ring atoms comprising carbon atoms and from one to four heteroatoms selected from the group consisting of nitrogen, oxygen and sulfur, said heterocyclic groups being monocyclic, bicyclic or monocyclic fused with one or two benzene rings.

The present invention in particular relates to a compound of formula I as defined herein pharmaceutically acceptable derivatives thereof and where applicable or appropriate pharmaceutically acceptable salts thereof, wherein W is —$(CH_2)_n$—, n is 3 or 4 and D is O. In accordance with the present invention $R_2$ may in particular be a sulfonyl group of formula (3) as defined herein.

The present invention in particular provides a compound of formula Ia

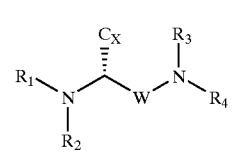

Ia (as well as pharmaceutically acceptable derivatives thereof) and when the compound of formula Ia comprises an amino group pharmaceutically acceptable ammonium salts thereof, wherein W, $C_x$, $R_1$, $R_2$, $R_3$ and $R_4$ are as defined herein.

The present invention more particularly provides a compound of formula Ib

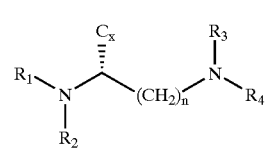

Ib (as well as pharmaceutically acceptable derivatives thereof) and when the compound of formula Ib comprises an amino group pharmaceutically acceptable ammonium salts thereof, wherein $C_x$, n, $R_1$, $R_2$, $R_3$ and $R_4$ are as defined herein.

The present invention particularly relates to a compound of formula I, Ia or Ib as defined herein (as well as pharmaceutically acceptable derivatives thereof) and where applicable or appropriate pharmaceutically acceptable ammonium salts thereof, wherein Cx is selected from the group consisting of —COOM, —COOR$_5$, —CH$_2$OH, —CONHOH, and benzyloxycarbonyl, wherein M is an alkali metal (e.g. Na, K, Cs, etc.) and R$_5$ is as defined herein, wherein R$_1$ and R$_3$, the same or different, are selected (i.e. independently) from the group consisting of H, a straight or branched alkyl group of 1 to 6 carbon atoms, a cycloalkylalkyl group having 3 to 7 carbon atoms in the cycloalkyl part thereof and 1 to 3 carbon atoms in the alkyl part thereof and an arylalkyl group of formula (2) as defined herein wherein Z and Y are each H, m is 1 and X is H, Br or F wherein R$_2$ and R$_4$ the same or different are selected (i.e. independently) from the group consisting of H, 9-fluorenylmethoxycarbonyl, benzyloxycarbonyl, 2-chlorobenzyloxycarbonyl, 4-OH-7-CF$_3$-quinoline-3-CO—, 3-indole-CH$_2$CH$_2$CO—, 3-indole-CH$_2$CO—, 3-indole-CO—, 2-indole-CO—, C$_6$H$_5$CHCHCO—, C$_6$H$_5$CH$_2$CH$_2$CO—, C$_6$H$_5$CH$_2$CH$_2$CH$_2$CO—, C$_6$H$_5$CH$_2$CHCHCO—, C$_6$H$_5$OCH$_2$CO—, (C$_6$H$_5$)$_2$COHCO—, C$_6$H$_5$SCH$_2$CO—, C$_6$H$_5$CH$_2$CH$_2$CS—, 4-HOC$_6$H$_4$CH$_2$CH$_2$CO—, cholesteryl-OCO—, 2-quinoline-CO—, fluorene-CO—, xanthene-9-CO—, 4-C$_6$H$_5$CH$_2$CH$_2$CONHC$_6$H$_4$SO$_2$—, 4-NO$_2$C$_6$H$_4$CHCHCO—, 3-NO$_2$C$_6$H$_4$CHCHCO—, 2-NO$_2$C$_6$H$_4$CHCHCO—, 2,3-(CH$_3$O)$_2$C$_6$H$_3$CHCHCO—, 3,4-(CH$_3$O)$_2$C$_6$H$_3$CHCHCO—, 2,5-(CH$_3$O)$_2$C$_6$H$_3$CHCHCO—, 2,5-(CH$_3$O)$_2$C$_6$H$_3$CH$_2$CH$_2$CO—, 3,5-(CH$_3$O)$_2$C$_6$H$_3$CH$_2$CH$_2$CO—, 3,4-(CH$_3$O)$_2$C$_6$H$_3$CH$_2$CH$_2$CO—, 2,4-(CH$_3$O)$_2$C$_6$H$_3$CHCHCO—, 2,4-(CH$_3$O)$_2$C$_6$H$_3$CH$_2$CH$_2$CO—, 3,4-(CH$_3$O)$_2$C$_6$H$_3$CHCHCO—, 2,3-(CH$_3$O)$_2$C$_6$H$_3$CH$_2$CH$_2$CO—, 4-CH$_3$OC$_6$H$_4$CHCHCO—, 4-CH$_3$OC$_6$H$_4$CH$_2$CH$_2$CO—, 2-CH$_3$OC$_6$H$_4$CHCHCO—, 3-CH$_3$OC$_6$H$_4$CHCHCO—, 3-CH$_3$OC$_6$H$_4$CH$_2$CH$_2$CO—, 2-CH$_3$OC$_6$H$_4$CH$_2$CO—, 4-CH$_3$C$_6$H$_4$CHCHCO—, 4-HOC$_6$H$_4$CHCHCO—, 3-NH$_2$C$_6$H$_4$CH$_2$CH$_2$CO—, 3-C$_5$H$_4$NCHCHCO—, 3-C$_5$H$_4$NCH$_2$CH$_2$CO—, fluorene-CH$_2$CO—, camphor-10-CH$_2$—SO$_2$—, (C$_6$H$_5$)$_2$CH—CO—, 1-naphthyl-SO$_2$—, 2-naphthyl-SO$_2$—, fluorenyl-SO$_2$—, phenanthryl-SO$_2$—, anthracenyl-SO$_2$—, quinoline-SO$_2$—, 4-CH$_3$COONHC$_6$H$_4$—SO$_2$—, C$_6$H$_5$CHCH—SO$_2$—, 4-NO$_2$C$_6$H$_4$—SO$_2$—, and a sulfonyl group of formula (3) as defined herein wherein T is —(CH$_2$)$_{mm}$— wherein mm is 0 and wherein X, Y and Z, are independently selected from the group consisting of H, a straight or branched alkyl group of 1 to 6 carbon atoms, F, Cl, Br, I, —CF$_3$, —NO$_2$, —NH$_2$, and —COR$_5$ , wherein R$_5$ is as defined herein The present invention particularly provides a compound of formula I, Ia or Ib as defined herein (as well as pharmaceutically acceptable derivatives thereof) and when applicable or appropriate pharmaceutically acceptable ammonium salts thereof, wherein R$_1$ is selected from the group consisting of isobutyl, cyclopropylmethyl and benzyl, wherein R$_2$ is a sulfonyl group of formula (3) as defined above, wherein R$_3$ is H and wherein Cx is selected from the group consisting of COOM, and COOR$_5$, M being an alkali metal (e.g. Na, K Cs, etc.) and R$_5$ being as defined herein.

The present invention for example provides a compound of formula Ib as defined herein pharmaceutically acceptable derivatives thereof and where applicable or appropriate pharmaceutically acceptable salts thereof, wherein n is 4, wherein R$_1$ is selected from the group consisting of isobutyl, cyclopropylmethyl and benzyl, wherein R$_2$ is a sulfonyl group of formula (3) as defined herein, wherein T is —(CH$_2$)$_{mm}$—, wherein mm is 0, wherein X, Y and Z the same or different, are selected (i.e. independently) from the group consisting of H, a straight or branched alkyl group of 1 to 6 carbon atoms, Br, NO$_2$, NH$_2$, and OR$_5$, wherein R$_3$ is H, wherein wherein Cx is selected from the group consisting of COOM, and COOR$_5$, wherein M is an alkali metal (e.g. Na, K, Cs, etc.), wherein R$_5$ is as defined herein and wherein R$_4$ is selected from the group consisting of 9-fluorenylmethoxycarbonyl, 2,3-(CH$_3$O)$_2$C$_6$H$_3$CH$_2$CH$_2$CO—, 2,4-(CH$_3$O)$_2$C$_6$H$_3$CH$_2$CH$_2$CO—, 3-indole-CH$_2$CH$_2$CO—, C$_6$H$_5$CH$_2$CH$_2$CO—, C$_6$H$_5$SCH$_2$CO—, C$_6$H$_5$OCH$_2$CO—, xanthene-9-CO—, 4-CH$_3$OC$_6$H$_4$CH$_2$CH$_2$CO—, 3-CH$_3$OC$_6$H$_4$CH$_2$CH$_2$CO—, 2-CH$_3$OC$_6$H$_4$CH$_2$CH$_2$CO—, 3-NH$_2$C$_6$H$_4$CH$_2$CH$_2$CO— and

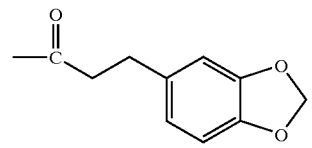

The compounds of the present invention have an affinity for aspartyl proteases, in particular, HIV aspartyl protease. Therefore, these compounds are useful as inhibitors of such proteases. These compounds can be used alone or in combination with other therapeutic or prophylactic agents, such as antivirals, antibiotics, immunomodulators or vaccines, for the treatment or prophylaxis of viral infection.

According to the present invention, the compounds of this invention are capable of inhibiting HIV viral replication in human CD4+ T-cells, by inhibiting the ability of HIV aspartyl proteases to catalyze the hydrolysis of peptide bonds. These novel compounds can thus serve to reduce the production of infectious virions from acutely and chronically infected cells, and can inhibit the initial or further infection of host cells. Accordingly, these compounds are useful as therapeutic and prophylactic agents to treat or prevent infection by HIV-1 and HIV-2, which may result in asymptomatic infection, AIDS-related complex (ARC), acquired immunodeficiency syndrome (AIDS), AIDS-related dementia, or similar diseases of the immune system, and related viruses such as HTLV-I and HTLV-II, and simian immunodeficiency virus.

As mentioned above heterocycle refers to a stable 5–7 membered monocycle or bicyclic heterocycle; it may be optionally benzofused or heterocyclofused. Each heterocycle consists of carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. The heterocyclic ring may be attached by any heteroatom or carbon atom of the cycle, which results in the benzimidazolyl, imidazolyl, imidazolinyl, imidazolidinyl, quinolyl, isoquinolyl, indolyl, pyridyl, pyrrolyl, pyrrolinyl, pyrrolidinyl, pyrazolyl, pyrazinyl, quinoxolyl, piperidinyl, morpholinyl, β-carbolinyl, tetrazolyl, thiazolidinyl, benzofuranyl, thiamorpholinyl, benzoxazolyl, oxopiperidinyl, oxopyrroldinyl, oxoazepinyl, azepinyl, isoxazolyl, tetrahydropyranyl, tetrahydrofuranyl, thiadiazolyl, thiadiazinyl, benzodioxolyl, thiophenyl, tetrahydrothiophenyl, nicoticoyl, morpholinecarbodithioyl and sulfolanyl.

As mentioned above $R_2$ and $R_4$ are each independently (i.e. same or different) selected from the above mentioned class of substituents; the may in particular be 9-fluorenylmethoxycarbonyl (Fmoc), tert-butoxycarbonyl (t-Boc), benzyloxycarbonyl (Cbz), 2-chlorobenzyloxycarbonyl (2-ClCbz), substituted aryl$SO_2$, substituted arylalkyl$SO_2$, heteroaryl$SO_2$, acyl, substituted arylalkylacyl or heteroalkylacyl groups.

The configuration of the asymmetric centre can be D, L and DL, preferably the configuration corresponding to that found in L-lysine and L-ornithine.

In addition, this invention provides pharmaceutical compositions in which these novel compounds of formula I derived from L- amino acids are used to inhibit aspartyl proteases, including HIV aspartyl proteases, thus providing protection against HIV infection.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "pharmaceutically effective amount" refers to an amount effective in treating HIV infection in a patient.

The term "prophylactically effective amount" refers to an amount effective in preventing HIV infection in a patient. As used herein, the term "patient" refers to a mammal, including a human.

The term "pharmaceutically acceptable carrier or adjuvant" and "physiologically acceptable vehicle" refer to a non-toxic carrier or adjuvant that may be administered to a patient, together with a compound of this invention, and which does not destroy the pharmacological activity thereof.

As used herein, the compounds of this invention, including the compounds of formula I are defined to include pharmaceutically acceptable derivatives thereof. A "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an antivirally active metabolite or residue thereof.

The compounds of this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

The compounds of the present invention as mention above include salts. Salts of the compounds of this invention include those derived from pharmaceutically acceptable inorganic and organic acids and bases (e.g. salts of acidic compounds of formula I with bases). Salts derived from appropriate inorganic and organic bases include for example, alkali metal (e.g., sodium), alkaline earth metal (e.g., magnesium), ammonium and N—$(C_{1-4}$ alkyl$)_4^+$ salts.

This invention also envisions ammonium salts (i.e. salts of amino groups) such as for example halide acid salts (e.g. hydrochloride, hydrobromide, hydroiodide salts). Thus the invention envisions the quaternization of any basic nitrogen containing groups (i.e. amino group(s)) of the compounds disclosed herein. The basic nitrogen can be quaternized with any agents known to those of ordinary skill in the art including, for example, lower alkyl halides, such as methyl, ethyl, propyl and butyl chlorides, bromides and iodides; dialkyl sulfates including dimethyl, diethyl, dibutyl and diamyl sulfates; long chain halides such as decyl, lauryl, myristyl and stearyl chlorides, bromides and iodides, and aralkyl halides including benzyl and phenethyl bromides. Water or oil-soluble or dispersible products may be obtained by such quaternization.

Other examples of acid salts include: acetate, adipate, alginate, aspartate, benzoate, benzenesulfonate, bisulfate, butyrate, citrate, camphorate, camphorsulfonace, cyclopentanepropionate, digluconate, dodecylhydrogensulfate, dodecylsulfate, ethanesulfonate, formate, fumarate, glucoheptanoate, glycerophosphate, glycollate, hemisulfate, heptanoate, hexanoate, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

The compounds of this invention are readily prepared using conventional techniques from commercially available and cheap starting materials.

The compounds of this invention are among the most readily prepared HIV protease inhibitors known at this point. Previously described HIV protease inhibitors are resulting from long synthetic sequences and contain more than six chiral centers, numerous peptide bonds and require air-sensitive reagents such as organometallic complexes to achieve their successful preparations. The very easy synthesis of the products described in this invention represent a marked advantage, especially for the large scale preparation of these compounds.

In the following the preparation of compounds in accordance with the present convention will be described with reference to a number of process schemes wherein the various starting reactants as well as products thereof are designated by reference numbers e.g. in scheme 1 the starting ornithine or lysine is designated with the reference number 1.

In general, amino acid derivatives of formula I are readily obtained from commercially available sources. Following the indications summarized in Scheme 1, the Nω-benzyloxycarbonyl blocking group of Nα-(9-fluorenylmethoxycarbonyl)—Nω-benzyloxycarbonyl ornithine or lysine 1 is removed by a treatment with TFA in $CH_2Cl_2$ according to the indications found in protective groups in Organic Synthesis, $3^{rd}$ Edition, p. 520–521 (T. W. Greene and P. G. M. Wuts (John Wiley & Sons, Inc. 1999). The intermediate is obtained by the evaporation of the solvent and then reacted with a sulfonyl chloride or an acyl chloride derivative in the presence of a base such as 1M potassium carbonate, affording after normal work-up the desired product 2 in excellent yields. Another possible starting material could be Nα-tert-butoxycarbonyl-Nω-benzyloxycarbonyl-L-ornithine or L-lysine 1a with the removal of the tert-butoxycarbonyl group being also achieved by a treatment with TFA in $CH_2Cl_2$. Products 2 with the Fmoc or the t-Boc groups were obtained in excellent yields.

Scheme 1

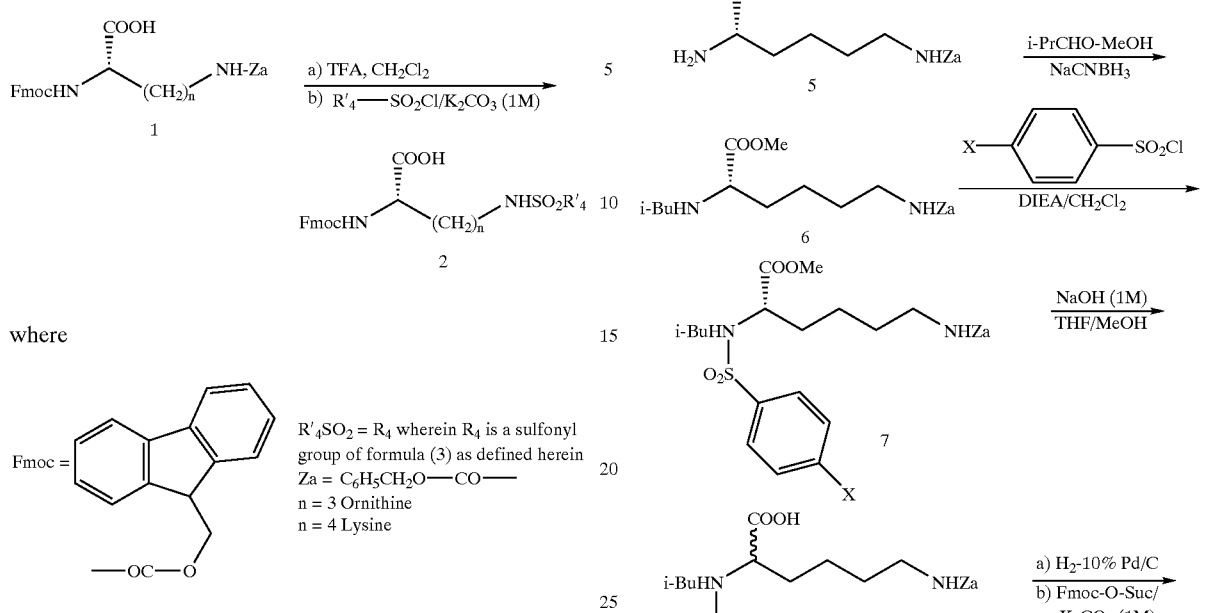

where

Fmoc = (9-fluorenyl methylene group)

R'₄SO₂ = R₄ wherein R₄ is a sulfonyl group of formula (3) as defined herein
Za = C₆H₅CH₂O—CO—
n = 3 Ornithine
n = 4 Lysine

—OC—O

Scheme 2, below, illustrates the preparation of Nα-isobutyl-Nα-(substituted benzenesulfonyl-Nε-(9-fluorenylmethoxycarbonyl) derivatives 9 from readily available material Nα-tert-butoxycarbonyl-Nε-benzyloxycarbonyl-L-lysine 3. The esterification with methyl iodide is achieved by treatment of the potassium salt in DMF with methyl iodide. Removal of the tert-butoxycarbonyl group from product 4 is done by treatment with TFA in methylene chloride. Reductive alkylation of the free amino group with isobutyraldehyde utilizing sodium cyanoborohydride provided the Nα-isobutylamino acid derivative 6. Reaction with a substituted benzenesulfonyl chloride provides the product 7, the HCl scavenger being triethylamine or diisopropylethylamine. Hydrolysis of the methyl ester is accomplished with sodium hydroxide in methanol providing the acid 8 in good yield. It should be noted that extensive epimerisation takes place in this base catalysed hydrolytic reaction. The DL derivative 8 is then submitted to hydrogenolysis to remove the terminal blocking group and the free amino group can then be acylated with 9-fluorenylmethyl chloroformate or N-(9-fluorenylmethoxycarbonyloxy) succinimide to provide the desired product 9 in its racemized form. At that step, use of a substituted sulfonyl chloride provided the corresponding sulfonyl derivative and an acylation of the same amino group with an acyl chloride or an activated acid provided the acylated derivative of general structure 9.

i-Pr = isopropyl; i-Bu = isobutyl
Me = methyl
Fmoc-O-suc = 9-Fluorenylmethoxycarbonyl-N-hydroxysuccinimide The problem of racemization was resolved by the use of a benzyl ester to block the carboxylic acid instead of a methyl ester. An additional advantage is the simultaneous removal of the two blocking groups (ester and carbamate) by hydrogenolysis, thus shortening the sequence by one step. The scheme 3, outlined below exemplifies this approach clearly.

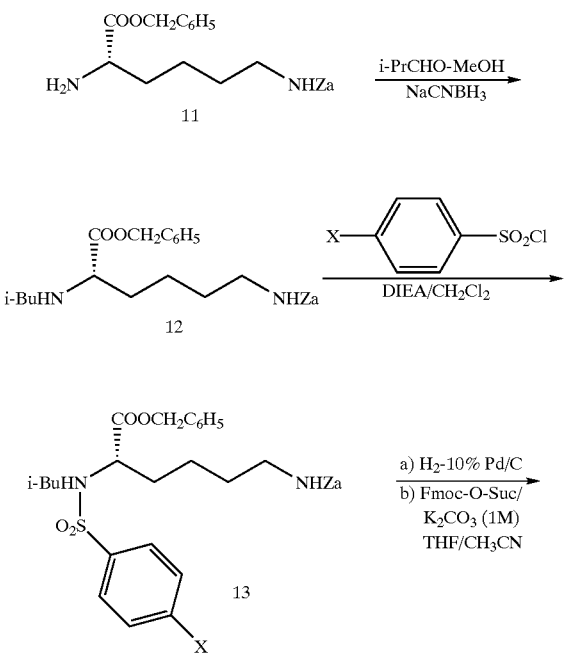

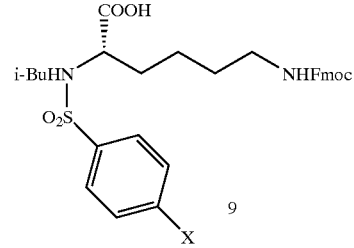

Scheme 4 demonstrates another improved approach to similar derivatives in a much shorter sequence and provide higher yields and avoid the use of protection-deprotection steps. The starting material for this sequence is a readily available commercial product, L-α-amino-ε-caprolactam 14. Reductive alkylation utilizing the sodium cyanoborohydride conditions provided the alkylated derivative 15 in 95% yield as a crystalline solid that can then be subjected to reaction with a substituted sulfonyl chloride in presence of triethylamine in methylene chloride. Product 16 was obtained in 87% yield. Treatment with 12N HCl and acetic acid for 2 hours at reflux provided the lysine derivative 17 quantitatively and the terminal amino group was then acylated with an acyl chloride or an activated carboxylic acid to provide compound 18. Scheme 4a illustrates a particular example of the process of scheme 4.

Scheme 4

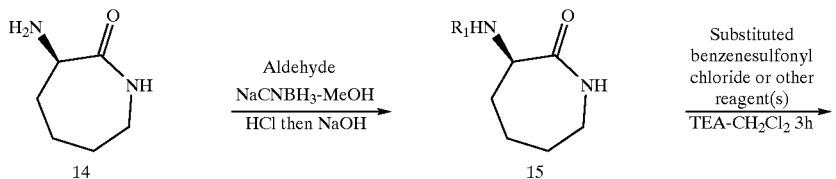

Aldehyde = R′$_1$CHO, wherein R′$_1$ is for example C$_1$ to C$_5$ alkyl

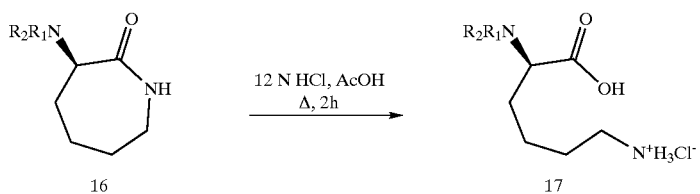

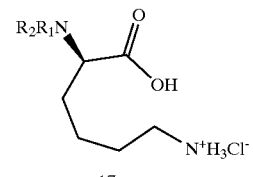

Acid chloride or other suitable or appropriate reagent(s)
Base

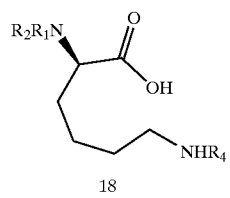

Scheme 4a

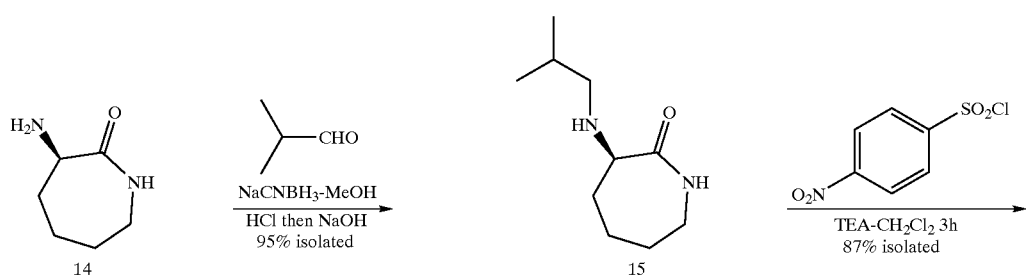

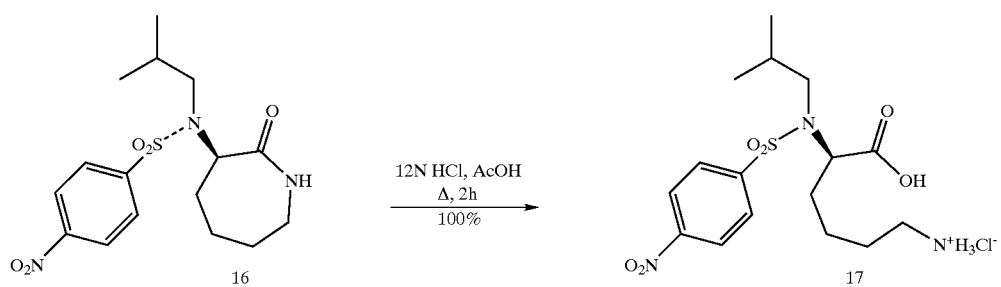

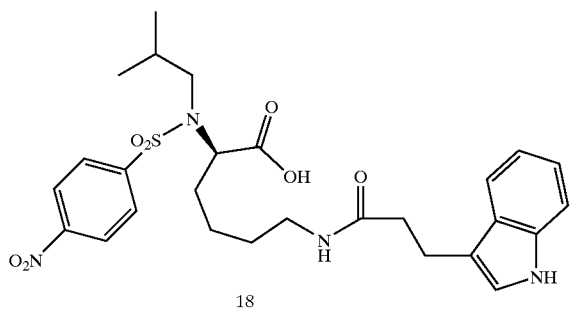

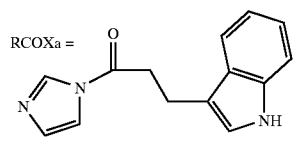

Scheme 5 summarizes the work done to obtain derivatives of structure I where n is 1. The starting material is L-serine 19a. Treatment with DEAD and triphenyl phosphine provided the β-lactone 20 that was then treated with ammonia in ethanol. The Nα-tert-butoxycarbonyl-Nβ-amino propionic acid derivative was then reacted as usual with a substituted benzenesulfonyl chloride, providing product 21. The removal of the blocking group and its replacement by another one (v.g. Fmoc) provided compound 22. Scheme 5a illustrates a particular example of the process of scheme 5.

Scheme 5

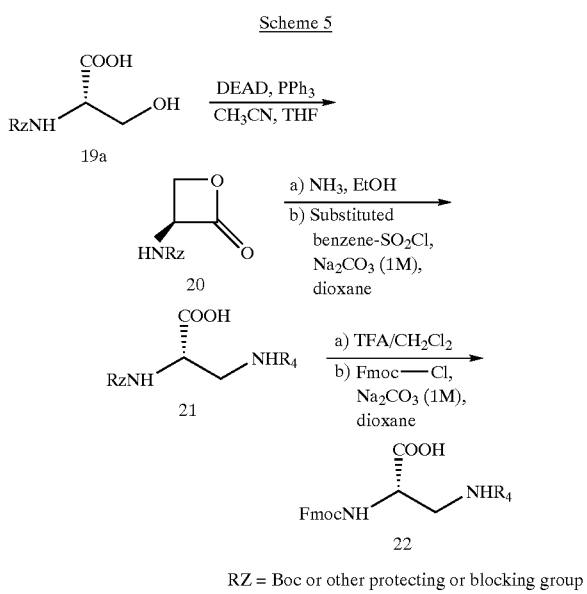

RZ = Boc or other protecting or blocking group

Scheme 5a

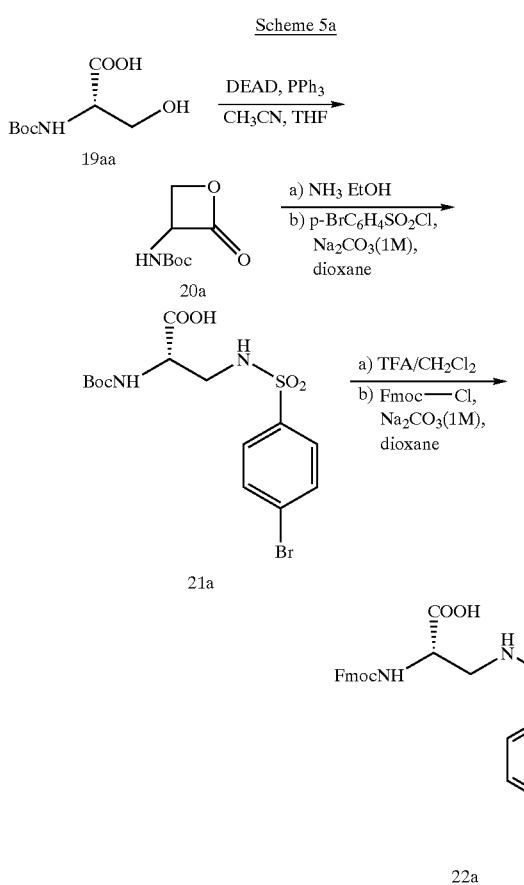

Scheme 6 below relates to an alternative process whereby compounds of formula I as defined herein may be obtained wherein W is —CH$_2$—XX—CH$_2$—CH$_2$—, XX being as defined herein. Thus reductive alkylation of L-serine methyl ester 19b may give rise to compound 23 which may be treated with a substituted benzenesulfonyl chloride to give a compound 24. Further treatment of compound 24 with tosyl chloride in dichloromethane and triethylamine may give rise to a α, β-unsaturated ester 25. Michael addition of a substituted ethylenediamine and saponification may give rise to compound 26. The α, β-unsaturated ester 25 may be treated with a variety of reagents to provide compounds containing a heteroatom as shown in Table 2 for compound nos. 205, 206 and 207. The chiral derivatives may also be obtained via ring opening of a β-lactone derived form 24 to give pure L isomers 26.

Scheme 6

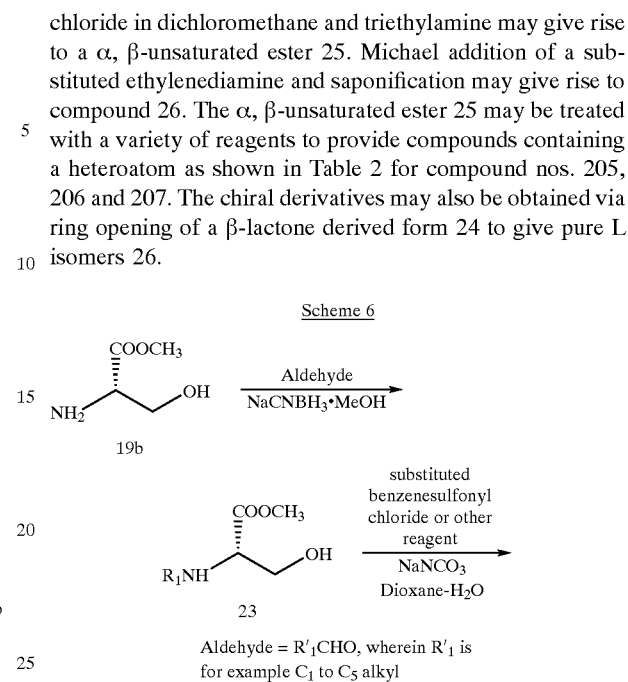

Scheme 7 provides a summary of the approach of products of structure I where n is 2. Again the starting material is a simple product L-homoserine 27. The amino group is protected by the tert-butoxycarbonyl group and treatmemt with diazomethane in ether provided derivative 28. The next sequence is the transformation of the hydroxyl group to an amino group, which is easily achieved by treatment of 28 with 4-methylbenzenesulfonyl chloride in pyridine and methylene chloride followed by displacement of the tosyl group by azide in DMF. The product 29 is then reduced by hydrogen gas in presence of 10% Pd/C and the resulting amino group is reacted with a substituted benzenesulfonyl chloride, providing an excellent yield of derivative 30. Its conversion to another group on the alpha amino group is performed as previously described by the removal of the tert-butoxycarbonyl group with TFA in methylene chloride and then reaction with 9-fluorenylmethyl chloroformate or N-(9-fluorenylmethoxycarbonyloxy) succinimide, providing the final compound 31.

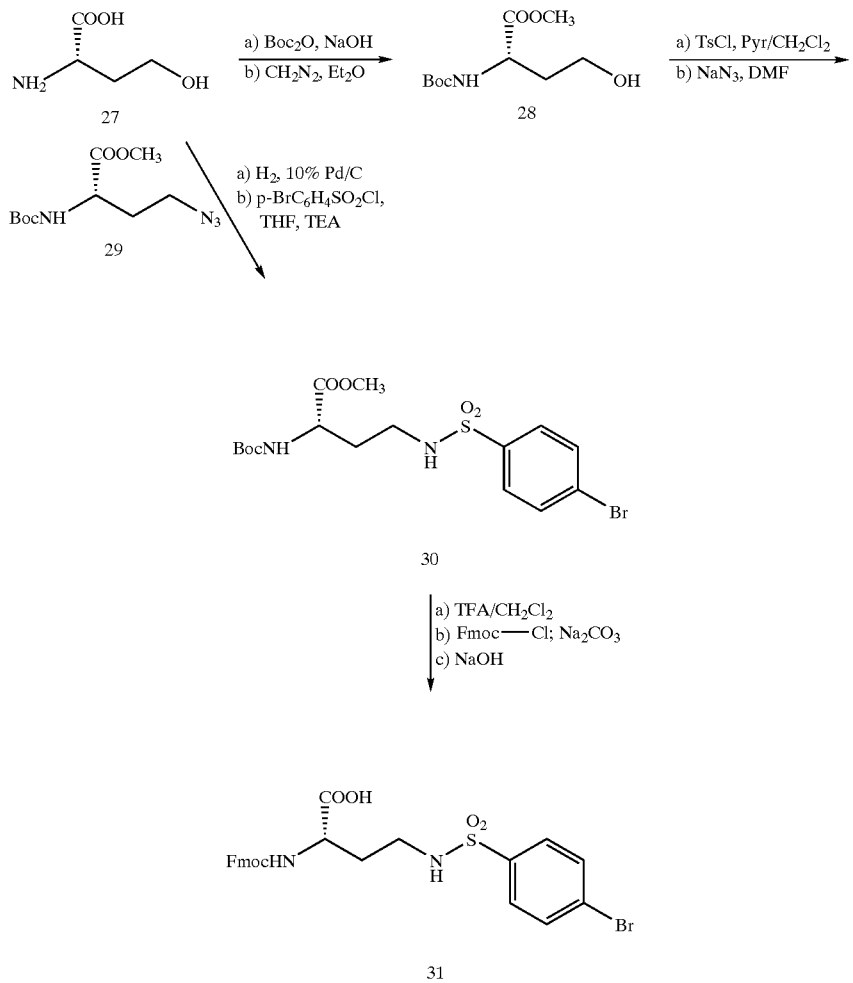

Scheme 7

As it can be appreciated by the skilled artisan, the above synthetic schemes are not intended to be a comprehensive list of all means by which the compounds described and claimed in this application may be synthesized. Further methods will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

As discussed above, the novel compounds of the present invention are excellent ligands for asp artyl proteases, particularly HIV-1 protease. Accordingly, these compounds are capable of targeting and inhibiting late stage events in the replication, i.e.; the processing of the viral polyproteins by HIV encoded protease. Compounds according to this invention advantageously inhibit the ability of the HIV-1 virus to infect immortalized human T cells over a period of days, as determined by an assay of extracellular p24 antigen—a specific marker of viral replication (see, Meek et al., Nature, 343, pp. 90–92 (1990)).

In addition to their use in the prophylaxis or treatment of HIV or HTLV infection, the compounds according to this invention may also be used as inhibitory or interruptive agents for other viruses which depend on aspartyl proteases, similar to HIV or HTLV aspartyl proteases, for obligatory events in their life cycle. Such compounds inhibit the proteolytic processing of viral polyprotein precursors by inhibiting aspartyl protease. Because aspartyl protease is essential for the production of mature virions, inhibition of that processing effectively blocks the spread of virus by inhibiting the production and reproduction of infectious virions, particularly from chronically infected cells. The compounds of this invention advantageously inhibit aspartyl proteases, thus blocking the ability of aspartyl proteases to catalyze the hydrolysis of peptide bonds.

The compounds of this invention may be employed in a conventional manner for the treatment or prevention of HIV, HTLV, and other viruses, which depend on aspartyl proteases for obligatory events in their life cycle. Such methods of treatment, their dosage levels and requirements may be selected by those of ordinary skill in the art from available methods and techniques. For example, a compound of this invention may be combined with a pharmaceutically acceptable adjuvant for administration to a virally infected patient in a pharmaceutically acceptable manner and in an amount effective to lessen the severity of the viral infection.

Alternatively, the compounds of this invention may be used in vaccines and methods for protecting individuals against viral infection over an extended period of time. The compounds may be employed in such vaccines either alone or together with other compounds of this invention in a manner consistent with the conventional utilization of protease inhibitors in vaccines. For example, a compound of this invention may be combined with pharmaceutically acceptable adjuvants conventionally employed in vaccines and administered in prophylactically effective amounts to protect individuals over an extended period of time against viral infections, such as HIV infection. As such, the novel protease inhibitors of this invention can be administered as agents for treating or preventing viral infections, including HIV infection, in a mammal.

The compounds of this invention may be administered to a healthy or HIV-infected patient either as a single agent or in combination with other antiviral agents which interfere with the replication cycle of HIV. By administering the compounds of this invention with other antiviral agents which target different events in the viral life cycle, the therapeutic effect of these compounds is potentiated. For instance, the co-administered antiviral agent can be one which targets early events in the life viral cycle, such as cell entry, reverse transcription and viral DNA integration into cellular DNA. Antiviral agents targeting such early life cycle events include didanosine (ddI), zalcitabine (ddC), stavudine (d4T), zidovudine (AZT), polysulfated polysaccharides, sT4 (soluble CD4)—which blocks attachment or adsorption of the virus to host cells—and other compounds which block binding of virus to CD4 receptors on CD4 bearing T-lymphocytes and other CD4(+) cells, or inhibit fusion of the viral envelope with the cytoplasmic membrane. Other retroviral reverse transcriptase inhibitors, such as derivatives of AZT, may also be co-administered with the compounds of this invention to provide therapeutic treatment for substantially reducing or eliminating viral infectivity and the symptoms associated therewith. Examples of other antiviral agents include ganciclovir, dideoxycytidine, trisodium phosphonoformate, eflornithine, ribavirin, acyclovir, alpha interferon and trimenotrexate. Additionally, non-ribonucleoside inhibitors of reverse transcriptase, such as TIBO or nevirapine, may be used to potentiate the effect of the compounds of this invention, as may viral uncoating inhibitors, inhibitors of trans-activating proteins such as tat or rev, antisense molecules or inhibitors of the viral integrase. These compounds may also be co-administered with other inhibitors of HIV aspartyl protease.

Combination therapies according to this invention exert a synergistic effect in inhibiting HIV replication because each component agent of the combination acts on a different site of HIV replication. The use of such combinations also advantageously reduces the dosage of a given conventional anti-retroviral agent that would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce the potential of resistance to single agent therapies, while minimizing any associated toxicity. These combinations may also increase the efficacy of the conventional agent without increasing the associated toxicity. Preferred combination therapies include the administration of a compound of this invention with AZT, 3TC, ddI, ddC, d4T or other reverse transcriptase inhibitors.

Alternatively, the compounds of this invention may also be co-administered with other HIV protease inhibitors such as Ro 31-8959 (Saquinavir/Fortovase; Roche), L-735,524 (Indinavir; Merck), AG-1343 (Nelfinavir; Agouron), A-84538 (Ritonavir; Abbott) and VX-478 (Amprenavir; Glaxo) to increase the effect of therapy or prophylaxis against various viral mutants or members of other HIV quasi species.

We prefer administering the compounds of this invention as single agents or in combination with retroviral reverse transcriptase inhibitors, or other HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The compounds of this invention can also be administered in combination with immunomodulators (e.g., bropirimine, anti-human alpha interferon antibody, IL-2, GM-CSF, methionine enkephalin, interferon alpha, diethyldithiocarbante, tumor necrosis factor, naltrexone and rEPO) antibiotics (e.g., pentamidine isethionate) or vaccines to prevent or combat infection and disease associated with HIV infection, such as AIDS and ARC.

When the compounds of this invention are administered in combination therapies with other agents, they may be administered sequentially or concurrently to the patient. Alternatively, pharmaceutical or prophylactic compositions according to this invention may be comprised of a combination of an aspartyl protease inhibitor of this invention and another therapeutic or prophylactic agent.

Although this invention focuses on the use of the compounds disclosed herein for preventing and treating HIV infection, the compounds of this invention can also be used as inhibitory agents for other viruses that depend on similar aspartyl proteases for obligatory events in their life cycle. These viruses include, but are not limited to other AIDS-like diseases caused by retroviruses, such as simian immunodeficiency viruses, HIV-2, HTLV-I and HTLV-II. In addition, the compounds of this invention may also be used to inhibit other aspartyl proteases and, in particular, other human aspartyl proteases including renin and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol and wool fat.

The pharmaceutical compositions of this invention may be administered orally, parenterally by inhalation spray, topically, rectally, nasally, buccally, vaginally or via an implanted reservoir. We prefer oral administration or administration by injection. The pharmaceutical compositions of this invention may contain any conventional non-toxic pharmaceutically acceptable carriers, adjuvants or vehicles. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are amino acid, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv. or a similar alcohol.

The pharmaceutical compositions of this invention may be orally administered in any orally acceptable dosage form including, but not limited to, capsules, tablets, and aqueous suspension and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxy-ethylene or polyoxypropylene compound, emulsifying wax and water. Alternatively, the pharmaceutical compositions can be formulated with a suitable lotion or cream containing the active compound suspended or dissolved in a carrier. Suitable carriers include, but are not limited to, mineral oil, sorbitan monostearate, polysorbate 60, cetyl esters wax cetearyl alcohol, 2-octyldodecanol, benzyl alcohol and water. The pharmaceutical compositions of this invention may also be topically applied to the lower intestinal tract by rectal suppository formulation or in a suitable neat formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage levels of between about 0.01 and about 25 mg/kg body weight per day, preferably between about 0.5 and about 25 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis, upon any recurrence of disease symptoms.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

The compounds of this invention are also useful as commercial reagents which effectively bind to aspartyl proteases, particularly HIV aspartyl protease. As commercial reagents, the compounds of this invention, and their derivatives, may be used to block proteolysis of a target peptide, such as an aspartyl protease, or may be derivatized to bind to a stable resin as a tethered substrate for affinity chromatography applications. These and other uses which characterize commercial aspartyl protease inhibitors will be evident to those of ordinary skill in the art.

An Enzymatic assay for determining the inhibition constant (Ki) of synthetic compounds targeting the HIV protease may be carried out as follows: This is a fluorometric assay based on the cleavage by protease of a substrate carrying a donor group (EDANS) and an acceptor group (DABCYL) on each side of the cleavage site, interacting together through fluorescence resonance energy transfer (FRET). Cleavage of the substrate by protease stops energy exchange between the two groups, resulting in a time-dependent increase in fluorescence intensity that is linearly related to the extent of substrate hydrolysis.

The enzymatic assay is done at 31° C. in white 96-well fluorescence microplates, in a total volume of 200 µL per well. The apparatus used for analysis is a FL600 fluorescence microplate reader (Biotek Instruments). The reaction is run first in the absence of protease inhibitors for 4 min, using 156 µL of buffer at pH 4.7 (sodium acetate 100 mM, NaCl 1 M, EDTA 1 mM, DTT 1 mM, dimethylsulfoxide 10%, and BSA 1 mg/mL), 20 µL of substrate H-2930 from Molecular Probes (final concentration 10 µM) and 20 µL of recombinant HIV-1 protease (final concentration 2.18 nM) purchased from Bachem Bioscience. Excitation of the fluorophore is done at 340 nm and emission at 485 nm is recorded continuously during the reaction, allowing determination of the enzyme's initial velocity ($v_0$). At the end of the 4 min incubation, the potential inhibitor at a defined concentration in a volume of 4 µL is added to the reaction, and fluorescence readings are taken for another 4 min, allowing determination of enzyme velocity ($v_i$) in the presence of the inhibitory compound. Several concentrations of the putative inhibitors are tested in the assay. After calculation of $v_0$ and $v_i$, the inhibition constant (Ki) of the compound is determined using the equation of Henderson:

$$\frac{Vo}{Vi} = 1 + \frac{[I]}{Ki_{app}}$$

Where $$Ki = \frac{Ki_{app}}{1 + \frac{[S]}{Km}}$$

and [I]=inhibitor concentration, [S]=substrate concentration,

Km=Michaelis-Menten constant, $Ki_{app}$=apparent Ki

Note that the Michaelis-Menten constant of HIV protease is determined by running the assay without inhibitors, using several concentrations of substrate, and plotting the results as a Cornish-Bowden graph with the ratio substrate concentration/velocity as the ordinate and substrate concentration as the abscissa. Graphs are traced and the Ki determined using GraphPad Prism software v. 3.0.

The compounds listed in Tables 1 and 2 below were prepared by following Schemes 1, 2, 3, 4, 5, 6 or 7 above or using reaction conditions known to those skilled in the art. The activities of the compounds are also listed in the same table demonstrating their potential usefulness. In Table 1 are shown compounds of formula Ia, as defined above, wherein W is —(CH$_2$)$_n$— and wherein n, Cx, R$_1$, R$_2$, R$_3$, and R$_4$, are set forth for each compound mentioned therein. In Table 2 are shown compounds of formula Ia, as defined above, wherein W is —CH$_2$—XX—CH$_2$CH$_2$— and wherein Cx, R$_1$, R$_2$, R$_3$, and R$_4$, are set forth for each compound mentioned therein.

TABLE 1

| Compound No. | Cx | $R_1$ | $R_2$ | $R_3$ | $R_4$ | n | Ki (nM) | D, L, DL R, S, RS |
|---|---|---|---|---|---|---|---|---|
| 1 | COOH | $i\text{-}C_4H_9$ | $4\text{-}ClC_6H_4SO_2$ | H | Fmoc | 4 | 20.5 | DL |
| 2 | COOH | $i\text{-}C_4H_9$ | $4\text{-}CH_3C_6H_4SO_2$ | H | Fmoc | 4 | 5.0 | DL |
| 3 | COOH | $i\text{-}C_4H_9$ | $4\text{-}FC_6H_4SO_2$ | H | Fmoc | 4 | 17.4 | DL |
| 4 | COOH | $i\text{-}C_4H_9$ | $4\text{-}BrC_6H_4SO_2$ | H | Fmoc | 4 | 11.4 | L |
| 5 | COOH | $i\text{-}C_4H_9$ | $4\text{-}CH_3C_6H_4SO_2$ | H | Fmoc | 3 | 334 | D |
| 6 | COOH | $i\text{-}C_4H_9$ | $4\text{-}CH_3OC_6H_4SO_2$ | H | Fmoc | 4 | 180 | DL |
| 7 | COOH | $i\text{-}C_4H_9$ | 1-naphthyl-$SO_2$ | H | Fmoc | 4 | 10.6 | L |
| 8 | COOH | $i\text{-}C_4H_9$ | $C_6H_5SO_2$ | H | Fmoc | 4 | 54.9 | L |
| 9 | COOH | $i\text{-}C_4H_9$ | $4\text{-}t\text{-}BuC_6H_4SO_2$ | H | Fmoc | 4 | 18.7 | L |
| 10 | COOH | $i\text{-}C_4H_9$ | $4\text{-}BrC_6H_4SO_2$ | H | Fmoc | 4 | 257 | L |
| 11 | COOH | $i\text{-}C_4H_9$ | $4\text{-}CH_3C_6H_4SO_2$ | H | Fmoc | 4 | 15.4 | DL |
| 12 | COOH | $i\text{-}C_4H_9$ | $4\text{-}CH_3C_6H_4SO_2$ | H | t-Boc | 4 | 8,000 | L |
| 13 | COOCH$_3$ | H | Fmoc | H | $4\text{-}BrC_6H_4SO_2$ | 4 | 25,000 | L |
| 14 | COOCH$_3$ | H | Fmoc | H | $4\text{-}BrC_6H_4SO_2$ | 2 | 49,000 | L |
| 15 | COOCH$_3$ | H | Fmoc | H | $4\text{-}BrC_6H_4SO_2$ | 4 | 47,000 | L |
| 16 | COOH | H | $4\text{-}BrC_6H_4SO_2$ | H | $4\text{-}BrC_6H_4SO_2$ | 4 | 13,000 | L |
| 17 | COOH | H | Fmoc | H | $4\text{-}BrC_6H_4SO_2$ | 3 | 7,700 | L |
| 18 | COOH | H | Fmoc | H | $4\text{-}BrC_6H_4SO_2$ | 1 | 75,000 | L |
| 19 | COOH | H | Fmoc | H | $4\text{-}BrC_6H_4SO_2$ | 4 | 12,900 | D |
| 20 | CONH$_2$ | H | Fmoc | H | $4\text{-}BrC_6H_4SO_2$ | 4 | 23,000 | RS |
| 21 | CH2OH | H | Fmoc | $i\text{-}C_4H_9$ | $4\text{-}BrC_6H_4SO_2$ | 4 | 2,000 | L |
| 22 | COOH | H | $3\text{-}CO\text{-}4\text{-}OH\text{-}7\text{-}CF_3\text{-}quinoline$ | H | $4\text{-}BrC_6H_4SO_2$ | 4 | >6,000 | S |
| 23 | COOH | H | Fmoc | H | $2\text{-}BrC_6H_4SO_2$ | 4 | >50,000 | L |
| 24 | COOH | H | Fmoc | H | $2,4,6\text{-}(i\text{-}C_3H_7)_3C_6H_2SO_2$ | 4 | 36,000 | L |
| 25 | COOH | H | Fmoc | H | $2,4,6\text{-}(CH_3)_3C_6H_2SO_2$ | 4 | >3,100 | L |
| 26 | CO—NH-Fmoclysyl | H | Fmoc | H | $2,4,6\text{-}(CH_3)_3C_6H_2SO_2$ | 4 | 63,000 | L |
| 27 | COOH | H | Fmoc | H | 8-quinoline-$SO_2$ | 4 | >50,000 | L |
| 28 | COOH | H | Fmoc | H | $4\text{-}BrC_6H_4SO_2$ | 4 | 15,000 | L |
| 29 | COOH | H | CO—CH$_2$-3-indole | H | $4\text{-}BrC_6H_4SO_2$ | 4 | 10,500 | L |
| 30 | COOH | H | CO—CH$_2$-9-fluorene | H | $4\text{-}BrC_6H_4SO_2$ | 4 | 71,000 | L |
| 31 | COOH | H | Fmoc | H | 1-naphthyl-$SO_2$ | 4 | 11,500 | L |
| 32 | COOH | H | Fmoc | H | 2-naphthyl-$SO_2$ | 4 | 10,000 | L |
| 33 | COOH | H | Fmoc | $i\text{-}C_4H_9$ | $C_6H_5CH_2SO_2$ | 4 | 20,000 | L |
| 34 | COOH | H | Fmoc | H | $3\text{-}CF_3C_6H_4SO_2$ | 4 | 22,000 | L |
| 35 | COOH | H | Fmoc | H | camphor-10-$CH_2SO_2$ | 4 | 33,000 | L |
| 36 | COOH | $i\text{-}C_4H_9$ | CO—CH$(C_6H_5)_2$ | H | $4\text{-}BrC_6H_4SO_2$ | 4 | 24,000 | L |
| 37 | COOH | $C_6H_5CH_2$ | CO—COH$(C_6H_5)_2$ | H | $4\text{-}BrC_6H_4SO_2$ | 4 | 54,000 | L |
| 38 | COOH | H | CO-9-fluorene | H | $4\text{-}BrC_6H_4SO_2$ | 4 | 4,700 | L |
| 39 | COOH | $i\text{-}C_4H_9$ | $4\text{-}ClC_6H_4SO_2$ | H | COOCH$_2$C$_6$H$_5$ | 4 | >100 | L |
| 40 | COOH | $C_6H_5CH_2$ | $4\text{-}CH_3C_6H_4SO_2$ | H | COOCH$_2$C$_6$H$_5$ | 4 | 19.6 | L |
| 41 | COOH | H | Fmoc | $i\text{-}C_4H_9$ | Fmoc | 3 | >50,000 | L |
| 42 | COOH | $i\text{-}C_4H_5$ | $2,4,6\text{-}(CH_3)_3C_6H_2SO_2$ | H | $4\text{-}BrC_6H_4SO_2$ | 4 | >100 | L |
| 43 | COOH | $CH_2\text{-}c\text{-}C_3H_5$ | $4\text{-}ClC_6H_4SO_2$ | H | Fmoc | 4 | 33,000 | L |
| 44 | COOH | $i\text{-}C_4H_9$ | $4\text{-}NH_2C_6H_4SO_2$ | H | Fmoc | 4 | 2.1 | L |
| 45 | COOH | $i\text{-}C_4H_9$ | $4\text{-}BrC_6H_4SO_2$ | H | COOCH$_2$C$_6$H$_5$ | 4 | >100 | DL |

TABLE 1-continued

| Compound No. | Cx | R₁ | R₂ | R₃ | R₄ | n | Ki (nM) | D, L, DL R, S, RS |
|---|---|---|---|---|---|---|---|---|
| 46 | COOH | i-C₄H₉ | COC₆H₅ | H | Fmoc | 4 | >100 | L |
| 47 | COOH | i-C₄H₉ | 4-CH₃C₆H₄SO₂ | H | COOCH₂C₆H₅ | 4 | >100 | L |
| 48 | COOH | i-C₄H₉ | 4-IC₆H₄SO₂ | H | COOCH₂C₆H₅ | 4 | >100 | DL |
| 49 | COOH | H | Fmoc | H | C₆H₅SO₂ | 4 | 8,900 | L |
| 50 | COOH | H | CO-9-fluorene | H | 4-NO₂C₆H₄SO₂ | 3 | 6,000 | L |
| 51 | COOH | H | Fmoc | H | 4-BrC₆H₄SO₂ | 4 | 9,300 | L |
| 52 | COOH | H | Fmoc | H | 4-NH₂C₆H₄SO₂ | 3 | 6,800 | L |
| 53 | COOH | H | Fmoc | H | 4-ClC₆H₄SO₂ | 4 | 4,800 | L |
| 54 | COOH | H | Fmoc | H | 2,5-Cl₂C₆H₃SO₂ | 4 | >6,250 | L |
| 55 | COOH | H | Fmoc | H | 4-FC₆H₄SO₂ | 4 | 6,500 | L |
| 56 | COOH | t-Boc | 4-BrC₆H₄CH₂ | 4-BrC₆H₄CH₂ | 4-BrC₆H₄SO₂ | 4 | >25,000 | L |
| 57 | COOH | H | 4-BrC₆H₄SO₂ | H | 4-BrC₆H₄SO₂ | 3 | 42,400 | L |
| 58 | COOH | H | 4-FC₆H₄SO₂ | 4-FC₆H₄CH₂ | COOCH₂C₆H₅ | 4 | >6,500 | L |
| 59 | COOH | H | 4-BrC₆H₄SO₂ | 4-FC₆H₄CH₂ | 4-BrC₆H₄SO₂ | 3 | >34,900 | L |
| 60 | COOH | H | 4-BrC₆H₄SO₂ | 4-FC₆H₄CH₂ | 4-BrC₆H₄SO₂ | 4 | >50,000 | L |
| 61 | COOH | H | Fmoc | H | 4-CH₃OC₆H₄SO₂ | 3 | 17,400 | L |
| 62 | COOH | H | Fmoc | H | 4-NO₂C₆H₄SO₂ | 3 | 26,200 | L |
| 63 | COOH | H | Fmoc | H | 4-ClC₆H₄SO₂ | 4 | 19,200 | L |
| 64 | COOH | H | Fmoc | H | 4-IC₆H₄SO₂ | 4 | >50,000 | L |
| 65 | COOH | H | C₆H₅CO | H | 4-BrC₆H₄SO₂ | 4 | 1,900 | L |
| 66 | COOH | H | 4-BrC₆H₄SO₂ | H | Fmoc | 4 | 4.3 | L |
| 67 | COOH | i-C₄H₉ | 4-CH₃C₆H₄SO₂ | H | Fmoc | 4 | 8.1 | L |
| 68 | COONa | i-C₄H₅ | C₆H₅CH=CHSO₂ | H | 4-NH₂C₆H₄SO₂ | 3 | 23,800 | L |
| 69 | COOH | H | 4-AcNHC₆H₄SO₂ | H | Fmoc | 4 | >12,500 | L |
| 70 | COOH | H | 4-NO₂C₆H₄SO₂ | H | 2-NO₂C₆H₄SO₂ | 4 | 44,800 | L |
| 71 | COOH | H | 2-NO₂C₆H₄SO₂ | H | Fmoc | 4 | 2,385 | L |
| 72 | COOH | H | 4-MeC₆H₄SO₂ | H | Fmoc | 3 | 1,300 | L |
| 73 | COOH | H | 4-MeC₆H₄SO₂ | H | Fmoc | 3 | 14,200 | L |
| 74 | COOH | H | 4-ClC₆H₄SO₂ | H | Fmoc | 4 | >1,250 | L |
| 75 | COOCH₂C₆H₅ | i-C₄H₉ | 4-CH₃C₆H₄SO₂ | H | COOCH₂C₆H₅ | 4 | >1,250 | L |
| 76 | COOCH₂C₆H₅ | i-C₄H₉ | 4-CH₃C₆H₄SO₂ | H | COOCH₂C₆H₅ | 4 | >1,250 | L |
| 77 | COOCH₂C₆H₅ | i-C₄H₉ | 4-CH₃C₆H₄SO₂ | H | COOCH₂C₆H₅ | 4 | >1,250 | L |
| 78 | COOCH₂C₆H₅ | i-C₄H₉ | 4-CH₃C₆H₄SO₂ | H | COOCH₂C₆H₅ | 4 | >1,250 | L |
| 79 | COOCH₂C₆H₅ | i-C₄H₉ | 4-CH₃C₆H₄SO₂ | H | COOCH₂C₆H₅ | 4 | >1,250 | L |
| 80 | COOCH₂C₆H₅ | Et₂CHCH₂ | 4-MeC₆H₄SO₂ | H | Fmoc | 4 | >1,250 | L |
| 81 | COOCH₂C₆H₅ | MeEtCHCH₂ | 4-MeC₆H₄SO₂ | H | Fmoc | 4 | >1,250 | L |
| 82 | COOH | H | Fmoc | H | Fmoc | CH₂SSCH₂ | >1,250 | L |
| 83 | COOH | i-C₄H₉ | 4-CH₃C₆H₄SO₂ | H | COOCH₂C₆H₅ | 4 | 105 | L |
| 84 | COOH | i-C₄H₉ | 4-CH₃C₆H₄SO₂ | H | CO—CH₂-9-fluorene | 4 | 89.7 | L |
| 85 | COOH | i-C₄H₉ | 4-CH₃C₆H₄SO₂ | H | CO-9-xanthene | 4 | 14.5 | L |
| 86 | COOH | i-C₄H₉ | 4-CH₃C₆H₄SO₂ | H | CO—CH(C₆H₅)₂ | 4 | 171 | L |
| 87 | COOH | i-C₄H₉ | 4-CH₃C₆H₄SO₂ | H | CO-3-indole | 4 | >1,250 | L |
| 88 | COOH | i-C₄H₉ | 4-CH₃C₆H₄SO₂ | H | CO-2-indole | 4 | >625 | L |
| 89 | COOH | i-C₄H₉ | 4-CH₃C₆H₄SO₂ | H | COCH₂CH₂-3-indole | 4 | 6.9 | L |
| 90 | COOH | i-C₄H₉ | 4-CH₃C₆H₄SO₂ | H | COCH=CHC₆H₅ | 4 | 747 | L |
| 91 | COOH | i-C₄H₉ | 4-CH₃C₆H₄SO₂ | H | COCH₂CH₂C₆H₅ | 4 | 8.0 | L |

TABLE 1-continued

| Compound No. | Cx | R₁ | R₂ | R₃ | R₄ | n | Ki (nM) | D, L, DL R, S, RS |
|---|---|---|---|---|---|---|---|---|
| 92 | COOH | i-C₄H₉ | 4-CH₃C₆H₄SO₂ | H | COO-Cholesteryl | 4 | >1,250 | L |
| 93 | COOH | i-C₄H₉ | 4-CH₃C₆H₄SO₂ | H | CO-2-quinoine | 4 | 152 | L |
| 94 | COOH | i-C₄H₉ | 4-NO₂C₆H₄SO₂ | H | COCH₂CH₂C₆H₅ | 4 | 33.9 | L |
| 95 | COOH | i-C₄H₉ | 4-NO₂C₆H₄SO₂ | H | COCH₂CH₂-3-indole | 4 | 33.4 | L |
| 96 | COOH | i-C₄H₉ | 4-NO₂C₆H₄SO₂ | H | CO-9-xanthene | 4 | 43.9 | L |
| 97 | COOH | i-C₄H₉ | 4-C₆H₅CH₂CH₂CONHC₆H₄SO | H | COCH₂CH₂C₆H₅ | 4 | 33.0 | L |
| 98 | COOH | i-C₄H₉ | 4-NH₂C₆H₄SO₂ | H | COCH₂CH₂-3-indole | 4 | 10.1 | L |
| 99 | COOH | i-C₄H₉ | 4-NH₂C₆H₄SO₂ | H | CO-9-xanthene | 4 | 12.1 | L |
| 100 | COOH | i-C₄H₉ | 4-NH₂C₆H₄SO₂ | H | COCH₂C₆H₅ | 4 | 18.1 | L |
| 101 | COOH | i-C₄H₉ | 4-CH₃C₆H₄SO₂ | H | C₆H₅CH=CHSO₂ | 4 | >3,000 | L |
| 102 | COOH | i-C₄H₉ | 1-naphthyl-SO₂ | H | Fmoc | 4 | 2,320 | L |
| 103 | COOH | H | 4-NO₂C₆H₄SO₂ | H | Fmoc | 4 | 3,300 | L |
| 104 | COOH | H | 4-CH₃OC₆H₄SO₂ | H | Fmoc | 4 | 3,160 | L |
| 105 | COOH | H | 2-NH₂C₆H₄SO₂ | H | Fmoc | 4 | 16,000 | L |
| 106 | COOH | H | 4-NH₂C₆H₄SO₂ | H | Fmoc | 4 | 4,490 | L |
| 107 | COOH | H | 2-NO₂C₆H₄SO₂ | H | Fmoc | 4 | 3,970 | L |
| 108 | COOH | i-C₄H₉ | 4-NO₂C₆H₄SO₂ | H | 3-NO₂C₆H₄CH=CHCO | 4 | 34.4 | L |
| 109 | COOH | i-C₄H₉ | 4-NO₂C₆H₄SO₂ | H | 2-NO₂C₆H₄CH=CHCO | 4 | 21.7 | L |
| 110 | COOH | i-C₄H₉ | 4-NO₂C₆H₄SO₂ | H | 2,3-(CH₃O)₂C₆H₃CH=CHCO | 4 | >300 | L |
| 111 | COOH | i-C₄H₉ | 4-NO₂C₆H₄SO₂ | H | 4-NO₂C₆H₄CH=CHCO | 4 | >300 | L |
| 112 | COOH | i-C₄H₉ | 4-NO₂C₆H₄SO₂ | H | C₆H₅CH=CHCO | 4 | >300 | L |
| 113 | COOH | i-C₄H₉ | 4-NO₂C₆H₄SO₂ | H | 4-CH₃OC₆H₄CH=CHCO | 4 | >300 | L |
| 114 | COOH | i-C₄H₉ | 4-NO₂C₆H₄SO₂ | H | 4-CH₃C₆H₄CH=CHCO | 4 | >300 | L |
| 115 | COOH | i-C₄H₉ | 4-NO₂C₆H₄SO₂ | H | C₆H₅CH₂SO₂ | 4 | >300 | L |
| 116 | COOH | i-C₄H₉ | 4-NO₂C₆H₄SO₂ | H | 4-NO₂C₆H₄SO₂ | 4 | >300 | L |
| 117 | COOH | i-C₄H₉ | 4-NH₂C₆H₄SO₂ | H | 3-NH₂C₆H₄CH₂CH₂CO | 4 | 20.5 | L |
| 118 | COOH | i-C₄H₉ | 4-NH₂C₆H₄SO₂ | H | 2,3-(CH₃O)₂C₆H₃CH₂CH₂CO | 4 | 6.2 | L |
| 119 | COOH | i-C₄H₉ | 4-NH₂C₆H₄SO₂ | H | 4-CH₃OC₆H₄CH₂CH₂CO | 4 | 12.4 | L |
| 120 | COOH | i-C₄H₉ | 4-NH₂C₆H₄SO₂ | H | C₆H₅CH₂CH₂CH₂CO | 4 | >300 | L |
| 121 | COOH | i-C₄H₉ | 4-NH₂C₆H₄SO₂ | H | 2-NH₂C₆H₄CH₂CH₂CO | 4 | >300 | L |
| 122 | COOH | i-C₄H₉ | 4-NH₂C₆H₄SO₂ | H | Fmoc | 4 | >300 | L |
| 123 | COOCH₃ | i-C₄H₉ | 4-CH₃C₆H₄SO₂ | H | Fmoc | 4 | 208 | R |
| 124 | CH₂OH | i-C₄H₉ | 4-CH₃C₆H₄SO₂ | H | Fmoc | 4 | 107 | RS |
| 125 | CONH₂ | i-C₄H₉ | 4-CH₃C₆H₄SO₂ | H | 4-HOC₆H₄CH₂CH₂CO | 4 | >300 | L |
| 126 | COOH | H | t-Boc | H | COOCH₂C₆H₄-2-Cl | 4 | >200 | L |
| 127 | COOH | H | t-Boc | H | COOCH₂C₆H₄-2-Cl | 3 | >200 | D |
| 128 | COOH | H | t-Boc | H | t-Boc | 4 | 28,000 | L |
| 129 | COOH | H | Fmoc | H | COOCH₂CH₂CH₂CO | 4 | 20,000 | L |
| 130 | COOH | H | Fmoc | H | Ac | 4 | 56,000 | L |
| 131 | COOH | H | Fmoc | H | 2-NH₂C₆H₄CH₂CH₂CO | 4 | 8,400 | D |
| 132 | COOH | H | Fmoc | H | Fmoc | 4 | 16,000 | L |
| 133 | COOH | H | COOCH₂C₆H₅ | H | COOCH₂C₆H₅ | 4 | >200,000 | D |
| 134 | COOH | H | COOCH₂C₆H₅ | H | t-Boc | 4 | >200,000 | L |
| 135 | COOH | H | COOCH₂C₆H₅ | H | COOCH₂C₆H₅ | 3 | >200,000 | L |
| 136 | COOH | H | COOCH₂C₆H₅ | H | t-Boc | 4 | >200,000 | D |
| 137 | COOH | H | t-Boc | H | COOCH₂C₆H₅ | 3 | >200,000 | L |

TABLE 1-continued

| Compound No. | Cx | R₁ | R₂ | R₃ | R₄ | n | Ki (nM) | D, L, DL R, S, RS |
|---|---|---|---|---|---|---|---|---|
| 138 | COOH | H | t-Boc | H | Fmoc | 4 | >200 | L |
| 139 | COOH | H | Fmoc | H | 3-NO₂C₆H₄SO₂ | 4 | | L |
| 140 | COOH | H | Fmoc | H | 4-t-BuC₆H₄SO₂ | 4 | | L |
| 141 | CONHOH | i-C₄H₉ | 4-CH₃C₆H₄SO₂ | H | Fmoc | 4 | 245 | RS |
| 142 | COOH | H | Fmoc | H | 4-CH₃C₆H₄SO₂ | 4 | 9,400 | D |
| 143 | COOH | H | t-Boc | H | 4-BrC₆H₄SO₂ | 4 | 660,000 | L |
| 144 | COOH | H | Fmoc | H | H | 3 | | L |
| 145 | COOH | H | Fmoc | H | H | 4 | | L |
| 146 | COOH | H | Fmoc | H | 3-NO₂C₆H₄SO₂ | 3 | | L |
| 147 | COOH | H | Fmoc | H | 4-BrC₆H₄SO₂ | 3 | | L |
| 148 | COOH | H | Fmoc | H | 4-CH₃OC₆H₄SO₂ | 3 | | L |
| 149 | COOH | H | Fmoc | H | 4-CH₃C₆H₄SO₂ | 3 | 10,100 | L |
| 150 | COOH | H | Fmoc | H | 4-FC₆H₄SO₂ | 3 | | L |
| 151 | COOH | H | 4-CH₃C₆H₄SO₂ | H | 4-CH₃C₆H₄SO₂ | 4 | | L |
| 152 | COOH | i-C₄H₉ | 4-CH₃C₆H₄SO₂ | H | Fmoc | 4 | 151 | DL |
| 153 | COOH | i-C₄H₉ | 4-NO₂C₆H₄SO₂ | H | C₆H₅CH₂CH₂CS | 4 | 10.2 | L |
| 154 | COOH | i-C₄H₉ | 4-NO₂CBH₄SO₂ | H | C₆H₅SCH₂CO | 4 | 15.7 | L |
| 155 | COOH | i-C₄H₉ | 4-NH₂C₆H₄SO₂ | H | 3,4-(OCH₂O)C₆H₃CH₂CH₂CO | 4 | 16.7 | L |
| 156 | COOH | i-C₄H₉ | 4-NH₂C₆H₄SO₂ | H | 3-CH₃OC₆H₄CH₂CH₂CO | 4 | 18.9 | L |
| 157 | COOH | i-C₄H₉ | 4-NH₂C₆H₄SO₂ | H | 2-CH₃OC₆H₄CH₂CH₂CO | 3 | | L |
| 158 | COOH | i-C₄H₉ | 4-CH₃C₆H₄SO₂ | H | C₆H₅CH₂CH₂CO | 4 | >300 | L |
| 159 | COOH | i-C₄H₉ | 4-NO₂C₆H₄SO₂ | i-C₄H₉ | C₆H₅CH₂CH₂CO | 4 | >300 | DL |
| 160 | COOH | i-C₄H₉ | 4-NO₂C₆H₄SO₂ | H | C₆H₅OCH₂CO | 4 | 24.5 | L |
| 161 | COOH | i-C₄H₉ | 4-NO₂C₆H₄SO₂ | H | 2-CH₃OC₆H₄CH=CHCO (trans) | 4 | >300 | L |
| 162 | COOH | i-C₄H₉ | 4-NO₂C₆H₄SO₂ | H | 3-CH₃OC₆H₄CH=CHCO | 4 | >300 | L |
| 163 | COOH | i-C₄H₉ | 4-NO₂C₆H₄SO₂ | H | 3,4-(OCH₂O)C₆H₃CH=CHOC | 4 | >300 | L |
| 164 | COOH | i-C₄H₉ | 4-CH₃CSH₄SO₂ | H | 3-C₅H₄NCH=CHCO (trans) | 4 | >300 | L |
| 165 | CONHOH | i-C₄H₉ | 4-FC₆H₄SO₂ | H | Fmoc | 4 | | L |
| 166 | COOH | H | Fmoc | H | 4-FC₆H₄SO₂ | 4 | | L |
| 167 | COOH | H | Fmoc | H | 2-FC₆H₄SO₂ | 4 | | L |
| 168 | COOH | H | Fmoc | H | 1-naphthyl-SO₂ | 3 | | L |
| 169 | COOCH₂C₆H₅ | i-C₄H₉ | C₆H₅SO₂ | H | COOCH₂C₆H₅ | 4 | | L |
| 170 | COOCH₂C₆H₅ | Et₂CHCH₂ | 4-CH₃OC₆H₄SO₂ | H | COOCH₂C₆H₅ | 4 | | L |
| 171 | COOCH₂C₆H₅ | Et₂CHCH₂ | 4-BrC₆H₄SO₂ | H | COOCH₂C₆H₅ | 4 | | L |
| 172 | COOCH₂C₆H₅ | i-C₄H₉ | 2-NO₂C₆H₄SO₂ | H | COOCH₂C₆H₅ | 4 | | L |
| 173 | COOCH₂C₆H₅ | Et₂CHCH₂ | C₆H₅SO₂ | H | COOCH₂C₆H₅ | 4 | | L |
| 174 | COOCH₂C₆H₅ | Et₂CHCH₂ | 4-CH₃OC₆H₄SO₂ | H | COOCH₂C₆H₅ | 4 | | L |
| 175 | COOCH₂C₆H₅ | Et₂CHCH₂ | C₆H₅CH=CHSO₂ | H | COOCH₂C₆H₅ | 4 | | L |
| 176 | COOCH₂C₆H₅ | Et₂CHCH₂ | 4-AcNHC₆H₄SO₂ | H | COOCH₂C₆H₅ | 4 | | L |
| 177 | COOCH₂C₆H₅ | Et₂CHCH₂ | 4-BrC₆H₄SO₂ | H | COOCH₂C₆H₅ | 4 | | L |
| 178 | COOCH₂C₆H₅ | Et₂CHCH₂ | 4-NO₂C₆H₄SO₂ | H | COOCH₂C₆H₅ | 4 | | L |
| 179 | COOCH₂C₆H₅ | MeEtCHCH₂ | C₆H₅SO₂ | H | COOCH₂C₆H₅ | 4 | | L |
| 180 | COOCH₂C₆H₅ | MeEtCHCH₂ | 4-CH₃OC₆H₄SO₂ | H | COOCH₂C₆H₅ | 4 | | L |
| 181 | COOCH₂C₆H₅ | MeEtCHCH₂ | C₆H₅CH=CHSO₂ | H | COOCH₂C₆H₅ | 4 | | L |
| 182 | COOCH₂C₆H₅ | MeEtCHCH₂ | 4-AcNHC₆H₄SO₂ | H | COOCH₂C₆H₅ | 4 | | L |
| 183 | COOCH₂C₆H₅ | MeEtCHCH₂ | 4-BrC₆H₄SO₂ | H | COOCH₂C₆H₅ | 4 | | L |

TABLE 1-continued

| Compound No. | Cx | R₁ | R₂ | R₃ | R₄ | n | Ki (nM) | D, L, DL R, S, RS |
|---|---|---|---|---|---|---|---|---|
| 184 | COOCH₂C₆H₅ | MeEtCHCH₂ | 4-NO₂C₆H₄SO₂ | H | COOCH₂C₆H₅ | 4 | | L |
| 185 | COOCH₂C₆H₅ | MeEtCHCH₂ | 2-NO₂C₆H₄SO₂ | H | COOCH₂C₆H₅ | 4 | | L |
| 186 | COOH | i-C₄H₉ | 4-NO₂C₆H₄SO₂ | H | 2-CH₃OC₆H₄CH=CHCO (cis) | 4 | 39.8 | L |
| 187 | COOH | i-C₄H₉ | 4-NO₂C₆H₄SO₂ | H | C₆H₅CH₂CH=CHCO (trans) | 4 | | L |
| 188 | COOH | i-C₄H₉ | 4-CH₃C₆H₄SO₂ | H | 4-HOC₆H₄CH=CHCO (trans) | 4 | | L |
| 189 | COOH | i-C₄H₉ | 4-NO₂C₆H₄SO₂ | H | 3,5-(CH₃O)₂C₆H₃CH=CHCO | 4 | 108 | L |
| 190 | COOH | i-C₄H₉ | 4-NO₂C₆H₄SO₂ | H | 2,5-(CH₃O)₂C₆H₃CH=CHCO | 4 | >75 | L |
| 191 | COOH | i-C₄H₉ | 4-NO₂C₆H₄SO₂ | H | 2,4-(CH₃O)₂C₆H₃CH=CHCO | 4 | >75 | L |
| 192 | COOH | i-C₄H₉ | 4-NH₂C₆H₄SO₂ | H | C₆H₅OCH₂CO | 4 | 8.2 | L |
| 193 | COOH | i-C₄H₉ | 4-NO₂C₆H₄SO₂ | H | 3,4-(CH₃O)₂C₆H₃CH=CHCO | 4 | >75 | L |
| 194 | COOH | i-C₄H₉ | 4-NH₂C₆H₄SO₂ | H | 4-NH₂C₆H₄CH₂CH₂CO | 4 | >300 | L |
| 195 | COOH | i-C₄H₉ | 4-NH₂C₆H₄SO₂ | H | 3-C₅H₃NCH₂CH₂CO | 4 | >300 | L |
| 196 | COOH | i-C₄H₉ | 4-NH₂C₆H₄SO₂ | H | 2,4-(CH₃O)₂C₆H₃CH₂CH₂CO | 4 | 17.1 | L |
| 197 | COOH | i-C₄H₉ | 4-NH₂C₆H₄SO₂ | H | 2,5-(CH₃O)₂C₆H₃CH₂CH₂CO | 4 | 20.7 | L |
| 198 | COOH | i-C₄H₉ | 4-NH₂C₆H₄SO₂ | H | 3,5-(CH₃O)₂C₆H₃CH₂CH₂CO | 4 | 32.2 | L |
| 199 | COOH | i-C₄H₉ | 4-NO₂C₆H₄SO₂ | H | 4-CH₃C₆H₄SO₂ | 4 | | L |
| 200 | COOH | i-C₄H₉ | 4-NH₂C₆H₄SO₂ | H | 3,4-(CH₃O)₂C₆H₃CH₂CH₂CO | 4 | 132 | L |
| 201 | COOH | i-C₄H₉ | 4-CH₃C₆H₄SO₂ | H | 2,3-(CH₃O)₂C₆H₃CH₂CH₂CO | 4 | 15.0 | L |
| 202 | COOH | i-C₄H₉ | 4-CH₃C₆H₄SO₂ | H | C₆H₅OCH₂CO | 4 | 18.0 | L |
| 203 | COOH | i-C₄H₉ | 4-CH₃C₆H₄SO₂ | H | C₆H₅SCH₂CO | 4 | 17.5 | L |
| 204 | COOH | i-C₄H₉ | 4-CH₃C₆H₄SO₂ | H | C₆H₅CH₂CH₂C=N—CN | 4 | 34.0 | DL |

TABLE 2

| Compound No. | Cx | $R_1$ | $R_2$ | $R_3$ | $R_4$ | XX | Ki (nM) R, S, RS |
|---|---|---|---|---|---|---|---|
| 205 | COOH | i-$C_4H_9$ | 4-$CH_3C_6H_4SO_2$ | H | $COCH_2CH_2C_5H_5$ | O | DL |
| 206 | COOH | i-$C_4H_9$ | 4-$CH_3C_6H_4SO_2$ | H | $COCH_2CH_2C_5H_5$ | NH | >300 DL |
| 207 | COOH | i-$C_4H_9$ | 4-$CH_3C_6H_4SO_2$ | H | $COCH_2CH_2C_5H_5$ | S | DL |

In the description herein, the following abbreviations are used:

| Abbreviation | Meaning |
|---|---|
| AcOH | Acetic acid |
| ARC | AIDS-related complex |
| AIDS | Acquired Immunodeficiency Syndrome |
| AZT | 3-Azido-3-deoxythymine (Zidovudine) |
| Boc | tert-Butoxycarbonyl |
| BOP | 1-Benzotriazolyloxy-tris-dimethylamino-phosphonium hexafluorophosphate |
| BSA | Bovine serum albumin |
| i-Bu | iso-Butyl |
| Cbz | Benzyloxycarbonyl |
| 2-ClCbz | 2-Chlorobenzyloxycarbonyl |
| DABCYL | 4-[[4'-(dimethylamino)phenyl]azo]benzoic acid |
| DEAD | Diethyl azodicarboxylate |
| DIEA | N,N-Diisopropylethylamine |
| DMF | Dimethylformamide |
| DNA | Deoxyribose nucleic acid |
| DTT | Dithiothreitol |
| EDANS | 5-[(2'-aminoethyl)amino]naphthalene sulfonic acid |
| EDC | 1-Ethyl-3-(3-dimethylaminopropyl)carbodiimide hydrochloride |
| EDTA | Ethylenediaminetetraacetic acid |
| EtOAc | Ethyl acetate |
| EtOH | Ethyl alcohol |
| Fmoc | 9-Fluorenylmethoxycarbonyl |
| g | gram |
| HIV-1, -2 | Human immunodeficiency virus type 1, type 2 |
| HTLV-I, -II | Human T-cell lymphotropic virus type I, type II |
| IL-2 | Interleukine-2 |
| LC-MS | liquid chromotography-mass spectrometry |
| M | Molar |
| MeOH | Methyl alcohol |
| mg | Milligram |
| MP | Melting point |
| min | Minute |
| mL | Milliliter |
| mmol | Millimole |
| nM | Nanomolar |
| rEPO | Recombinant erythropoietin |
| RNA | Ribose nucleic acid |
| 3TC | 2',3'-Dideoxy-3-thiacytidine |
| TFA | Trifluoroacetic acid |
| THF | Tetrahydrofuran |
| Za | Benzyloxycarbonyl |

In order that this invention be more fully understood, the following examples are set forth relating to the preparation of example compounds in accordance with the present invention. These examples are for the purpose of illustration only and are not to be construed as limiting the scope of the invention in any way. When an example relates to the preparation of a compound identified in Table 1 or 2 above, the compound number used in Table 1 or 2 will appear after the name of the compound prepared in accordance to the example, additionally with respect to the compound numbers used in the tables of examples 80, and 81 these numbers identify the compounds as the compounds corresponding to that respective number which appears in Table 1.

Materials and Methods

Analytical thin layer chromatography (TLC) was carried out with 0.25 mm silica gel E. Merck 60 $F_{254}$ plates and eluted with the indicated solvent systems. Preparative chromatography was performed either by flash chromatography, using Silica Gel 60 (EM Science) with the indicated solvent systems and a positive nitrogen pressure to allow proper elution, or by preparative thin layer chromatography, again employing E. Merck 60 $F_{254}$ plates of 0.5, 1.0, or 2.0 mm thickness. Detection of the compounds was carried out by exposing eluted plates, analytical or preparative, to UV light and treating analytical plates either with a 2% p-anisaldehyde solution in ethanol containing 1% acetic acid and 3% sulfuric acid or with a 0.3% ninhydrin solution in ethanol containing 3% acetic acid, followed by heating.

Nuclear magnetic resonance (NMR) spectra were recorded on a Bruker AMX-2 500 MHz equipped with a reversed QNP probe. Samples were dissolved in deuterochloroform ($CDCl_3$), deuteroacetone (acetone-$d_6$) or deuterated dimethylsulfoxide (DMSO-$d_6$) for data acquisition using tetramethylsilane (TMS) as internal standard. Chemical shifts are expressed in parts per million (ppm), the coupling constants J are expressed in hertz (Hz) and multiplicities (denoted as s for singlet, d for doublet, dd for doublet of doublets, t for triplet, q for quartet, m for multiplet, and br s for broad singlet).

The following compounds were prepared either from a derivative of a L-amino acid or, when indicated, from a derivative of a D-amino acid using the procedures summarized in Schemes 1, 2, 3, 4, 4a, 5, 5a, 6 or 7.

EXAMPLE 1

Preparation of Nα-(9-Fluorenylmethoxycarbonyl)-L-lysine (Compound No. 145)

Nα-(9-fluorenylmethoxycarbonyl)-Nε-benzyloxycarbonyl-L-lysine (502 mg, 1.00 mmol) was dissolved in TFA/$CH_2Cl_2$ (3 mL/3 mL) and stirred at room temperature for 1 h. The volatiles were removed in vacuo to afford the title compound quantitatively as a white solid.

$^1$H NMR (DMSO-$d_6$): 1.30–1.43 (m, 2H), 1.50–1.78 (m, 6H), 2.78 (d, J=5.5, 2H), 3.94 (m, 1H), 4.22 (m, 1H), 4.25–4.33 (m, 2H), 7.31 (dd, J=7.4, 7.4, 2H), 7.40 (dd, J=7.5, 7.4, 2H), 7.61 (d, J=7.7, 1H), 7.71 (m, 2H), 7.82 (br s, 3H), 7.88 (d, J=7.5, 2H).

The D-isomer was obtained by using Nα-(9-fluorenylmethoxycarbonyl)-Nε-benzyloxycarbonyl-D-lysine.

EXAMPLE 2

Preparation of Nε-(4-Bromobenzenesulfonyl)-Nα-(9-fluorenylmethoxycarbonyl)-L-lysine (Compound No. 16)

The product of example 1 (368 mg, 1.00 mmol) was dissolved in a 1M aqueous $K_2CO_3$ solution (5 mL) and THF (3 mL). The reaction mixture was cooled to 0° C., before a solution of 4-bromobenzenesulfonyl chloride (280 mg; 1.10 mmol) in dioxane (6 mL) was added. The mixture was stirred at 0° C. for 1 h and then at room temperature for 2 h. The pH of the reaction mixture was acidified (pH~3) with 1N HCl. The mixture was then extracted with EtOAc. The organic layer was washed with brine and dried over MgSO$_4$. After filtration, the filtrate was evaporated to dryness in vacuo, and the crude material was purified by flash chromatography eluting with 70% EtOAc in hexane containing 0.4% AcOH, to yield 417 mg (71%) of the title compound.

$^1$H NMR (DMSO-d$_6$): 1.20–1.80 (m, 6H), 2.70 (dd, J=12.8, 6.5, 2H), 3.88–3.92 (m, 1H), 4.20 (t, J=7.0, 1H), 4.30 (d, J=7.0, 2H), 7.20–7.40 (m, 5H), 7.55–7.60 (m, 1H), 7.67–7.92 (m, 8H), 12.50 (br s, 1H).

Utilising the D-isomer and following the indications of example 2, the D isomer was obtained.

EXAMPLE 3

Preparation of Nε-(4-Nitrobenzenesulfonyl)-Nα-(9-fluorenylmethoxycarbonyl)-L-lysine (Compound No. 50)

Nα-(9-fluorenylmethoxycarbonyl)-L-lysine was reacted with 4-nitrobenzenesulfonyl chloride under the conditions used in example 2 giving 89% of the title compound.

$^1$H NMR (DMSO-d$_6$): 1.22–1.65 (m, 6H), 2.79 (dd, J=12.8, 6.2, 2H), 3.85 (m, 1H), 4.20 (t, J=7.0, 1H), 4.28 (d, J=7.0, 2H), 7.28–7.42 (m, 4H), 7.56 (d, J=8.1, 2H), 7.70 (d, J=6.3, 2H), 7.88 (d, J=7.4, 2H), 7.98 (t, J=5.4, 1H), 8.03 (d, J=8.5, 2H), 8.40 (d, J=8.4, 2H), 12.40 (br, 1H).

EXAMPLE 4

Preparation of Nε-(4-Aminobenzenesulfonyl)-Nα-(9-fluorenylmethoxycarbonyl)-L-lysine (Compound No. 52)

The product obtained from example 3 (553 mg, 1.00 mmol) was dissolved in EtOAc (10 mL) and then hydrogenated using 10% Pd on charcoal as catalyst at atmospheric pressure for 2 h. The catalyst was filtered off and the filtrate was evaporated in vacuo to yield the title compound in 95% yield.

$^1$H NMR (DMSO-d$_6$): 1.20–1.72 (m, 6H), 2.60 (dd, J=12.8, 6.2, 2H), 3.80 (m, 1H), 4.20 (m, 2H), 4.31 (m, 1H), 5.90 (br s, 2H), 6.61 (d, J=8.2, 2H), 7.00–7.10 (m, 2H), 7.28–7.48 (m, 6H), 7.68–7.90 (m, 4H).

EXAMPLE 5

Preparation of Nε-(4-Iodobenzenesulfonyl)-Nα-(9-fluorenylmethoxycarbonyl)-L-lysine (Compound No. 64)

Nα-(9-fluorenylmethoxycarbonyl)-L-lysine was reacted with 4-iodobenzenesulfonyl chloride under the conditions used in example 2 giving 68% of the title compound.

$^1$H NMR (DMSO-d$_6$): 1.23–1.45 (m, 4H), 1.50–1.68 (m, 2H), 2.70 (dd, J=13.0, 6.9, 2H), 3.38 (m, 1H), 4.20 (t, J=7.0, 1H), 4.30 (d, J=7.0, 2H), 7.28–7.42 (m, 4H), 7.52–7.60 (m, 1H), 7.67 (t, J=5.5, 1H), 7.70 (d, J=7.4, 2H), 7.88 (d, J=7.4, 2H), 7.97 (d, J=8.6, 2H), 11.30 (br s, 1H),

EXAMPLE 6

Preparation of Nε-(4-Fluorobenzenesulfonyl)-Nα-(9-fluorenylmethoxycarbonyl)-L-lysine (Compound No. 55)

Nα-(9-fluorenylmethoxycarbonyl)-L-lysine was reacted with 4-fluorobenzenesulfonyl chloride under the conditions used in example 2 giving 51% of the title compound.

$^1$H NMR (DMSO-d$_6$): 1.22–1.70 (m, 6H), 2.75 (dd, J=12.8, 6.2, 2H), 3.85–3.92 (m, 1H), 4.20 (t, J=7.0, 1H), 4.30 (d, J=7.0, 2H), 7.25–7.45 (m, 6H), 7.57 (d, J=8.3, 1H), 7.62 (t, J=5.2, 1H), 7.72 (d, J=6.5, 2H), 7.82–7.90 (m, 4H), 12.40 (br s, 1H).

EXAMPLE 7

Preparation of Nε-(2,5-Dichlorobenzenesulfonyl)-Nα-(9-fluorenylmethoxycarbonyl)-L-lysine (Compound No. 54)

Nα-(9-fluorenylmethoxycarbonyl)-L-lysine was reacted with 2,5-dichlorobenzenesulfonyl chloride under the conditions used in example 2 giving 28% of the title compound.

$^1$H NMR (DMSO-d$_6$): 1.20–1.45 (m, 6H), 1.48–1.68 (m, 2H), 2.70 (dd, J=12.8, 6.7, 2H), 3.83–3.89 (m, 1H), 4.20 (t, J=7.0, 1H), 4.28 (d, J=6.8, 2H), 7.30 (t, J=7.3, 2H), 7.40 (t, J=7.3, 2H), 7.55 (d, J=8.1, 1H), 7.62–7.65 (m, 4H), 7.78 (d, J=7.8, 2H), 7.92 (d, J=7.9, 2H).

EXAMPLE 8

Preparation of Nε-(4-Methylbenzenesulfonyl)-Nα-(9-fluorenylmethoxycarbonyl)-L-lysine (Compound No. 63)

Nα-(9-fluorenylmethoxycarbonyl)-L-lysine was reacted with 4-methylbenzenesulfonyl chloride under the conditions used in example 2 giving 71% of the title compound.

$^1$H NMR (DMSO-d$_6$): 1.20–1.75 (m, 6H), 2.35 (s, 3H), 2.70 (dd, J=12.9, 7.0, 2H), 3.82–3.90 (m, 1H), 4.20 (t, J=7.0, 1H), 4.30 (d, J=7.0, 2H), 7.20–7.50 (m, 7H), 7.52–7.90 (m, 7H), 12.30 (br s, 1H).

The D-isomer was prepared by following essentially the same conditions.

EXAMPLE 9

Preparation of Nε-(3-Nitrobenzenesulfonyl)-Nα-(9-fluorenylmethoxycarbonyl)-L-lysine (Compound No. 139)

Nα-(9-fluorenylmethoxycarbonyl)-L-lysine was reacted with 3-nitrobenzenesulfonyl chloride under the conditions used in example 2 giving 42% of the title compound.

$^1$H NMR: 1.3–1.7 (m, 6H), 2.76 (m, 2H), 3.76 (m, 1H), 4.0–4.5 (m, 1H), 4.22 (m, 2H), 4.32 (m, 1H), 6.3–7.0 (m, 1H), 7.9–8.2 (m, 1H), 7.2–8.6 (m, 12H).

EXAMPLE 10

Preparation of Nε-(4-Methoxybenzenesulfonyl)-Nα-(9-fluorenylmethoxycarbonyl)-L-lysine (Compound No. 61)

Nα-(9-fluorenylmethoxycarbonyl)-L-lysine was reacted with 4-methoxybenzenesulfonyl chloride under the conditions used in example 2 giving 61% of the title compound.

$^1$H NMR (DMSO-d$_6$): 1.10–1.68 (m, 6H), 2.70 (m, 2H), 3.80 (s, 3H), 3.88 (m, 1H), 4.20 (t, J=7.0, 1H), 4.28 (t, J=7.0, 2H), 7.08 (d, J=8.3, 2H), 7.30–7.45 (m, 4H), 7.60 (d, J=7.7, 1H), 7.70 (m, 2H), 7.90 (d, J=7.4, 2H), 12.50 (br s, 1H).

EXAMPLE 11

Preparation of Nε-(2,4,6-Triisopropylbenzenesulfonyl)-Nα-(9-fluorenylmethoxycarbonyl)-L-lysine (Compound No. 25)

Nα-(9-fluorenylmethoxycarbonyl)-L-lysine was reacted with 2,4,6-triisopropylbenzenesulfonyl chloride under the conditions used in example 2 giving 34% of the title compound.

¹H NMR (DMSO-d₆): 1.17 (d, J=6.0, 6H), 1.20 (d, J=6.8, 12H), 1.22–1.65 (m, 6H), 2.78 (dd, J=13.0, 6.9, 2H), 2.90 (h, J=6.5, 1H), 3.85 (m, 1H), 4.13 (h, J=7.0, 1H), 4.27 (d, J=7.0, 2H), 7.21 (s, 2H), 7.29–7.40 (m, 4H), 7.44 (t, J=5.3, 1H), 7.53 (d, J=7.7, 1H), 7.70 (m, 2H), 7.88 (d, J=7.4, 2H), 12.20 (br s, 1H).

EXAMPLE 12

Preparation of Nε-(2,4,6-Trimethylbenzenesulfonyl)-Nα-(9-fluorenylmethoxycarbonyl)-L-lysine (Compound No. 27)

Nα-(9-fluorenylmethoxycarbonyl)-L-lysine was reacted with 2,4,6-trimethylbenzenesulfonyl chloride under the conditions used in example 2 giving 37% of the title compound.

¹H NMR (DMSO-d₆): 1.22–1.45 (m, 4H), 1.50–1.70 (m, 2H), 2.24 (s, 3H), 2.56 (s, 6H), 2.74 (dd, J=13.0, 6.9, 2H), 3.90 (m, 1H), 4.23 (t, J=7.0, 1H), 4.30 (d, J=7.0, 2H), 7.00 (s, 2H), 7.29–7.45 (m, 6H), 7.71 (m, 2H), 7.88 (d, J=7.5, 2H), 12.30 (br s, 1H).

Also isolated in small yield (25%) from the reaction mixture was Nα-(9-fluorenylmethoxycarbonyl)-L-lysyl-Nα-(9-fluorenylmethoxycarbonyl)-Nε-(2,4,6-trimethylbenzenesulfonyl)-L-lysine (Compound No. 26).

¹H NMR (DMSO-d₆): 1.10–1.75 (m, 12H), 2.22 (s, 3H), 2.52 (s, 6H), 2.68 (m, 2H), 3.02 (m, 2H), 3.82 (m, 1H), 3.90 (m, 1H), 4.20 (m, 2H), 4.28 (m, 4H), 6.98 (s, 2H), 7.28–7.42 (m, 1H), 7.57 (d, J=7.5, 2H), 7.70 (m, 4H), 7.80 (t, J=5,0 1H), 7.89 (d, J=7.3, 4H), 12.20 (br s, 1H).

EXAMPLE 13

Preparation of Nε-(4-tert-Butylbenzenesulfonyl)-Nα-(9-fluorenylmethoxycarbonyl)-L-lysine (Compound No. 140)

Nα-(9-fluorenylmethoxycarbonyl)-L-lysine was reacted with 4-tert-butylbenzenesulfonyl chloride under the conditions used in example 2 giving 72% of the title compound.

¹H NM (DMSO-d₆): 1.20–1.45 (m, 4H), 1.29 (s, 9H), 1.50–1.65 (m, 2H), 2.70 (dd, J=13.0, 6.9, 2H), 3.85 (m, 1H), 4.22 (t, J=7.0, 1H), 4.28 (d, J=7.5, 2H), 4.47 (t, J=5.5, 1H), 7.28–7.43 (m, 6H), 7.55 (d, J=8.2, 2H), 7.60 (d, J=8.5, 2H), 7.70 (d, J=7.0, 2H), 7.88 (d, J=7.3, 2H), 12.30 (br s, 1H).

EXAMPLE 14

Preparation of Nε-Benzenesulfonyl-Nα-(9-fluorenylmethoxycarbonyl)-L-lysine (Compound No. 49)

Nα-(9-fluorenylmethoxycarbonyl)-L-lysine was reacted with benzenesulfonyl chloride under the conditions used in example 2 giving 68% of the title compound.

¹H NMR (DMSO-d₆): 1.15–1.45 (m, 4H), 1.50–1.65 (m, 2H), 2.70 (m, 1H), 3.77 (m, 1H), 4.20 (t, J=7.0, 1H), 4.28 (t, J=7.0, 2H), 7.30–7.80 (m, 15H), 12.70 (br s, 1H).

EXAMPLE 15

Preparation of Nε-(3-Trifluoromethylbenzenesulfonyl)-Nα-(9-fluorenylmethoxycarbonyl)-L-lysine (Compound No. 34)

Nα-(9-fluorenylmethoxycarbonyl)-L-lysine was reacted with 3-trifluoromethylbenzenesulfonyl chloride under the conditions used in example 2 giving 61% of the title compound.

¹H NMR (DMSO-d₆): 1.20–1.68 (m, 6H), 2.75 (dd, J=12.8, 6.8, 2H), 3.87 (m, 1H), 4.21 (t, J=7.0, 1H), 4.28 (d, J=7.0, 2H), 7.30–7.42 (m, 4H), 7.52 (d, J=7.8, 1H), 7.70 (d, J=6.4, 2H), 7.80–7.90 (m, 4H), 8.02–8.10 (m, 3H), 12.50 (br s, 1H).

EXAMPLE 16

Preparation of Nε-(1-Naphthalenesulfonyl)-Nα-(9-fluorenylmethoxycarbonyl)-L-lysine (Compound No. 31)

Nα-(9-fluorenylmethoxycarbonyl)-L-lysine was reacted with 1-naphthalenesulfonyl chloride under the conditions used in example 2 giving 66% of the title compound.

¹H NMR (DMSO-d₆): 1.18–1.60 (m, 6H), 2.75 (dd, J=13.0, 7.0, 2H), 3.80 (m, 1H), 4.21 (t, J=7.0, 1H), 4.27 (d, J=7.0, 2H), 7.28–7.40 (m, 4H), 7.51 (d, J=7.7, 1H), 7.61–7.71 (m, 5H), 7.86 (d, J=7.1, 2H), 7.91 (t, J=5.2, 1H), 8.06 (d, J=8.2, 1H), 8.11 (d, J=7.3, 1H), 8.20 (d, J=8.3, 1H), 8.66 (d, J=8.5, 1H), 12.30 (br s, 1H).

EXAMPLE 17

Preparation of Nε-(2-Naphthalenesulfonyl)-Nα-(9-fluorenylmethoxycarbonyl)-L-lysine (Compound No. 32)

Nα-(9-fluorenylmethoxycarbonyl)-L-lysine was reacted with 2-naphthalenesulfonyl chloride under the conditions used in example 2 giving 71% of the title compound.

¹H NMR (DMSO-d₆): 1.25–1.60 (m, 6H), 2.74 (dd, J=12.6, 6.5, 2H), 3.85 (m, 1H), 4.19 (t, J=6.9, 1H), 4.28 (d, J=7.0, 2H), 7.25–7.40 (m, 4H), 7.53 (d, J=8.2, 1H), 7.64–7.87 (m, 7H), 8.00–8.20 (m, 3H), 8.42 (s, 1H), 12.50 (br s, 1H).

EXAMPLE 18

Preparation of Nε-(8-Quinolinesulfonyl)-Nα-(9-fluorenylmethoxycarbonyl)-L-lysine (Compound No. 28)

Nα-(9-fluorenylmethoxycarbonyl)-L-lysine was reacted with 8-quinolinesulfonyl chloride under the conditions used in example 2 giving 81% of the title compound.

¹H NMR (DMSO-d₆): 1.20–1.52 (m, 6H), 2.70 (dd, J=12.9, 6.9, 2H), 3.38 (m, 1H), 4.20 (t, J=6.9, 1H), 4.30 (d, J=7.0, 2H), 7.15 (t, J=5.6, 1H), 7.28–7.40 (m, 4H), 7.50 (d, J=7.6 1H), 7.68–7.76 (m, 6H), 8.28 (dd, J=13.0, 8.0, 2H), 8.53 (d, J=8.3, 1H), 9.05 (d, J=3.0, 1H), 12.30 (br s, 1H).

EXAMPLE 19

Preparation of Nε-Phenylmethylsulfonyl-Nα-(9-fluorenylmethoxycarbonyl)-L-lysine (Compound No. 33)

Nα-(9-fluorenylmethoxycarbonyl)-L-lysine was reacted with phenylmethylsulfonyl chloride under the conditions used in example 2 giving 15% of the title compound.

¹H NMR (DMSO-d₆): 1.20–1.80 (m, 6H), 2.86 (dd, J=12.5, 6.5, 2H), 3.90 (m, 1H), 4.20 (t, J=7.0, 1H), 4.26 (d, J=7.0, 2H), 4.29 (s, 2H), 7.28–7.45 (m, 9H), 7.60 (d, J=8.3, 1H), 7.72 (d, J=7.4, 2H), 7.89 (d, J=7.4, 2H), 12.50 (br s, 1H).

EXAMPLE 20

Preparation of Nε-(1S)-(10-Camphorsulfonyl)-Nα-(9-fluorenylmethoxycarbonyl)-L-lysine (Compound No. 35)

Nα-(9-fluorenylmethoxycarbonyl)-L-lysine was reacted with (1S)-(+)-10-camphorsulfonyl chloride under the conditions used in example 2 giving 72% of the title compound.

¹H NMR (DMSO-d₆): 0.80 (s, 3H), 1.00 (s, 3H), 1.30–1.78 (m, 7H), 1.88–1.92 (m, 2H), 2.05 (m, 1H), 2.30–2.42 (m, 2H), 2.87 (d, J=14.9, 2H), 2.90–3.03 (m, 2H), 3.31 (s, 2H), 3.90 (m, 1H), 4.20 (t, J=7.0, 1H), 4.30 (d, J=7.0, 2H), 7.00 (t, J=5.3, 1H), 7.28–7.45 (m, 4H), 7.60 (d, J=7.9, 1H), 7.70 (d, J=7.3, 2H), 7.89 (d, J=7.4, 2H), 12.50 (br s, 1H).

EXAMPLE 21

Preparation of Nα-(2-Nitrobenzenesulfonyl)-Nε-(9-fluorenylmethoxycarbonyl)-L-lysine (Compound No. 70)

Nα-(9-fluorenylmethoxycarbonyl)-L-lysine was reacted with 2-nitrobenzenesulfonyl chloride under the conditions used in example 2 giving 44% of the title compound.

¹H NMR (DMSO-d₆): 1.18–1.40 (m, 4H), 1.52–1.73 (m, 2H), 2.90 (m, 2H), 3.82 (m, 1H), 4.20 (t, J=6.3, 1H), 4.28 (d, J=7.0, 1H), 7.22 (t, J=5.2, 1H), 7.31–7.45 (m, 4H), 7.67 (d, J=7.3, 1H), 7.80–8.08 (m, 6H), 8.45 (d, J=8.4, 1H).

EXAMPLE 22

Preparation of Nε-(4-Chlorobenzenesulfonyl)-Nα-(9-fluorenylmethoxycarbonyl)-L-lysine (Compound No. 53)

Nα-(9-fluorenylmethoxycarbonyl)-L-lysine was reacted with 4-chlorobenzenesulfonyl chloride under the conditions used in example 2 giving 37% of the title compound.

¹H NMR (DMSO-d₆): 1.20–1.70 (m, 6H), 2.72 (dd, J=13.5, 6.8, 2H), 3.85 (m, 1H), 4.21 (t, J=7.0, 1H), 4.27 (d, J=7.1, 2H), 7.25–7.42 (m, 4H), 7.56 (d, J=8.1, 1H), 7.63–7.67 (m, 5H), 7.78 (d, J=7.8, 2H), 7.88 (d, J=7.5, 2H), 12.50 (br s, 1H).

EXAMPLE 23

Preparation of Nε-(2-Bromobenzenesulfonyl)-Nα-(9-fluorenylmethoxycarbonyl)-L-lysine (Compound No. 24)

Nα-(9-fluorenylmethoxycarbonyl)-L-lysine was reacted with 2-bromobenzenesulfonyl chloride under the conditions used in example 2 giving 61% of the title compound.

¹H NMR (DMSO-d₆): 1.20–1.70 (m, 6H), 2.80 (dd, J=12.8, 6.9, 2H), 3.80 (m, 1H), 4.20 (t, J=7.0, 1H), 4.28 (d, J=6.9, 2H), 7.30–7.57 (m, 7H), 7.66–7.88 (m, 6H), 7.98 (d, J=7.5, 1H).

EXAMPLE 24

Preparation of Nα-(9-Fluorenylmethoxycarbonyl)-L-ornithine Trifluoroacetate Salt (Compound No. 144)

Nα-(9-fluorenylmethoxycarbonyl)-N-δ-tert-butoxycarbonyl-L-ornithine (454 mg, 1.00 mmol) was reacted under the conditions used in example 1 to afford the title compound quantitatively as a white solid.

¹H NMR (DMSO-d₆): 1.60–1.86 (m, 4H), 2.80 (m, 2H), 4.00 (m, 1H), 4.20–4.38 (m, 3H), 7.30 (t, J=7.4, 2H), 7.40 (t, J=7.3, 2H), 7.68 (d, J=8.1, 1H), 7.72 (d, J=7.4, 2H), 7.80 (br s, 2H), 7.90 (d, J=7.4, 2H).

EXAMPLE 25

Preparation of Nδ-(3-Nitrobenzenesulfonyl)-Nα-(9-fluorenylmethoxycarbonyl)-L-ornithine (Compound No. 146)

The product of example 24 was reacted with 3-nitrobenzenesulfonyl chloride under the conditions of example 2 giving 64% of the title compound.

¹H NMR (DMSO-d₆): 1.3–1.8 (m, 4H), 2.76 (t, 2H, J=7 Hz), 3.71 (d, 1H), 4.19 (m, 2H), 4.28 (m, 1H), 6.2–7.8 (m, 1H), 7.5–8.2 (m, 1H), 7.3–8.6 (m, 12H).

EXAMPLE 26

Preparation of Nδ-(4-Bromosulfonyl)-Nα-(9-fluorenylmethoxycarbonyl)-L-ornithine (Compound No. 147)

The product of example 24 was reacted with 4-bromobenzenesulfonyl chloride under the conditions of example 2 giving 67% of the title compound.

¹H NMR (DMSO-d₆): 1.38–1.62 (m, 3H), 1.65–1.80 (m, 1H), 2.75 (dd, J=13.0, 6.9, 2H), 3.78 (m, 1H), 4.21 (t, J=6.9, 1H), 4.27 (d, J=6.9, 2H), 7.30–7.43 (m, 4H), 7.58 (d, J=7.7, 1H), 7.71 (m, 4H), 7.79 (d, J=8.1, 2H), 7.89 (d, J=7.3, 2H), 12.30 (br s, 1H).

EXAMPLE 27

Preparation of Nδ-(4-Methoxybenzenesulfonyl)-Nα-(9-fluorenylmethoxycarbonyl)-L-ornithine (Compound No. 148)

The product of example 24 was reacted with 4-methoxybenzenesulfonyl chloride under the conditions of example 2 giving 61% of the title compound.

¹H NMR (DMSO-d₆): 1.40–1.62 (m, 3H), 1.68–1.78 (m, 1H), 2.70 (dd, J=13.0, 6.8, 2H), 3.81 (s, 3H), 3.86 (m, 1H), 4.21 (t, J=7.0, 1H), 4.27 (d, J=6.9, 2H), 7.08 (d, J=8.3, 2H), 7.28–7.42 (m, 4H), 7.58 (d, J=7.7, 1H), 7.70 (m, 2H), 7.89 (d, J=7.4, 2H), 12.35 (br s, 1H).

EXAMPLE 28

Preparation of Nδ-(4-Nitrobenzenesulfonyl)-Nα-(9-fluorenylmethoxycarbonyl)-L-ornithine (Compound No. 62)

The product of example 24 was reacted with 4-nitrobenzenesulfonyl chloride under the conditions of example 2 giving 71% of the title compound.

¹H NMR (DMSO-d₆): 1.42–1.65 (m, 3H), 1.68–1.70 (m, 1H), 2.80 (dd, J=12.6, 6.8, 2H), 3.85 (m, 1H), 4.21 (t, J=6.9, 1H), 4.27 (d, J=7.0, 2H), 7.30–7.45 (m, 2H), 7.60 (d, J=8.4, 1H), 7.71 (d, J=7.3, 2H), 7.88 (d, J=7.4, 2H), 8.00 (d, J=5.3, 1H), 8.03 (d, J=8.2, 2H), 8.40 (d, J=7.8, 2H), 12.40 (br s, 1H).

EXAMPLE 29

Preparation of Nδ-(4-Methylbenzenesulfonyl)-Nα-(9-fluorenylmethoxycarbonyl)-L-ornithine (Compound No. 149)

The product of example 24 was reacted with 4-methylbenzenesulfonyl chloride under the conditions of example 2 giving 71% of the title compound.

¹H NMR (DMSO-d₆): 1.30–1.80 (m, 4H), 2.33 (s, 3H), 2.71 (m, 2H), 2.90–3.2 (m, 1H), 3.82 (m, 1H), 4.21 (m, 2H), 4.31 (m, 1H), 6.40–6.90 (m, 1H), 7.50–7.70 (m, 1H), 7.20–7.90 (m, 12H).

EXAMPLE 30

Preparation of Nδ-(4-Fluorobenzenesulfonyl)-Nα-(9-fluorenylmethoxycarbonyl)-L-ornithine (Compound No. 150)

The product of example 24 was reacted with 4-fluorobenzenesulfonyl chloride under the conditions of example 2 giving 46% of the title compound.

¹H NMR (DMSO-d₆): 1.3–1.8 (m, 4H), 2.71 (m, 2H), 3.77 (m, 1H), 4.22 (m, 2H), 4.27 (m, 1H), 6.4–7.1 (m, 1H), 7.5–8.2 (m, 1H), 7.3–7.9 (m, 12H).

EXAMPLE 31

Preparation of Nδ-(4-Aminobenzenesulfonyl)-Nα-(9-fluorenylmethoxycarbonyl)-L-ornithine (Compound No. 69)

The product obtained from example 28 (54.0 mg, 0.10 mmol) was dissolved in MeOH (5 mL) and then hydrogenated using 10% Pd/C as catalyst at atmospheric pressure for 1 h. The catalyst was filtered off and the filtrate was evaporated in vacuo to yield 96% of the title compound.

¹H NMR (DMSO-d₆): 1.3–1.8 (m, 4H), 2.79 (m, 2H), 3.14 (m, 1H), 5.76 (5.76 (s, 1H), 6.28 (s, 2H), 7.3–7.8 (m, 14H).

EXAMPLE 32

Preparation of Nα,Nε-di-(4-Methylbenzenesulfonyl)-L-lysine (Compound No. 151)

To a stirred solution of L-lysine dihydrochloride (1 mmol) in a mixture of THF and 1M K₂CO₃ (3 mL/3 mL) was added 4-methylbenzenesulfonyl chloride (381 mg, 2.00 mmol). The reaction mixture was stirred for 2 h and then quenched with 1N HCl and extracted twice with EtOAc. The combined organic extracts were dried over MgSO₄ and concentrated. The crude was purified by flash chromatography using hexane/EtOAc/AcOH (30:69.4/0.6) to give 75% of the desired product.

¹H NMR (DMSO-d₆): 1.05–1.30 (m, 4H), 1.32–1.52 (m, 2H), 2.34 (s, 3H), 2.37 (s, 3H), 2.60 (dd, J=12.9, 6.9, 2H), 3.56 (m, 1H), 7.32 (d, J=7.9, 2H), 7.38 (d, J=8.0, 2H), 7.42 (t, J=5.9, 1H), 7.62 (d, J=8.3, 2H), 7.66 (d, J=8.5, 2H), 7.97 (d, J=7.7, 1H), 12.4 (br s, 1H).

EXAMPLE 33

Preparation of Nα,Nε-di-(4-Bromobenzenesulfonyl)-L-lysine (Compound No. 17)

Following the indications of example 32 substituting 4-methylbenzenesulfonyl chloride with 4-bromobenzenesulfonyl chloride, the product was obtained in 78% yield.

¹H NMR (DMSO-d₆): 1.12–1.35 (m, 4H), 1.40–1.58 (m, 2H), 2.60–2.68 (m, 2H), 3.42–3.50 (m, 1H), 7.60–7.80 (m, 10H), 12.80 (br s, 1H).

EXAMPLE 34

Preparation of Nα,Nδ-di-(4-Bromobenzenesulfonyl)-L-ornithine (Compound No. 57)

Following the indications of example 32 substituting L-lysine with L-ornithine and using 4-bromobenzenesulfonyl chloride instead of 4-methylbenzenesulfonyl chloride, the title product was obtained in 66% yield.

¹H NMR (DMSO-d₆): 1.30–1.52 (m, 3H), 1.58–1.67 (m, 1H), 2.62–2.70 (m, 2H), 3.61–3.70 (m, 1H), 7.62–7.82 (m, 9H), 12.70 (br s, 1H).

EXAMPLE 35

Preparation of Nα-Isobutyl-Nα-(4-methylbenzenesulfonyl)-Nε-(9-fluorenylmethoxycarbonyl)-DL-lysine (Compound No. 2)

Step A. Preparation of Nε-Benzyloxycarbonyl-L-lysine Methyl Ester

To a stirred Nα-tert-butoxycarbonyl-Nε-benzyloxycarbonyl-L-lysine (7.6 g, 20 mmol) in DMF (120 mL) was added KHCO₃ (2.2 g, 22 mmol). After stirring the suspension for 1 h, methyl iodide (3.6 g, 25 mmol) was added dropwise. The reaction mixture was stirred overnight. It was quenched with 1N HCl until acidic (app. pH=3) and extracted with EtOAc. The organic layer was washed twice with brine, dried over MgSO₄ and concentrated in vacuo to afford the methyl ester that was used without further purification. It was dissolved in CH₂Cl₂ (60 mL), and to this solution was added TFA (20 mL). The reaction mixture was stirred at room temperature for 2 h, evaporated in vacuo, and taken up in 1M K₂CO₃ and EtOAc. The aqueous layer was extracted with EtOAc. The combined organic layers were dried over MgSO₄ and concentrated to give 5.42 g (92%) of the title compound as a colorless oil.

¹H NMR (CDCl₃): 1.35–1.48 (m, 2H), 1.50–1.65 (m, 3H), 1.70–1.79 (m, 1H), 1.82 (br s, 2H), 3.17 (m, 2H), 3.43 (t, J=6.5, 1H), 3.71 (s, 3H), 4.90 (br s, 1H), 5.09 (s, 2H), 7.27–7.35 (m, 5H).

Step B. Preparation of Nε-Benzyloxycarbonyl-Nα-isobutyl-L-lysine Methyl Ester

To a stirred solution of amine from step A of this example (5.0 g, 17 mmol), AcOH (2.0 mL, 42 mmol) and NaCNBH₃ (1.39 g, 22.1 mmol) in MeOH (200 mL) at 0° C. was added a solution of isobutyraldehyde (2.02 mL, 22.1 mmol) in MeOH (10 mL). The solution was warmed to room temperature and stirred for 2 h. The mixture was quenched with a saturated solution of K₂CO₃ (106 mL). The solution was filtered and the filtrate was evaporated in vacuo. The residue was taken up in EtOAc (200 mL) and water (150 mL). The organic layer was separated, washed successively with 1M K₂CO₃ and brine, dried over Na₂SO₄ and concentrated in vacuo. The residue was filtered on silica gel, giving 4.04 g (68%) of the title compound.

¹H NMR (CDCl₃): 0.88 (d, J=7.4, 6H), 1.32–1.70 (m, 7H), 2.22 and 2.35 (ABX, J=11.0, 7.1, 2H), 3.16 (m, 2H), 3.69 (s, 3H), 4.95 (br s, 1H), 5.07 (s, 2H), 7.28–7.34 (m, 5H).

Step C. Preparation of Nα-Isobutyl-Nα-(4-methylbenzenesulfonyl)-Nε-benzyloxycarbonyl-L-lysine Methyl Ester To a stirred solution of the amine obtained in step B of this example (1.00 g, 2.34 mmol) in CH₂Cl₂ (3 mL) was added 4-methylbenzenesulfonyl chloride (670 mg, 3.51 mmol) and diisopropylethylamine (0.5 mL, 2.8 mmol). The reaction mixture was stirred overnight at room temperature. The mixture was treated with 1N HCl and extracted with CH₂Cl₂. The organic layer was dried over MgSO₄ and concentrated in vacuo. The crude material was purified by flash chromatography eluting with 30% EtOAc in hexane to yield 1.3 g (89%) of the title compound as a colorless oil.

¹H NMR (DMSO-d₆): 0.84 (d, J=7.2, 3H), 0.86 (d, J=6.3, 3H), 1.30–1.68 (m, 5H), 1.88–2.00 (m, 2H), 2.42 (s, 3H), 2.92 and 3.00 (ABX, J=14.7, 8.2, 2H), 3.18 (m, 2H), 3.50 (s, 3H), 4.40 (t, J=7.4, 1H), 4.78 (br s, 1H), 5.11 (s, 2H), 7.27–7.71 (m, 9H).

Step D. Preparation of Nα-Isobutyl-Nα-(4-methylbenzenesulfonyl)-Nε-benzyloxycarbonyl-DL-lysine To a stirred solution of the ester obtained in step C of this example (505 mg, 1.00 mmol) in a mixture of 50% MeOH in THF (4 mL) was added a 1N NaOH solution (3 mL, 3 mmol). The reaction was stirred at room temperature overnight, then diluted with 1N HCl until acidic and extracted twice with EtOAc. The combined organic layers were dried with MgSO₄ and concentrated in vacuo to give the title compound (490 mg, 100%) as an amorphous solid.

¹H NMR (DMSO-d₆): 0.78 (d, J=6.9, 3H), 0.81 (d, J=6.5, 3H), 1.15–1.50 (m, 5H), 1.75–1.80 (m, 2H), 2.36 (s, 3H), 2.75–3.00 (m, 4H), 4.20 (t, J=7.0, 1H), 5.00 (s, 2H), 7.20 (t, J=5.0, 1H), 7.30–7.67 (m, 9H), 12.70 (br s, 1H).

Step E. Preparation of Nα-Isobutyl-Nα-(4-methylbenzenesulfonyl)-Nε-(9-fluorenylmethoxycarbonyl)-DL-lysine 10% Pd/C (120 mg) was added to a stirred solution of the product from step D of this example (490 mg, 1.00 mmol). The suspension was flushed with hydrogen gas and maintained under $H_2$ pressure for 2 h. It was then filtered and concentrated in vacuo. The resulting white solid was partially dissolved in 1M $K_2CO_3$ (4 mL, 4 mmol), THF (6 mL) and acetonitrile (4 mL). To this suspension was added N-(9-fluorenylmethoxycarbonyloxy) succinimide (371 mg, 1.10 mmol). The reaction became clear and was stirred for 1 h at room temperature. The mixture was quenched by the addition of 2N HCl until acidic. The mixture was extracted twice with EtOAc, the combined organic layer was washed with brine, dried over $MgSO_4$ and concentrated in vacuo. The residue was purified by flash chromatography eluting with 60% EtOAc in hexane containing 0.4% AcOH to yield 480 mg (83%) of the title compound as a white solid.

$^1$H NMR (DMSO-$d_6$): 0.79 (d, J=7.1, 3H), 0.81 (d, J=7.1, 3H), 1.12–1.25 (m, 2H), 1.30–1.40 (m, 2H), 1.42–1.50 (m, 2H), 1.75–1.90 (m, 2H), 2.36 (s, 3H), 2.85 (m, 2H), 2.90 and 3.00 (ABX, J=14.3, 7.3, 2H), 4.16–4.21 (m, 2H), 4.28 (d, J=7.0, 2H), 7.21 (t, J=5.2, 1H), 7.30–7.42 (m, 6H), 7.60 (m, 4H), 7.88 (d, J=7.5, 2H), 12.69 (br s, 1H).

EXAMPLE 36

Nα-Isobutyl-Nα-(4-chlorobenzenesulfonyl)-Nε-(9-fluorenylmethoxycarbonyl)-DL-lysine (Compound No. 1)

Following the indications found in example 35 step C and substituting 4-methylbenzenesulfonyl chloride with 4-chlorobenzenesulfonyl chloride, the title compound was obtained (67% yield).

$^1$H NM (DMSO-$d_6$): 0.78 (d, J=6.1, 3H), 0.81 (d, J=6.1, 3H), 1.15–1.52 (m, 5H), 1.75–1.91 (m, 2H), 2.80–2.95 (m, 3H), 3.00 (dd, J=14.2, 7.2, 1H), 4.20 (m, 2H), 4.31 (d, J=6.5, 2H), 7.20 (t, J=5.6, 1H), 7.23–7.42 (m, 4H), 7.53–7.68 (m, 4H), 7.79 (d, J=7.4, 2H), 7.88 (d, J=7.4, 2H), 12.70 (br s, 1H).

EXAMPLE 37

Preparation of Nα-Isobutyl-Nα-(4-fluorobenzenesulfonyl)-Nε-(9-fluorenylmethoxycarbonyl)-DL-lysine (Compound No. 3)

Following the indications found in example 35 and substituting 4-bromobenzenesulfonyl chloride with 4-fluorobenzenesulfonyl chloride, the title compound was obtained (62% yield).

$^1$H NMR (DMSO-$d_6$): 0.78 (d, J=6.8, 3H), 0.81 (d, J=6.9, 3H), 1.18–1.28 (m, 2H), 1.30–1.42 (m, 2H), 1.45–1.53 (m, 1H), 1.79–1.95 (m, 2H), 2.90 (m, 3H), 3.00 (dd, J=14.6, 7.4, 1H), 4.20 (m, 2H), 4.31 (d, J=6.4, 2H), 7.22 (t, J=5.0, 1H), 7.30–7.45 (m, 6H), 7.67 (d, J=7.5, 1H), 7.82–7.91 (m, 4H).

EXAMPLE 38

General Preparation of Nα-Isobutyl-Nα-(4-substituted benzenesulfonyl)-Nε-(9-fluorenylmethoxycarbonyl)-L-lysine Step A. Preparation of Nε-Benzyloxycarbonyl-L-lysine Benzyl Ester To a stirred solution of Nα-tert-butoxycarbonyl-Nε-benzyloxycarbonyl-L-lysine (7.6 g, 20 mmol) in DMF (120 mL) was added potassium bicarbonate. After stirring the suspension for 1 h, benzyl bromide (1.31 mL, 11.0 mmol) was added dropwise. The reaction mixture was stirred overnight, then diluted with 1N HCl until acidic (pH approximately 3) and extracted with EtOAc. The organic layer was washed twice with brine, dried over $MgSO_4$ and concentrated in vacuo to yield the benzyl ester that was dissolved in $CH_2Cl_2$/TFA (60 mL/20 mL). The mixture was stirred until the disappearance of the starting material (1.2 h). The volatiles were removed in vacuo and dissolved in EtOAc and a solution of 1M $K_2CO_3$. The two phases were separated and the aqueous layer was washed twice with EtOAc. The combined layers were dried over $MgSO_4$ and concentrated in vacuo to give the title compound as a colourless oil (8.9 g, 95%).

$^1$H NMR (DMSO-$d_6$): 1.22–1.50 (m, 5H), 1.53–1.62 (m, 1H), 2.00 (br s, 2H), 2.95 (m, 2H), 3.30 (m, 1H), 5.00 (s, 2H), 5.10 (s, 2H), 7.20 (t, J=5.0, 1H), 7.25–7.40 (m, 5H).

Step B. Preparation of Nα-Alkyl-Nε-benzyloxycarbonyl-L-lysine Benzyl Ester

To a stirred solution of the product obtained in step A (4.32 g, 9.17 mmol), acetic acid (1.3 mL, 23 mmol) and sodium cyanoborohydride (691 mg, 11.0 mmol) in MeOH (120 mL) at 0° C. was added a solution of aldehyde (11.0 mmol) in MeOH (40 mL). The reaction mixture was warmed to room temperature and stirred for a period of 1 h. A saturated solution of $K_2CO_3$ (55 mL) was added and the mixture was partitioned between EtOAc (150 mL) and water (100 mL). The organic layer was washed with 1M $K_2CO_3$ and with brine, then dried over $MgSO_4$. The organic solvent was removed in vacuo and the residue was purified by flash chromatography eluting with hexane/EtOAc (60:40) to yield 65–95% of the title compound.

Step C. Preparation of Nα-(4-Substituted Benzenesulfonyl)-Nα-alkyl-Nε-benzyloxycarbonyl-L-lysine Benzyl Ester To a stirred solution of the product of step B of this example (1.0 mmol) in $CH_2Cl_2$ (1 mL) was added a substituted benzenesulfonyl chloride (1.5 mmol) followed by the addition of diisopropylethyl amine (174 µL). The reaction mixture was stirred for three days at room temperature. It was then diluted with 1N HCl. The organic phase was dried over $MgSO_4$ and concentrated in vacuo. The crude residue was flash chromatographed eluting with 40% EtOAc in hexane to yield the title compound at about 85%.

Step D. Preparation of Nα-(4-Substituted Benzenesulfonyl)-Nα-alkyl-Nε-(9-fluorenylmethoxycarbonyl)-L-lysine To the product obtained in step C of this example (1 mmol) in AcOH (5 mL) was added 10% Pd/C (120 mg). The suspension was flushed with hydrogen gas and maintained under $H_2$ atmosphere for 2 h. After filtering and evaporating in vacuo, the resulting white solid was partially dissolved in $K_2CO3$ (1M)/THF/$CH_3CN$ (4 mL/4 mL/4 mL). To this suspension was added N-(9-fluorenylmethoxycarbonyloxy) succinimide (371 mg, 1.10 mmol). The reaction turned slowly to colorless and was left stirring for 1 h. HCl (1M) was added until acidic pH and the reaction mixture was extracted twice with EtOAc. The combined organic layers were washed with brine, dried over $MgSO_4$ and concentrated. The residue was purified by flash chromatography eluting with a mixture of hexane/EtOAc containing 0.4% AcOH to yield 69–88% of the title compound.

EXAMPLE 39

Preparation of Nα-Isobutyl-Nα-(4-bromobenzenesulfonyl)-Nε-(9-fluorenylmethoxycarbonyl)-L-lysine (Compound No. 4)

Step A. Preparation of Nα-Isobutyl-Nε-benzyloxycarbonyl-L-lysine Benzyl Ester

The title compound was prepared by reacting Nε-benzyloxycarbonyl-L-lysine benzyl ester with isobutyraldehyde according to the indications of step B of example 38.

¹H NMR (CDCl₃): 0.88 (d, J=5.0, 6H), 1.30–1.41 (m, 2H), 1.42–1.53 (m, 2H), 1.58–1.62 (m, 3H), 2.28 and 2.35 (ABX, J=15.2, 7.4, 2H), 3.10–3.18 (m, 2H), 3.25 (t, J=7.0, 1H), 4.85 (br s, 1H), 5.10 (s, 2H), 5.12 and 5.20 (AB, J=12.5, 2H), 7.30–7.38 (m, 10H).

Step B. Preparation of Nα-Isobutyl-Nα-(4-bromobenzenesulfonyl)-Nε-benzyloxycarbonyl-L-lysine Benzyl Ester The product obtained in step A of this example was treated as described in step C of example 38 with 4-bromobenzenesulfonyl chloride to yield the title compound.

¹H NM (CDCl₃): 0.78 (d, J=6.7, 3H), 0.83 (d, J=6.1, 3H), 1.35–1.60 (m, 4H), 1.65–1.74 (m, 1H), 1.86–2.06 (m, 2H), 2.85 and 3.00 (ABX, J=14.5, 7.4, 2H), 3.17–3.24 (m, 2H), 4.45 (t, J=7.2, 1H), 4.84 (br s, 1H), 4.93 (s, 2H), 5.11 (s, 2H), 7.21–7.62 (m, 14H).

Step C. Preparation of Nα-Isobutyl-Nα-(4-bromobenzenesulfonyl)-Nε-(9-fluorenylmethoxycarbonyl)-L-lysine The title compound was prepared by following the indications of step D of example 38 using the product obtained in step B of this example and reacting it with N-(9-fluorenylmethoxycarbonyloxy) succinimide.

¹H NMR (DMSO-d₆): 0.79 (d, J=7.0, 3H), 0.81 (d, J=7.1, 3H), 1.15–1.25 (m, 2H), 1.30–1.40 (m, 2H), 1.42–1.50 (m, 1H), 1.78–1.92 (m, 2H), 2.89 (m, 2H), 2.95 and 3.00 (ABX, J=14.8, 7.3, 2H), 4.20 (m, 2H), 4.30 (d, J=6.4, 2H), 7.21 (t, J=5.0, 1H), 7.30–7.52 (m, 6H), 7.62 (d, J=7.4, 1H), 7.67–7.90 (m, 6H), 12.70 (br s, 1H).

The D-lysine derivative was prepared in a similar manner.

EXAMPLE 40

Preparation of Nα-(4-Aminobenzenesulfonyl)-Nα-isobutyl-Nε-(9-fluorenylmethoxycarbonyl)-L-lysine (Compound No. 44)

Step A. Preparation of Nα-Isobutyl-Nα-(4-nitrobenzenesulfonyl)-Nε-benzyloxycarbonyl-L-lysine Benzyl Ester (Compound No. 78)

The product obtained in step A of example 39 was treated as described in step C of example 38 with 4-nitrobenzenesulfonyl chloride to yield the title compound.

¹H NMR (CDCl₃): 0.79 (d, J=6.0, 3H), 0.85 (d, J=6.1, 3H), 1.42–1.65 (m, 4H), 1.67–1.73 (m, 1H), 1.93 (h, J=6.0, 1H), 2.00–2.10 (m, 1H), 2.90 and 3.05 (ABX, J=14.5, 7.4, 2H), 3.20 (m, 2H), 4.51 (t, J=7.2, 1H), 4.80 (br s, 1H), 4.91 (s, 2H), 5.10 (s, 2H), 7.15 (d, J=7.0, 2H), 7.30–7.42 (m, 9H).

Step B. Preparation of Nα-(4-Aminobenzenesulfonyl)-Nα-isobutyl-Nε-(9-fluorenylmethoxycarbonyl)-L-lysine The title compound was prepared by following the indications of step D of example 38 using the product obtained in step A of this example and reacting it with N-(9-fluorenylmethoxycarbonyloxy) succinimide. In this case, the hydrogenolysis of the benzyl groups and the reduction of the nitro group took place simultaneously.

¹H NMR (DMSO-d₆): 0.78 (d, J=6.9, 3H), 0.80 (d, J=6.0, 3H), 1.18–1.48 (m, 5H), 1.73–1.82 (m, 2H), 2.82–3.00 (m, 4H), 4.10 (t, J=7.1, 1H), 4.20 (t, J=7.0, 1H), 4.28 (d, J=7.6 2H), 5.95 (br s, 2H), 6.57 (d, J=7.6, 2H), 7.22 (t, J=5.2, 1H), 7.30–7.45 (m, 6H), 7.67 (d, J=7.1, 2H), 7.88 (d, J=7.3, 2H), 12.60 (br s, 1H).

EXAMPLE 41

Preparation of Nα-Isobutyl-Nα-benzenesulfonyl-Nε-(9-fluorenylmethoxycarbonyl)-L-lysine (Compound No. 9)

Step A. Preparation of Nα-Isobutyl-Nα-benzenesulfonyl-Nε-benzyloxycarbonyl-L-lysine Benzyl Ester The product obtained in step A of example 39 was treated as described in step C of example 38 with benzenesulfonyl chloride to yield the title compound.

¹H NMR (CDCl₃): 0.78 (d, J=6.0, 3H), 0.83 (d, J=6.8, 3H), 1.30–1.73 (m, 5H), 1.85–2.00 (m, 2H), 2.88 and 3.15 (ABX, J=14.0, 7.2, 2H), 3.16 (m, 2H), 4.45 (t, J=7.2, 1H), 2.82 (br s, 1H), 4.91 (s, 2H), 5.10 (s, 2H), 7.21–7.55 (m, 13H), 7.79 (d, J=7.7, 2H).

Step B. Preparation of Nα-Isobutyl-Nα-benzenesulfonyl-Nε-(9-fluorenylmethoxycarbonyl)-L-lysine The title compound was prepared by following the indications of step D of example 38 using the product obtained in step A of this example and reacting it with N-(9-fluorenylmethoxycarbonyloxy) succinimide.

¹H NMR (DMSO-d₆): 0.79 (d, J=6.1, 3H), 0.81 (d, J=6.7, 3H), 1.15–1.50 (m, 5H), 1.82–1.93 (m, 2H), 2.89 (m, 2H), 2.93 and 3.00 (ABX, J=14.7, 7.1, 2H), 4.20 (m, 2H), 4.30 (d, J=6.5, 2H), 7.22 (t, J=5.2, 1H), 7.31–7.42 (m, 4H), 7.52–7.70 (m, 5H), 7.80 (d, J=7.7, 2H), 7.87 (d, J=7.3, 2H), 12.70 (br s, 1H).

EXAMPLE 42

Preparation of Nα-Isobutyl-Nα-(1-naphthalenesulfonyl)-Nε-(9-fluorenylmethoxycarbonyl)-L-lysine (Compound No. 8)

Step A. Preparation of Nα-Isobutyl-Nα-(1-naphthalenesulfonyl)-Nε-benzyloxycarbonyl-L-lysine Benzyl Ester The product obtained in step A of example 39 was treated as described in step C of example 38 with 1-naphthalenesulfonyl chloride to yield the title compound.

¹H NMR (CDCl₃): 0.71 (d, J=7.3, 3H), 0.78 (d, J=7.0, 3H), 1.20–1.48 (m, 4H), 1.55–1.65 (m, 1H), 1.82–2.00 (m, 2H), 3.00 and 3.20 (ABX, J=14.2, 7.4, 2H), 3.12 (m, 2H), 4.50 (t, J=7.2, 1H), 4.71–4.82 (m, 3H), 5.10 (s, 2H), 7.10–7.60 (m, 4H), 7.90 (d, J=6.4, 1H), 8.00 (d, J=8.0, 1H), 8.29 (d, J=7.3, 1H), 8.76 (d, J=7.8, 1H).

Step B. Preparation of Nα-Isobutyl-Nα-(1-naphthalenesulfonyl)-Nε-(9-fluorenylmethoxycarbonyl)-L-lysine The title compound was prepared by following the indications of step D of example 38 using the product obtained in step A of this example and reacting it with N-(9-fluorenylmethoxycarbonyloxy) succinimide.

¹H NMR (DMSO-d₆): 0.70 (d, J=6.2, 3H), 0.73 (d, J=6.3, 3H), 1.10–1.18 (m, 2H), 1.20–1.28 (m, 2H), 1.34–1.45 (m, 1H), 1.75–1.92 (m, 2H), 2.80 (m, 2H), 3.00 and 3.11 (ABX, J=14.6, 6.2, 2H), 4.20 (m, 1H), 4.30 (m, 2H), 5.00 (s, 1H), 7.21 (m, 1H), 7.28–7.45 (m, 4H), 7.60–8.30 (m, 9H), 8.65 (d, J=9.0, 1H).

EXAMPLE 43

Preparation of Nα-Isobutyl-Nα-(4-tert-butylbenzenesulfonyl)-Nε-(9-fluorenylmethoxycarbonyl)-L-lysine (Compound No. 10)

Step A. Preparation of Nα-Isobutyl-Nα-(4-tert-butylbenzenesulfonyl)-Nε-benzyloxycarbonyl-L-lysine Benzyl Ester The product obtained in step A of example 39 was treated as described in step C of example 38 with 4-tert-butylbenzenesulfonyl chloride to yield the title compound.

¹H NMR (CDCl₃): 0.77 (d, J=6.0, 3H), 0.82 (d, J=7.0, 3H), 1.32 (s, 9H), 1.28–1.70 (m, 5H), 1.88–2.00 (m, 2H), 2.87 and 3.00 (ABX, J=14.0, 7.0, 2H), 3.15 (m, 2H), 4.47 (t, J=7.2, 1H), 4.83 (br s, 1H), 4.90 (s, 2H), 5.10 (s, 2H), 7.20–7.43 (m, 12H), 7.72 (d, J=7.8, 2H).

Step B. Preparation of Nα-Isobutyl-Nα-(4-tert-butylbenzenesulfonyl)-Nε-(9-fluorenylmethoxycarbonyl)-L-lysine The title compound was prepared by following the indications of step D of example 38 using the product obtained in step A of this example and reacting it with N-(9-fluorenylmethoxycarbonyloxy) succinimide.

$^1$H NMR (CDCl$_3$): 0.80 (d, J=6.9, 3H), 0.82 (d, J=6.2, 3H), 1.10–1.20 (m, 2H), 1.27 (s, 9H), 1.28–1.42 (m, 3 H), 1.75–1.92 (m, 2H), 2.82 (m, 2H), 2.95 (m, 2H), 4.15 (t, J=6.5, 1H), 4.20 (t, J=7.1, 1H), 4.28 (d, J=6.6, 2H), 7.20 (t, J=5.2, 1H), 7.28–7.45 (m, 4H), 7.56 (d, J=7.0, 2H), 7.67 (m, 4H), 7.88 (d, J=7.1, 2H), 12.70 (br s, 1H).

EXAMPLE 44

Preparation of Nα-Isobutyl-Nα-(4-methoxybenzenesulfonyl)-Nε-(9-fluorenylmethoxycarbonyl)-L-lysine (Compound No. 7)

Step A. Preparation of Nα-Isobutyl-Nα-(4-methoxybenzenesulfonyl)-Nε-benzyloxycarbonyl-L-lysine Benzyl Ester The product obtained in step A of example 39 was treated as described in step C of example 38 with 4-methoxybenzenesulfonyl chloride to yield the title compound.

$^1$H NMR (CDCl$_3$): 0.78 (d, J=6.6, 3H), 0.83 (d, J=6.1, 3H), 1.33–1.80 (m, 5H), 1.86–2.00 (m, 2H), 2.90 and 3.00 (ABX, J=14.3, 7.6, 2H), 3.15–3.20 (m, 2H), 3.82 (s, 3H), 4.43 (t, J=7.3, 1H), 4.82 (br s, 1H), 4.94 and 4.96 (AB, J=12.6, 2H), 5.10 (s, 2H), 6.83 (d, J=8.4, 2H), 7.20–7.40 (m, 10H), 7.70 (d, J=8.1, 2H).

Step B. Preparation of Nα-Isobutyl-Nα-(4-methoxybenzenesulfonyl)-Nε-(9-fluorenylmethoxycarbonyl)-L-lysine The title compound was prepared by following the indications of step D of example 38 using the product obtained in step A of this example and reacting it with N-(9-fluorenylmethoxycarbonyloxy) succinimide.

$^1$H NMR (CDCl$_3$): 0.78 (d, J=6.9, 3H), 0.81 (d, J=6.9, 3H), 1.15–1.51 (m, 5H), 1.75–1.90 (m, 2H), 2.88–2.92 (m, 3H), 2.97 (dd, J=14.5, 7.6, 2H), 3.81 (s, 3H), 4.15 (t, J=6.8, 1H), 4.18 (t, J=6.7, 1H), 4.20 (d, J=6.6, 2H), 7.06 (d, J=8.7, 2H), 7.22 (t, J=4.9, 1H), 7.70 (m, 4H), 7.89 (d, J=7.4, 2H), 12.60 (br s, 1H).

EXAMPLE 45

Preparation of Nα-Isobutyl-Nα-(4-methylbenzenesulfonyl)-Nε-(9-fluorenylmethoxycarbonyl)-L-lysine (Compound No. 67)

Step A. Preparation of Nα-isobutyl-Nα-(4-methylbenzenesulfonyl)-Nε-benzyloxycarbonyl-L-lysine Benzyl Ester (Compound No. 75)

The product obtained in step A of example 39 was treated as described in step C of example 38 with 4-methylbenzenesulfonyl chloride to yield the title compound.

$^1$H NMR (CDCl$_3$): 0.79 (d, J=7.0, 3H), 0.83 (d, J=7.0, 3H), 1.30–1.45 (m, 2H), 1.48–1.57 (m, 2H), 1.60–1.72 (m, 1H), 1.91–2.00 (m, 2H), 2.40 (s, 3H), 2.88 and 3.14 (ABX, J=14.5, 7.4, 2H), 3.16 (m, 2H), 4.44 (t, J=7.3, 1H), 4.85 (br s, 1H), 4.93 (s, 2H), 5.10 (s, 2H), 7.16 (d, J=7.7, 2H), 7.20–7.42 (m, 10H), 7.65 (d, J=8.3, 2H).

Step B. Preparation of Nα-Isobutyl-Nα-(4-methylbenzenesulfonyl)-Nε-(9-fluorenylmethoxycarbonyl)-L-lysine The title compound was prepared by following the indications of step D of example 38 using the product obtained in step A of this example and reacting it with N-(9-fluorenylmethoxycarbonyloxy) succinimide.

$^1$H NMR (CDCl$_3$): 0.79 (d, J=7.1, 3H), 0.81 (d, J=7.1, 3H), 1.12–1.25 (m, 2H), 1.30–1.40 (m, 2H), 1.42–1.50 (m, 2H), 1.78–1.90 (m, 2H), 2.36 (s, 3H), 2.85 (m, 2H), 2.88 and 3.04 (ABX, J=14.3, 7.3, 2H), 4.16–4.21 (m, 2H), 4.28 (d, J=7.0, 2H), 7.30–7.42 (m, 6H), 7.60 (m, 4H), 7.88 (d, J=7.5, 2H), 12.69 (br s, 1H).

EXAMPLE 46

Preparation of Nα-Isobutyl-Nα-(2,4,6-trimethylbenzenesulfonyl)-Nε-(9-fluorenylmethoxycarbonyl)-L-lysine (Compound No. 42)

Step A. Preparation of Nα-Isobutyl-Nα-(2,4,6-trimethylbenzenesulfonyl)-Nε-benzyloxycarbonyl-L-lysine Benzyl Ester The product obtained in step A of example 39 was treated as described in step C of example 38 with 2,4,6-trimethylbenzenesulfonyl chloride to yield the title compound.

$^1$H NMR (CDCl$_3$): 0.70 (d, J=6.7, 3H), 0.78 (d, J=6.5, 3H), 1.22–1.55 (m, 4H), 1.65–1.80 (m, 2H), 1.95–2.05 (m, 1H), 2.27 (s, 3H), 2.56 (s, 6H), 3.10–3.20 (m, 4H), 4.26 (t, J=6.5, 1H), 4.83 (br s, 1H), 5.06 and 5.11 (AB, J=12.6, 2H), 5.10 (s, 2H), 6.87 (s, 2H), 7.27–7.36 (m, 10H).

Step B. Preparation of Nα-Isobutyl-Nα-(2,4,6-trimethylbenzenesulfonyl)-Nε-(9-fluorenylmethoxycarbonyl)-L-lysine The title compound was prepared by following the indications of step D of example 39 using the product obtained in step A of this example and reacting it with N-(9-fluorenylmethoxycarbonyloxy) succinimide.

$^1$H NMR (CDCl$_3$): 0.69 (d, J=6.8, 3H), 0.73 (d, J=6.0, 3H), 1.15–1.40 (m, 4H), 1.52–1.62 (m, 1H), 1.72 (h, J=6.5, 1H), 1.82–1.93 (m, 1H), 2.24 (s, 3H), 2.53 (s, 6H), 2.90 (m, 2H), 3.10 (t, J=7.2, 2H), 3.98 (t, J=7.0, 1H), 4.20 (t, J=6.7, 1H), 4.28 (d, J=6.8, 2H), 7.03 (s, 2H), 7.20 (t, J=5.2, 1H), 7.30–7.45 (m, 4H), 7.67 (d, J=7.3, 2H), 7.87 (d, J=7.5, 2H), 12.80 (br s, 1H).

EXAMPLE 47

Preparation of Nα-Isobutyl-Nα-(4-iodobenzenesulfonyl)-Nε-benzyloxycarbonyl-DL-lysine (Compound No. 48)

Step A. Preparation of Nα-Isobutyl-Nα-(4-iodobenzenesulfonyl)-Nε-benzyloxycarbonyl-L-lysine Benzyl Ester The product obtained in step A of example 39 was treated as described in step C of example 38 with 4-iodobenzenesulfonyl chloride to yield the title compound.

$^1$H NMR (CDCl$_3$): 0.78 (d, J=6.1, 3H), 0.83 (d, J=6.3, 3H), 1.38–1.60 (m, 4H), 1.65–1.75 (m, 1H), 1.90 (h, J=6.2, 1H), 1.91–2.02 (m, 1H), 2.85 and 3.00 (ABX, J=14.5, 7.4, 2H), 3.20 (m, 2H), 4.45 (t, J=7.2, 1H), 4.83 (br s, 1H), 4.93 (s, 2H), 5.11 (s, 2H), 7.20–7.70 (m, 14H).

Step B. Preparation of Nα-Isobutyl-Nα-(4-iodobenzenesulfonyl)-Nε-benzyloxycarbonyl-DL-lysine The product from step A of this example was saponified according to the indication of step D of example 35 to provide the title compound.

¹H NMR (DMSO-d₆): 0.79 (d, J=6.1, 3H), 0.82 (d, J=6.4, 3H), 1.18–1.55 (m, 5H), 1.74–1.93 (m, 2H), 2.86–2.99 (m, 3H), 3.00 (dd, J=15.5, 7.7, 1H), 4.20 (t, J=7.2, 1H), 5.00 (s, 2H), 7.20 (br s, 1H), 7.28–7.36 (m, 5H), 7.55 (d, J=7.0, 2H), 7.93 (d, J=8.0, 2H), 12.73 (br s, 1H).

EXAMPLE 48

Preparation of Nα-Isobutyl-Nα-(4-methylbenzenesulfonyl)-Nδ-(9-fluorenylmethoxycarbonyl)-DL-ornithine (Compound No. 6)

Step A. Preparation of Nα-Isobutyl-Nδ-benzyloxycarbonyl-DL-ornithine Methyl Ester The title compound was prepared by reacting Nα-tert-butoxycarbonyl-Nδ-benzyloxycarbonyl-DL-ornithine with methyl iodide according to the indications of step A of example 35. The product treated with TFA in CH₂Cl₂ and the residue was directly subjected to the reductive alkylation as described in step B of example 35.

¹H NMR (CDCl₃): 0.87 (d, J=6.5, 6H), 1.50 (br s, 1H), 1.55–1.72 (m, 5H), 2.25 and 2.38 (ABX, J=11.1, 6.0, 2H), 3.16–3.25 (m, 3H), 3.70 (s, 3H), 5.08 (s, 2H), 5.25 (br s, 1H), 7.29–7.40 (m, 5H).

Step B. Preparation of Nα-Isobutyl-Nα-(4-methylbenzenesulfonyl)-Nδ-benzyloxycarbonyl-DL-ornithine Methyl Ester The title compound was prepared (89% yield) by following the indications of step C of example 35 using the product obtained in step B of this example and reacting it with 4-methylbenzenesulfonyl chloride.

¹H NMR (CDCl₃): 0.84 (d, J=7.4, 3H), 0.87 (d, J=7.8, 3H), 1.52–1.70 (m, 3H), 1.88–2.00 (m, 2H), 2.90 and 3.05 (ABX, J=14.5, 7.5, 2H), 3.15–3.22 (m, 2H), 3.48 (s, 3H), 4.41 (t, J=6.3, 1H), 4.90 (br s, 1H), 5.10 (s, 2H), 7.27 (d, J=8.1, 2H), 7.31–7.36 (m, 5H), 7.70 (d, J=7.5, 2H).

Step C. Preparation of Nα-Isobutyl-Nα-(4-methylbenzenesulfonyl)-Nδ-(9-fluorenylmethoxycarbonyl)-DL-ornithine The title compound was prepared by following the indications of step D of example 35 using the product obtained in step B of this example and reacting it with N-(9-fluorenylmethoxycarbonyloxy) succinimide.

¹H NMR (DMSO-d₆): 0.77 (d, J=7.2, 3H), 0.80 (d, J=7.1, 3H), 1.30–1.52 (m, 3H), 1.68–1.90 (m, 2H), 2.35 (s, 3H), 2.85 and 2.95 (ABX, J=14.0, 7.3, 2H), 2.90 (m, 2H), 4.20 (m, 2H), 4.30 (d, J=6.4, 2H), 7.20–7.42 (m, 7H), 7.60 (m, 4H), 7.88 (d, J=7.5, 2H), 12.65 (br s, 1H).

EXAMPLE 49

Preparation of Nα-Isobutyl-Nα-benzoyl-Nε-(9-fluorenylmethoxycarbonyl)-L-lysine (Compound No. 46)

To a stirred solution of Nα-isobutyl-Nε-benzyloxycarbonyl-L-lysine (213 mg, 0.50 mmol) in CH₂Cl₂ (5 mL) was added benzoyl chloride (140 mg, 1.00 mmol) and DIEA (130 mg, 1.00 mmol). The reaction mixture was stirred at room temperature for 1 h and then diluted with 1N HCl. The mixture was extracted with EtOAc, dried over MgSO₄ and evaporated to dryness. The residue was purified by flash chromatography. Elution with 70% EtOAc in hexane provided Nα-isobutyl-Nα-benzoyl-Nε-benzyloxycarbonyl-L-lysine that was further hydrogenolyzed using 10% Pd/C and then treated with 9-fluorenylmethyl chloroformate instead of N-(9-fluorenylmethoxycarbonyloxy) succinimide as outlined in step D of example 38 to provide the title compound (90% yield).

¹H NMR (DMSO-d₆): 0.70 (d, J=6.3, 3H), 0.89 (d, J=6.5, 3H), 1.22–1.55 (m, 4H), 1.62–1.90 (m, 3H), 2.90–3.22 (m, 4H), 3.92–4.12 (m, 1H), 4.20 (t, J=6.8, 1H), 4.28 (t, J=6.2, 2H), 7.20–7.45 (m, 10H), 7.70 (d, J=7.2, 2H), 7.90 (d, J=7.5, 2H), 12.50 (s, 1H).

EXAMPLE 50

Preparation of Nα-Benzyl-Nα-(4-methylbenzenesulfonyl)-Nε-(9-fluorenylmethoxycarbonyl)-L-lysine (Compound No. 40)

Step A. Preparation of Nα-Benzyl-Nε-benzyloxycarbonyl-L-lysine Benzyl Ester

The title compound was prepared by reacting Nε-benzyloxycarbonyl-L-lysine benzyl ester according to the indications of step B of example 38 using benzaldehyde instead of isobutyraldehyde.

¹H NMR (CDCl₃): 1.30–1.52 (m, 4H), 1.60–1.74 (m, 2H), 3.15 (m, 2H), 3.30 (t, J=6.5, 1H), 3.60 and 3.80 (AB, J=16.7, 2H), 4.76 (br s, 1H), 5.11 (s, 2H), 5.18 (q, J=11.7, 2H), 7.22–7.40 (m, 15H).

Step B. Preparation of Nα-Benzyl-Nα-(4-methylbenzenesulfonyl)-Nε-benzyloxycarbonyl-L-lysine Benzyl Ester The product obtained in step A of this example was treated as described in step C of example 38 with 4-methylbenzenesulfonyl chloride to yield the title compound.

¹H NMR (CDCl₃): 1.05–1.32 (m, 4H), 1.45–1.58 (m, 1H), 1.72–1.80 (m, 1H), 2.40 (s, 3H), 3.00 (m, 2H), 4.31 and 4.70 (AB, J=16.1, 2H), 4.57 (dd, J=9.0, 5.7, 1H), 4.70 (d, J=16.1, 1H), 4.80 (br s, 1H), 4.85 (s, 2H), 5.11 (s, 2H), 7.16–7.37 (m, 17H), 7.68 (d, J=7.5, 2H).

Step C. Preparation of Nα-Benzyl-Nα-(4-methylbenzenesulfonyl)-Nε-(9-fluorenylmethoxycarbonyl)-L-lysine The title compound was prepared by following the indications of step D of example 38 using the product obtained in step B of this example and reacting it with N-(9-fluorenylmethoxycarbonyloxy) succinimide.

¹H NMR (DMSO-d₆): 1.00, 1.20 (m, 4H), 1.27–1.40 (m, 1H), 1.55–1.62 (m, 1H), 2.37 (s, 3H), 2.75 (m, 2H), 4.20 (t, J=6.5, 1H), 4.25–4.30 (m, 3H), 4.33 and 4.65 (AB, J=16.4, 2H), 7.15 (t, J=5.2, 1H), 7.20–7.42 (m, 11H), 7.67 (d, J=7.3, 4H), 7.88 (d, J=7.5, 2H), 12.70 (br s, 1H).

EXAMPLE 51

Preparation of Nα-Cyclopropylmethyl-Nα-(4-methylbenzenesulfonyl)-Nε-(9-fluorenylmethoxycarbonyl)-L-lysine (Compound No. 43)

Step A. Preparation of Nα-Cyclopropylmethyl-Nε-benzyloxycarbonyl-L-lysine Benzyl Ester The title compound was prepared by reacting Nε-benzyloxycarbonyl-L-lysine benzyl ester according to the indications of step B of example 38 using cyclopropylcarboxaldehyde instead of isobutyraldehyde.

¹H NMR (CDCl₃): 0.00–0.07 (m, 2H), 0.41–0.47 (m, 2H), 0.86–0.93 (m, 1H), 1.22–1.70 (m, 6H), 1.78 (br s, 1H), 2.20 and 2.50 (ABX, J=12.0, 8.1, 2H), 3.10 (m, 2H), 3.30 (m, 1H), 5.00 (br s, 1H), 5.12 (s, 2H), 5.15 and 5.18 (AB, J=12.7, 2H), 7.30–7.36 (m, 10H).

Step B. Preparation of Nα-Cyclopropylmethyl-Nα-(4-methylbenzenesulfonyl)-Nε-benzyloxycarbonyl-L-lysine Benzyl Ester The product obtained in step A of this example was treated as described in step C of example 38 with 4-methylbenzenesulfonyl chloride to yield the title compound.

¹H NMR (CDCl₃): 0.04 (m, 1H), 0.15 (m, 1H), 0.41 (d, J=7.7, 2H), 0.90 (m, 1H), 1.22–1.60 (m, 4H), 1.65–1.80 (m, 1H), 1.90–2.03 (m, 1H), 2.35 (s, 3H), 2.90 and 3.20 (ABX, J=15.3, 7.2, 2H), 3.15 (m, 2H), 4.58 (dd, J=9.1, 5.4, 1H), 4.90 (s, 2H), 5.00 (br s, 1H), 5.10 (s, 2H), 7.10–7.40 (m, 12H), 7.67 (d, J=8.5, 2H).

Step C. Preparation of Nα-Benzyl-Nα-(4-methylbenzenesulfonyl)-Nε-(9-fluorenylmethoxycarbonyl)-L-lysine The title compound was prepared by following the indications of step D of example 38 using the product obtained in step B of this example and reacting it with N-(9-fluorenylmethoxycarbonyloxy) succinimide.

¹H NMR (DMSO-d₆): 0.12 (m, 1H), 0.21 (m, 1H), 0.40 (d, J=7.8, 2H), 0.95–1.03 (m, 1H), 1.17–1.45 (m, 4H), 1.55–1.68 (m, 1H), 1.80–1.90 (m, 1H), 2.90 and 3.20 (ABX, J=15.4, 5.8, 2H), 2.95 (m, 2H), 4.20 (t, J=6.5, 1H), 4.29 (d, J=6.6, 2H), 7.25 (t, J=5.4, 1H), 7.30–7.45 (m, 6H), 7.69 (d, J=7.5, 4H), 7.88 (d, J=7.4, 2H), 12.70 br s, 1H).

EXAMPLE 52

Preparation of Nα,Nε-di-(9-Fluorenylmethoxycarbonyl)-L-lysine (Compound No. 71)

The reaction of 9-fluorenylmethyl chloroformate with L-lysine according to the conditions described in example 2 provided the title product in 71% yield.

¹H NMR (DMSO-d₆): 1.20–1.50 (m, 4H), 1.55–1.78 (m, 1H), 3.00 (m, 2H), 3.92 (m, 1H), 4.20 (t, J =6.3, 2H), 4.29 (d, J=7.0, 4H), 7.27 (t, J=5.3, 1H), 7.29–7.42 (m, 8H), 7.60 (d, J=7.9, 1H), 7.67–7.73 (m, 4H), 7.88 (m, 4H), 12.50 (br s, 1H).

EXAMPLE 53

Preparation of Nα,Nδ-di-(9-Fluorenylmethoxycarbonyl)-L-ornithine (Compound No. 73)

The reaction of 9-fluorenylmethyl chloroformate with L-ornithine according to the conditions described in example 2 provided the title product in 79% yield.

¹H NMR (DMSO₆): 1.42–1.80 (m, 4H), 3.00 (m, 2H), 3.94 (m, 1H), 4.20 (t, J=6.3, 2H), 4.29 (d, J=7.0, 4H), 7.28 (t, J=5.2, 1H), 7.30–7.48 (m, 8H), 7.63 (d, J=7.6, 1H), 7.67–7.73 (m, 4H), 7.88 (m, 4H), 12.50 (br s, 1H).

EXAMPLE 54

Preparation of Nα-(4-Nitrobenzenesulfonyl)-Nε-(9-fluorenylmethoxycarbonyl)-L-lysine (Compound No. 103)

Nα-tert-butoxycarbonyl-Nε-(9-fluorenylmethoxycarbonyl)-L-lysine was deprotected at the α position by treatment with TFA/CH₂Cl₂ as described in the procedure outlined in example 24 and the resulting trifluoroacetate salt was alkylated with 4-nitrobenzenesulfonyl chloride as described in example 2, affording the title compound in 51% yield.

¹H NMR (DMSO-d₆): 1.13–1.33 (m, 4H), 1.45–1.70 (m, 2H), 2.90 (m, 2H), 3.75 (dd, J=13.0, 7.3, 1H), 4.20 (t, J=6.3, 1H), 4.28 (d, J=7.0, 2H), 7.20 (t, J=5.2, 1H), 7.30–7.48 (m, 4H), 7.67 (d, J=7.3, 1H), 7.88 (d, J=7.3, 2H), 8.01 (d, J=8.8, 2H), 8.38 (d, J=8.1, 2H), 8.50 (d, J=8.1, 1H).

EXAMPLE 55

Preparation of Nα-(4-Chlorobenzenesulfonyl)-Nε-(9-fluorenylmethoxycarbonyl)-L-lysine (Compound No. 72)

Nα-tert-butoxycarbonyl-Nε-(9-fluorenylmethoxycarbonyl)-L-lysine was deprotected at the α position by treatment with TFA/CH₂Cl₂ as described in the procedure outlined in example 24 and the resulting trifluoroacetate salt was alkylated with 4-chlorobenzenesulfonyl chloride as described in example 2, affording the title compound in 38% yield.

¹H NMR (DMSO-d₆): 1.12–1.38 (m, 4H), 1.42–1.65 (m, 2H), 2.90 (m, 2H), 3.67 (dd, J=13.0, 7.7, 1H), 4.20 (t, J=6.5, 1H), 4.29 (d, J=6.9, 2H), 7.20 (t, J=5.2, 1H), 7.30–7.42 (m, 4H), 7.62 (d, J=7.3, 1H), 7.67 (d, J=7.9, 2H), 7.75 (d, J=7.9, 2H), 7.88 (d, J=8.2, 2H), 8.23 (d, J=8.9, 1H).

EXAMPLE 56

Preparation of Nα-(4-Chlorobenzenesulfonyl)-Nδ-(9-fluorenylmethoxycarbonyl)-L-ornithine (Compound No. 74)

Nα-tert-butoxycarbonyl-Nδ-(9-fluorenylmethoxycarbonyl)-L-ornithine was deprotected at the α position by treatment with TFA/CH₂Cl₂ as described in the procedure outlined in example 24 and the resulting trifluoroacetate salt was alkylated with 4-chlorobenzenesulfonyl chloride as described in example 2, affording the title compound in 33% yield.

¹H NMR (DMSO-d₆): 1.32–1.52 (m, 3H), 1.56–1.68 (m, 1H), 2.90 (m, 2H), 3.70 (dd, J=13.1, 7.2, 1H), 4.20 (t, J=6.3, 1H), 4.28 (d, J=6.7, 2H), 7.26 (t, J=5.1, 1H), 7.31–7.45 (m, 4H), 7.60 (d, J=8.3, 2H), 7.67 (d, J=7.3, 2H), 7.75 (d, J=8.3, 2H), 7.87 (d, J=7.2, 2H), 8.25 (d, J=8.9, 1H).

EXAMPLE 57

Preparation of Nα-(2-Nitrobenzenesulfonyl)-Nε-(9-fluorenylmethoxycarbonyl)-L-lysine (Compound No. 107)

Nα-tert-butoxycarbonyl-Nε-(9-fluorenylmethoxycarbonyl)-L-lysine was deprotected at the α position by treatment with TFA/CH₂Cl₂ as described in the procedure outlined in example 24 and the resulting trifluoroacetate salt was alkylated with 2-nitrobenzenesulfonyl chloride as described in example 2, affording the title compound in 48% yield.

¹H NMR (DMSO-d₆): 1.32–1.52 (m, 3H), 1.56–1.68 (m, 1H), 2.90 (m, 2H), 3.70 (dd, J=13.1, 7.2, 1H), 4.20 (t, J=6.3, 1H), 4.28 (d, J=6.7, 2H), 7.26 (t, J=5.1, 1H), 7.31–7.45 (m, 4H), 7.60 (d, J=8.3, 2H), 7.67 (d, J=7.3, 2H), 7.75 (d, J=8.3, 2H), 7.87 (d, J=7.2, 2H), 8.25 (d, J=8.9, 1H).

EXAMPLE 58

Preparation of Nα-(4-Bromobenzenesulfonyl)-Nε-(9-fluorenylmethoxycarbonyl)-L-lysine (Compound No. 66)

Nα-tert-butoxycarbonyl-Nε-(9-fluorenylmethoxycarbonyl)-L-lysine was deprotected at the α position by treatment with TFA/CH₂Cl₂ as described in the procedure outlined in example 24 and the resulting trifluoroacetate salt was alkylated with 4-bromobenzenesulfonyl chloride as described in example 2, affording the title compound in 65% yield.

¹H NMR(DMSO-d₆): 1.15–1.38 (m, 4H), 1.42–1.55 (m, 2H), 2.90 (m, 2H), 3.67 (dd, J=12.0, 5.6, 1H), 4.20 (t, J=7.0, 1H), 4.27 (d, J=7.0, 2H), 7.20 (t, J=5.0, 1H), 7.30–7.90 (m, 12H), 8.24 (d, J=8.8, 1H), 12.50 (br s, 1H).

EXAMPLE 59

Preparation of Nα-(1-Naphthalenesulfonyl)-Nε-(9-fluorenylmethoxycarbonyl)-L-lysine (Compound No. 102)

Nα-tert-butoxycarbonyl-Nε-(9-fluorenylmethoxycarbonyl)-L-lysine was deprotected at the α position by treatment with TFA/CH$_2$Cl$_2$ as described in the procedure outlined in example 24 and the resulting trifluoroacetate salt was alkylated with 1-naphthalenebenzenesulfonyl chloride as described in example 2, affording the title compound in 71% yield.

$^1$H NMR (DMSO-d$_6$): 1.15–1.38 (m, 4H), 1.42–1.63 (m, 2H), 2.80 (m, 2H), 3.61 (m, 1H), 4.20 (t, J=7.0, 1H), 4.27 (d, J=7.0, 2H), 7.17 (t, J=5.0, 1H), 7.25–8.13 (m, 15H), 8.40 (s, 1H), 12.40 (br s, 1H).

EXAMPLE 60

Preparation of Nα-(4-Methoxylbenzenesulfonyl)-Nε-(9-fluorenylmethoxycarbonyl)-L-lysine (Compound No. 104)

Nα-tert-butoxycarbonyl-Nε-(9-fluorenylmethoxycarbonyl)-L-lysine was deprotected at the α position by treatment with TFA/CH$_2$Cl$_2$ as described in the procedure outlined in example 24 and the resulting trifluoroacetate salt was alkylated with 4-methoxybenzenesulfonyl chloride as described in example 2, affording the title compound in 65% yield.

$^1$H NMR (DMSO-d$_6$): 1.10–1.40 (m, 4H), 1.42–1.60 (m, 2H), 2.86 (m, 2H), 3.60 (m, 1H), 3.80 (s, 3H), 4.20 (t, J=7.0, 1H), 4.27 (d, J=7.0, 2H), 7.05 (d, J=8.5, 2H), 7.20 (t, J=5.0, 1H), 7.25–7.90 (m, 11H), 12.50 (br s, 1H).

EXAMPLE 61

Preparation of Nα-(4-Aminobenzenesulfonyl)-Nε-(9-fluorenylmethoxycarbonyl)-L-lysine (Compound No. 106)

The product of example 54 was hydrogenolized following the conditions found in example 4 affording the title compound in 90% yield.

$^1$H NMR (DMSO-d$_6$): 1.12–1.38 (m, 4H), 1.42–1.60 (m, 2H), 2.90 (m, 2H), 3.42 (m, 1H), 4.20 (t, J=7.0, 1H), 4.27 (d, J=7.0, 2H), 5.86 (s, 2H), 6.55 (d, J=8.6, 2H), 7.20 (t, J=5.0, 1H), 7.25–7.90 (m, 11H), 12.35 (br s, 1H).

EXAMPLE 62

Preparation of Nα-(2-Aminobenzenesulfonyl)-Nε-(9-fluorenylmethoxycarbonyl)-L-lysine (Compound No. 105)

The product of example 57 was hydrogenolized following the conditions found in example 4 affording the title compound in 88% yield.

$^1$H NMR (DMSO-d$_6$): 1.12–1.38 (m, 4H), 1.48–1.60 (m, 2H), 2.80 (m, 2H), 3.55 (m, 1H), 4.20 (t, J=7.2, 1H), 4.27 (d, J=7.0, 2H), 5.88 (s, 2H), 6.55 (t, J=7.4, 1H), 6.76 (d, J=7.8, 1H), 7.16 (t, J=5.0, 1H), 7.22 (t, J=7.4, 1H), 7.30–7.92 (m, 10H), 12.60 (br s, 1H).

EXAMPLE 63

Preparation of Nα-(9-Fluorenylmethoxycarbonyl)-Nε-isobutyl-Nε-(4-bromobenzenesulfonyl)-L-lysine (Compound No. 21)

Step A. Preparation of Nα-tert-Butoxycarbonyl-Nε-isobutyl-Nε-(4-bromobenzenesulfonyl)-L-lysine Methyl Ester To a stirred solution of Nα-tert-butoxycarbonyl-Nε-benzyloxycarbonyl-L-lysine methyl ester (380 mg, 1.00 mmol) in MeOH (5 mL) was added 10% Pd/C (70 mg), followed by isobutyraldehyde (91 μL, 2.0 mmol). This suspension was maintained under hydrogen atmosphere for 1 h. The solids were filtered off and to the filtrate was added triethylamine (210 μL, 1.50 mmol) and 4-bromobenzenesulfonyl chloride (765 mg, 3.00 mmol) in 3 portions (1.00 mmol per hour). The reaction mixture was concentrated, diluted with 1N HCl and extracted with EtOAc. The organic layer was dried (MgSO$_4$) and concentrated in vacuo. The residue was purified by flash chromatography eluting with 25% EtOAc in hexane to yield 444 mg (83%) of the title compound.

$^1$H NMR (DMSO-d$_6$): 0.83 (d, J=6.0, 6H), 1.18–1.30 (m, 2H), 1.32–1.48 (m, 2H), 1.37 (s, 9H), 1.50–1.65 (m, 2H), 1.84 (m, 1H), 2.83 (d, J=7.4, 2H), 3.00 (m, 2H), 3.60 (s, 3H), 3.91 (m, 1H), 7.18 (d, J=7.6, 1H), 7.71 (d, J=7.9, 2H), 7.80 (d, J=8.1, 2H).

Step B. Preparation of Nα-(9-Fluorenylmethoxycarbonyl)-Nε-isobutyl-Nε-(4-bromobenzenesulfonyl)-L-lysine The product from step A of this example was reacted utilizing the conditions found in step D of example 38 to yield 67% of the title compound.

$^1$H NMR (DMSO-d$_6$): 0.80 (d, J=, 6H), 1.20–1.50 (m, 4H), 1.52–1.70 (m, 2H), 1.75–1.84 (m, 1H), 2.82 (d, J=7.3, 2H), 3.00 (m, 2H), 3.90 (m, 2H), 4.23 (t, J=6.8, 1H), 4.27 (d, J=6.7, 2H), 7.33 (t, J=7.4, 2H), 7.40 (t, J=7.4, 2H), 7.59 (d, J=8.1, 1H), 7.72 (m, 4H), 7.79 (d, J=8.1, 2H), 7.89 (d, J=7.8, 2H), 12.55 (br s, 1H).

EXAMPLE 64

Preparation of Nα-(9-Fluorenylmethoxycarbonyl)-Nδ-isobutyl-Nδ-(4-bromobenzenesulfonyl)-L-ornithine (Compound No. 41)

Step A. Preparation of Nα-tert-Butoxycarbonyl-Nδ-isobutyl-Nδ-(4-bromobenzenesulfonyl)-L-ornithine Methyl Ester Following the indications of example 63 substituting Nα-tert-butoxycarbonyl-Nε-benzyloxycarbonyl-L-lysine methyl ester with Nα-tert-butoxycarbonyl-Nδ-benzyloxycarbonyl-L-ornithine methyl ester, the title compound was obtained in 72% yield.

$^1$H NMR (DMSO-d$_6$): 0.88 (d, J=6.0, 3H), 0.89 (d, J=6.0, 3H), 1.44 (s, 9H), 1.55–1.88 (m, 4H), 1.90 (h, J=6.1, 1H), 2.86 (d, J=7.5, 2H), 3.10 (d, J=6.3, 2H), 3.73 (s, 3H), 4.25 (br s, 1H), 5.05 (d, J=7.5, 1H), 7.65 (s, 4H).

Step B. Preparation of Nα-(9-Fluorenylmethoxycarbonyl)-Nδ-isobutyl-Nδ-(4-bromobenzenesulfonyl)-L-ornithine.

The product from step A of this example was reacted utilizing the conditions found in step D of example 38 to yield 63% of the title compound.

$^1$H NMR (DMSO-d$_6$): 0.79 (d, J=, 3H), 0.81 (d, J=6.0, 3H), 1.47–1.61 (m, 3H), 1.63–1.76 (m, 1H), 1.85 (h, J=6.1, 1H), 2.81 (d, J=7.3, 2H), 3.05 (m, 2H), 3.92 (m, 1H), 4.22 (t, J=7.2, 1H), 4.28 (d, J=7.2, 2H), 7.28–7.45 (m, 4H), 7.65 (d, J=8.0, 1H), 7.72 (d, J=7.4, 4H), 7.78 (d, J=8.7, 2H), 7.88 (d, J=7.5, 2H), 12.55 (br s, 1H).

EXAMPLE 65

Preparation of Nα-(9-Fluorenylmethoxycarbonyl)-Nε-(2-fluorobenzenesulfonyl)-L-lysine (Compound No. 167)

Nα-(9-fluorenylmethoxycarbonyl)-Nε-tert-butoxycarbonyl-L-lysine (234 mg, 0.50 mmol) was treated with TFA/CH$_2$Cl$_2$ to remove the tert-butoxycarbonyl and the product obtained from evaporating off the volatiles was reacted with 2-fluorobenzenesulfonyl chloride under the conditions indicated in example 2 to afford a 67% yield of the title compound.

¹H NMR (DMSO-d₆): 1.20–1.70 (m, 6H), 2.80 (dd, J=12.8, 6.9, 2H), 3.84 (m, 1H), 4.20 (t, J=7.0, 1H), 4.28 (d, J=6.9, 2H), 7.30–7.57 (m, 7H), 7.66–7.88 (m, 6H), 7.98 (d, J=7.5, 1H).

EXAMPLE 66

Preparation of Nα-(9-Fluorenylmethoxycarbonyl)-Nδ-(1-naphthalenesulfonyl)-L-ornithine (Compound No. 168)

Nα-(9-fluorenylmethoxycarbonyl)-Nδ-tert-butoxycarbonyl-L-ornithine (234 mg, 0.50 mmol) was treated with TFA/CH₂Cl₂ to remove the tert-butoxycarbonyl and the product obtained from evaporating off the volatiles was reacted with 1-naphthalenesulfonyl chloride under the conditions indicated in example 2 to afford a 50% yield of the title compound.

¹H NMR (DMSO-d₆): 1.38–1.62 (m, 3H), 1.65–1.80 (m, 1H), 2.75 (dd, J=13.0, 6.9, 2H), 3.78 (m, 1H), 4.21 (t, J=6.9, 1H), 4.27 (d, J=6.9, 2H), 7.30–7.43 (m, 4H), 7.58 (d, J=7.7, 1H), 7.71 (m, 4H), 7.79 (d, J=8.1, 2H), 7.89 (d, J=7.3, 12), 12.30 (br s, 1H).

EXAMPLE 67

Preparation of (S)-2-(9-Fluorenylmethoxycarbonylamino)-4-(4-bromobenzenesulfonylamino)-butanoic Acid (Compound No. 14)

Step A. Preparation of N-tert-Butoxycarbonyl-L-homoserine Methyl Ester

To a stirred solution of L-homoserine (1.0 g, 8.4 mmol) in dioxane/water (35 mL/70 mL) was added sodium hydroxide (738 mg; 18.5 mmol). After stirring for 5 min, di-tert-butyl dicarbonate (2.20 g, 10.0 mmol) was added in one portion and the mixture was stirred for 2 h and then diluted with 1N HCl (pH~3) and extracted twice with EtOAc. The combined organic layers were dried over magnesium sulfate and concentrated. The crude was diluted in MeOH and CH₂N₂ in ether was added until the yellow colour persisted. Excess diazomethane was destroyed by the addition of AcOH. The mixture was concentrated in vacuo to afford a colorless oil that was flash chromatographed eluting with 60% EtOAc in hexane to yield 1.4 g (71%) of the title compound.

¹H NMR (CDCl₃): 1.43 (s, 9H), 1.60–1.72 (m, 1H), 2.10–2.22 (m, 1H), 2.60–2.76 (m, 2H), 2.74 (s, 3H), 4.50 (br s, 1H), 5.42 (br s, 1H).

Step B. Preparation of (S)-2-tert-Butoxycarbonylamino-4-azido-butanoic Acid Methyl Ester 4-Methylbenzenesulfonyl chloride (572 mg, 3.00 mmol) was added to a stirred solution of the product of step A of this example in a mixture of pyridine/CH₂Cl₂ (7.5 mL/7.5 mL). The mixture was stirred at room temperature until complete disappearance of the starting material and was then diluted with 10% HCl, and extracted with CH₂Cl₂. The organic layer was dried over MgSO₄ and concentrated in vacuo. The residue was diluted in DMF to which was added sodium azide (260 mg, 4.00 mmol). The suspension was heated at 70° C.for 3 h, cooled to room temperature, diluted with 1N HCl and extracted with EtOAc. The organic layer was washed with brine, dried over MgSO₄ and concentrated in vacuo. The residue was purified by flash chromatography eluting with 30% EtOAc in hexane to afford 470 mg (91%) of the title compound.

¹H NMR (CDCl₃): 1.42 (s, 9H), 1.82–1.92 (m, 1H), 2.07–2.15 (m, 1H), 3.38 (t, J=6.0, 2H), 3.74 (s, 3H), 4.38 (br s, 1H), 5.24 (br s, 1H).

Step C. Preparation of Methyl (S)-2-tert-Butoxycarbonylamino-4-(4-bromobenzenesulfonylamino) butanoate To a stirred solution of the product of step B of this example (520 mg, 2.00 mmol) in EtOAc (6 mL) was added 10% Pd/C (60 mg). The suspension was stirred under hydrogen for 1 h, filtered and concentrated in vacuo. The residue was diluted with THF (6 mL) and 4-bromobenzenesulfonyl chloride (613 mg, 2.40 mmol) was added followed by triethylamine (557 µL, 4.00 mmol). The mixture was stirred for 3 h and then acidified with 1N HCl and extracted with EtOAc. The organic layer was dried over MgSO₄ and concentrated in vacuo. The crude material was purified by flash chromatography eluting with 30% EtOAc in hexane to afford 770 mg (85%) of the title compound.

¹H NMR (DMSO-d₆): 1.35 (s, 9H), 1.65–1.72 (m, 1H), 1.75–1.85 (m, 1H), 2.35–2.42 (m, 2H), 3.90 (m, 1H), 7.10 (d, J=6.3, 1H), 7.70 (d, J=7.0, 2H), 7.80 (d, J=7.0, 2H), 12.40 (br s, 1H).

Step D. Preparation of (S)-2-(9-Fluorenymethoxycarbonylamino)-4-(4-bromobenzenesulfonylamino)-butanoic Acid A solution of the product of step C of this example (225 mg, 0.50 mmol) in TFA/CH₂Cl₂ (2 mL/2 mL) was stirred for 2 h, then concentrated under reduced pressure. The residue was dissolved in THF/H₂O (1 mL/1 mL) to which was added sodium carbonate (159 mg, 1.50 mmol) and 9-fluorenylmethyl chloroformate (155 mg, 0.60 mmol). The mixture was stirred for 1 h, then 1M sodium hydroxide (0.5 mL) was added. After stirring for 30 min, the reaction mixture was acidified with 1N HCl and extracted twice with EtOAc. The combined organic layers were dried over MgSO₄ and concentrated in vacuo. The residue was purified by flash chromatography eluting with 5% MeOH in CH₂Cl₂ to afford 187 mg (67%) of the title compound.

¹H NMR (DMSO-d₆): 1.70–1.80 (m, 1H), 1.82–1.90 (m, 1H), 2.78–2.87 (m, 2H), 3.95 (m, 1H), 4.18–4.27 (m, 3H), 7.28–7.45 (m, 4H), 7.50 (d, J=7.0, 1H), 7.72–7.92 (m, 9H).

EXAMPLE 68

Preparation of (S)-2-(9-Fluorenylmethoxycarbonylamino)-3-(4-bromobenzenesulfonylamino)-propanoic Acid (Compound No. 18)

Step A. Preparation of (S)-tert-Butoxycarbonylamino-β-propiolactone

DEAD (1.76 g, 10.0 mmol) was added to a cold (−78° C.) solution of triphenylphosphine (2.62 g, 10.0 mmol) in THF (30 mL). The mixture was stirred for 15 min and a solution of tert-butoxycarbonyl-L-serine (2.05, 10.0 mmol) in acetonitrile (10 mL) was added. The mixture was stirred for 30 min then allowed to warm up to room temperature. The solvent was then removed under reduced pressure and the crude was purified by flash chromatography eluting with 30% EtOAc in hexane to afford 1.37 g (73%) of the title compound.

¹H NMR (CDCl₃): 1.43 (s, 9H), 4.40–4.50 (m, 2H), 5.10 (br s, 1H), 5.45 (br s, 1H).

Step B. Preparation of (S)-2-tert-Butoxycarbonylamino-3-(4-bromobenzenesulfonylamino)-propionic Acid To a stirred solution of the product prepared in step A of this example (561 mg, 4.00 mmol) in CH₃CN (2 0 mL) was added NH₃ (2M solution in EtOH, 10 mL). The mixture was stirred at 0° C. for 2 h and then at room temperature. After 3 h, it was concentrated and rediluted with dioxane (10 mL). To this solution was added 4-bromobenzenesulfonyl chloride (2.04 g, 8.00 mmol) followed by 1M Na₂CO₃ (8 mL).

The reaction mixture was vigorously stirred for 2 h and then acidified with 1N HCl and extracted with EtOAc. The organic layer was dried over MgSO$_4$ and concentrated in vacuo. The crude material was purified by flash chromatography eluting with 5% MeOH in CH$_2$Cl$_2$ containing 0.5% AcOH, affording 500 mg (30%) of the title compound.

$^1$H NMR (DMSO-d$_6$): 1.34 (s, 9H), 2.96–3.12 (m, 2H), 3.90 (m, 1H), 6.65 (br s, 1H), 7.70 (d, J=7.2, 2H), 7.80 (d, J=7.0, 2H).

Step C. Preparation of (S)-2-(9-Fluorenylmethoxycarbonylamino)-3-(4-bromobenzenesulfonylamino)-propionic Acid A solution of the acid prepared in step B of this example (50 mg, 0.12 mmol) in TFA/CH$_2$Cl$_2$ (1 mL/1 mL) was stirred for 1 h and concentrated in vacuo. The residue was taken up in a mixture of 1M Na$_2$CO$_3$ and dioxane (1 mL/1 mL), to which was added 9-fluorenylmethyl chloroformate (37 mg, 0.10 mmol). The reaction mixture was stirred for 1 h and then diluted with 1N HCl and extracted with EtOAc. The organic layers were dried over MgSO$_4$ and concentrated in vacuo. The residue was purified by flash chromatography eluting with 10% MeOH in CH$_2$Cl$_2$ containing 1% AcOH affording 42 mg (62%) of the title compound.

$^1$H NMR (DMSO-d$_6$): 2.95–3.03 (m, 1H), 3.08–3.15 (m, 1H), 3.78–3.85 (m, 1H), 4.20–4.31 (m, 3H), 7.00 (br s, 1H), 7.25–7.50 (m, 4H), 7.68–7.92 (mn, 9H), 12.30 (br s, 1H).

EXAMPLE 69

Preparation of Nα-Isobutyl-Nα-(4-nitrobenzenesulfonyl)-Nε-(3-indolepropionyl)-L-lysine (Compound No. 95)

Step A. Preparation of L-Nα-Isobutyl-ε-caprolactam L-α-amino-ε-caprolactam (6.0 g, 47 mmol) was dissolved in MeOH (300 mL) containing AcOH (3.5 mL). Isobutyraldehyde (3.0 g, 50 mmol) was added to the solution followed by sodium cyanoborohydride (3.3 g, 50 mmol). The mixture was stirred at room temperature for 2 h after which MeOH was removed in vacuo. 1M K$_2$CO$_3$ (30 mL) was added to the residue which was then extracted with two 100 mL portions of EtOAc. The organic layer was dried with MgSO$_4$, filtered and concentrated in vacuo. The crude residue, which contains traces of dialkylated product was taken up in hot EtOH (8 mL) and diluted with 300 mL ice cold ether until two phases began to appear. 10 mL of trimethylsilyl chloride was then added slowly which gave a precipitate of pure product which was filtered and dried under vacuum affording 9.57 g (95%) of the title compound as the HCl salt. The salt was suspended in 200 mL EtOAc and 20% NaOH slowly until the solid disappears. The organic layer was dried with MgSO$_4$ and concentrated in vacuo to give 7.55 g (91%) of a thick oil which crystallized on standing. NP 52–54° C.

$^1$H NMR (CDCl$_3$): 0.93 (d, J=6.8, 3H), 0.97 (d, J=6.5, 3H), 1.39 (t, J=9.8, 1H), 1.47 (m, 1H), 1.61 (m, 1H), 1.65–1.78 (m, 2H), 1.93–2.01 (m, 2H), 2.20–2.32 (m, 2H), 2.38 (t, J=9.7, 1H), 3.16 (m, 3H), 6.62 (s, 1H).

Step B. Preparation of L-Nα-Isobutyl-Nα-(4-nitrobenzenesulfonyl)-ε-caprolactam

To the product from step A of this example (4.14 g, 22.5 mmol) dissolved in CH$_2$Cl$_2$ (50 mL) was added diisopropylethyl amine (6.00 mL, 30.0 mmol) and 4-nitrobenzenesulfonyl chloride (5.09 g, 23.0 mmol). The mixture was stirred overnight. Afterwards, the solution was acidified with 1N HCl and extracted with EtOAc. The organic layer was dried and concentrated in vacuo. The residue was recrystallized from MeOH. The thin needles were filtered off and air dried giving 6.9 g (83%) of the pure title product. MP 152–154° C.

$^1$H NMR (CDCl$_3$): 0.93 (d, J=6.0, 3H), 0.96 (d, J=6.0, 3H), 1.39 (t, J=12.0, 1H), 1.65–1.85 (m, 3H), 2.08–2.18 (m, 3H), 3.06 (dd, J=14.3, 8.5, 1H), 3.35 (dd, J=14.2, 8.5, 1H), 4.65 (d, J=8.7, 1H), 5.7 (s, 1H), 7.92 (d, J=8.8, 2H), 8.3 (d, J=8.8, 2H).

Step C. Preparation of Nα-Isobutyl-Nα-(4-nitrobenzenesulfonyl)-L-lysine Hydrochloride The product of step B of this example (1.0 g, 2.7 mmol) was dissolved in AcOH (4 mL). This solution is added to 12N HCl and the mixture was refluxed for 2 h until all solids had disappeared. The solution was evaporated in vacuo to give 1.12 g (quantitative yield) of the desired product as its hydrochloride salt.

$^1$H NMR (DMSO-d$_6$+10% D$_2$O): 0.79 (d, J=6.8, 3H), 0.86 (d, J=6.8, 3H), 1.25 (t, J=11.9, 2H), 1.28–1.32 (m, 2H), 1.45–1.51 (m, 2H), 1.75–1.85 (m, 2H), 1.70 (m, 1H), 2.83–2.87 (m, 1H), 3.03–3.07 (m, 1H), 4.21 (t, J=10.1, 1H), 8.10 (d, J=7.9, 2H), 8.37 (d, J=7.9, 2H).

Step D. Preparation of Nα-Isobutyl-Nα-(4-nitrobenzenesulfonyl)-Nε-(3-indolepropionyl)-L-lysine The product of step C of this example (100 mg, 0.24 mmol) was weighed in the Bohdahn robotic reaction vessels. 3.3 M Cs$_2$CO$_3$ (1 mL) and THF (2 mL) were then added. The tube was then stirred vigorously and indole-3-proprionic acid (80 mg, 0.4 mmol), activated by carbonyl diimidazole (65 mg, 0.4 mmol) in THF (1 mL), was added. Gas evolution was observed. The stirring continued for 2 h. EtOAc (3 mL) was then added and the organic phase was removed. This phase was washed with 1N HCl and the organic phase was concentrated in vacuo giving a very crude product which was purified by flash chromatography to yield 140 mg of the title product (90%).

$^1$H NMR (DMSO-d$_6$): 0.79 (d, J=6.8, 3H), 0.86 (d, J=6.8, 3H), 0.91 (m, 1H), 1.25 (t, J=10.6, 2H), 1.28–1.34 (mn, 2H), 1.45–1.52 (mn, 2H), 1.75–1.85 (m, 2H), 2.35 (t, J=7.1, 2H), 2.60 (t, J=7.1, 2H), 2.85–3.05 (m, 2H), 4.18 (t, J=5.2, 1H), 6.85–6.91 (m, 1H), 6.96–7.11 (m, 3H), 7.22–7.31 (m, 2H), 7.45 (d, J=7.9, 2H), 7.67 (d, J=7.9, 2H).

EXAMPLE 70

Preparation of Nα-(9-Fluorenylmethoxycarbonyl)-Nε-(4-bromobenzenesulfonyl)-L-lysine Methyl Ester (Compound No. 15)

A solution of diazomethane in ether was added to a solution of N-α-(9-fluorenylmethoxycarbonyl)-Nε-(4-bromobenzenesulfonyl)-L-lysine (35 mg, 0.06 mmol) in MeOH (0.5 mL) until the yellow color persisted. The solvents were removed in vacuo and the residue was purified by flash chromatography eluting with 5% MeOH in CH$_2$Cl$_2$, affording 20 mg (55%) of the title compound.

$^1$H NMR (DMSO-d$_6$): 1.20–1.40 (mn, 4H), 1.51–1.65 (m, 2H), 2.70 (dd, J=12.3, 6.0, 2H), 3.61 (s, 3H), 3.95 (dd, J=13.0, 6.1, 2H), 4.20 (t, J=7.0, 1H), 4.30 (d, J=7.0, 2H), 7.30–7.42 (m, 4H), 7.68–7.72 (m, 4H), 7.80 (d, J=8.1, 2H), 7.88 (d, J=8.1, 2H).

EXAMPLE 71

Preparation of (2S)-(9-Fluorenylmethoxycarbonylamino)-6-(4-bromobenzenesulfonylamino)-1-hexanol (Compound No. 22)

Step A. Preparation of (2S)-tert-Butoxycarbonylamino-6-(4-bromobenzenesulfonylamino)-1-hexanol To a cold (0° C.) solution of the ester (240 mg, 0.50 mmol) in ether (4 mL) was added in one portion LiAlH$_4$ (76 mg, 2.0 mmol). The reaction mixture was stirred at 0° C. for 1 h and at room temperature for an additional 30 min The mixture was quenched with water and 1N HCl and extracted with EtOAc. The organic extract was dried over $MgSO_4$ and concentrated in vacuo. The residue was purified by flash chromatography eluting with 30% EtOAc in hexane to provide 207 mg (92%) of the title compound.

$^1$H NMR (DMSO-$d_6$): 1.30–1.58 (m, 6H), 1.43 (s, 9H), 2.92 (dd, J=12.4, 6.5, 2H), 2.70 (br s, 1H), 3.50–3.68 (m, 2H), 4.80 (d, J=7.1, 1H), 5.30 (t, J=8.2, 1H), 7.63 (d, J=8.2, 2H), 7.72 (d, J=8.0, 2H).

Step B. Preparation of (2S)-(9-Fluorenylmethoxycarbonylamino)-6-(4-bromobenzenesulfonylamino)-1-hexanol.

A solution of the alcohol from step A of this example in $TFA/CH_2Cl_2$ (1 mL/1 mL) was stirred for 1 h and then concentrated in vacuo. The residue was taken up in a mixture of THF and 1M $K_2CO_3$ (1 ml/1 mL). To this solution was added 9-fluorenylmethyl chloroformate (103 mg, 0.40 mmol) and the mixture was stirred at room temperature for 1 h. The reaction was quenched by adding 1N HCl and was extracted with EtOAc. The organic extracts were washed with brine, dried over $MgSO_4$ and concentrated in vacuo. The residue was purified by flash chromatography eluting with 50% EtOAc in hexane, providing 142 mg (75%) of the title compound.

$^1$H NMR (DMSO-$d_6$): 1.12–1.50 (m, 6H), 2.70 (dd, J=12.8, 6.8, 2H), 3.18–3.22 (m, 1H), 3.27–3.36 (m, 1H), 4.19–4.30 (m, 3H), 4.58 (t, J=5.4, 1H), 6.92 (d, J=8.5, 1H), 7.25–7.42 (m, 4H), 7.65–7.73 (m, 5H), 7.80 (d, J=8.6, 2H), 7.86 (d, J=8.0, 2H).

EXAMPLE 72

Preparation of (2R,2S)-(9-Fluorenylmethoxycarbonylamino)-6-(4-bromobenzenesulfonylamino)-1-hexanamide (Compound No. 20)

Step A. Preparation of (2R,2S)-tert-Butoxycarbonyl-6-(4-bromobenzenesulfonylamino)-1-hexanamide To a stirred solution of methyl (2R,2S)-tert-butoxycarbonyl-6-(4-bromobenzenesulfonylamino)-1-hexanoate (415 mg, 1.00 mmol) in THF (5 mL) was added ammonium hydroxide (3 mL) and sodium hydroxide (3 mL). The mixture was stirred for 2 h, diluted with 1N HCl until acidic and extracted twice with EtOAc. The extracts were dried over $MgSO_4$ and concentrated in vacuo. Purification by flash chromatography eluting with 5% MeOH in $CH_2Cl_2$ afforded 350 mg (82%) of the title compound.

$^1$H NMR (DMSO-$d_6$): 1.44 (s, 9H), 1.47–1.90 (m, 6H), 3.20 (m, 2H), 4.12 (br s, 1H), 5.03 (m, 1H), 5.20 (br s, 1H), 5.88 (br s, 1H), 6.30 (br s, 1H), 7.20–7.45 (m, 4H).

Step B. Preparation of (2R,2S)-(9-Fluorenylmethoxycarbonylamino)-6-(4-bromobenzenesulfonylamino)-1-hexanamide The tert-butoxycarbonyl was removed as indicated in example 24 and the resulting salt was treated with N-(9-fluorenylmethoxycarbonyloxy) succinimide as in step D of example 38 to afford the title product in 67% yield.

$^1$H NMR (DMSO-$d_6$): 1.15–1.62 (m, 6H), 2.70 (dd, J=12.6, 6.5, 2H), 3.85 (m, 1H), 4.20–4.35 (m, 3H), 6.94 (s, 1H), 7.24 (s, 1H), 7.28–7.42 (m, 4H), 7.68–7.90 (m, 8H).

EXAMPLE 73

Preparation of Nα-Benzoyl-Nε-(4-bromobenzenesulfonyl)-L-lysine (Compound No. 65)

Step A. Preparation of Nα-tert-butoxycarbonyl-Nε-(4-bromobenzenesulfonylamino)-L-lysine Methyl Ester The title compound was prepared by reacting Nα-tert-butoxycarbonyl-Nε-(4-benzyloxycarbonyl)-L-lysine with diazomethane using conditions similar to those found in example 70. The product was then hydrogenolyzed ($H_2$, 10% Pd/C, MeOH) following indications of example 4. The product was treated under the conditions of example 2 to provide after purification by flash chromatography the title compound (72% yield).

$^1$H NMR (DMSO-$d_6$): 1.32–1.42 (m, 2H), 1.45 (s, 9H), 1.47–1.62 (m, 3H), 1.68–1.72 (m, 2H), 2.95 (dd, J=13.0, 6.4, 2H), 3.74 (s, 3H), 4.28 (br s, 1H), 4.80 (t, J=5.3, 1H), 5.07 (br s, 1H), 7.66 (d, J=8.3, 2H), 7.73 (d, J=8.5, 2H).

Step B. Preparation of Nα-Benzoyl-Nε-(4-bromobenzenesulfonyl)-L-lysine

The product from step A of this example (0.30 mmol) was taken up in a mixture of $TFA/CH_2Cl_2$ (1 mL/1 mL) for 1 h and the solution was concentrated to dryness. The crude product was dissolved in DMF (2 mL) to which was added benzoic acid, the BOP reagent (159 mg, 0.36 mmol) and DEFA (156 µL, 0.90 mmol). The reaction mixture was stirred overnight and then quenched with $^1$N HCl and extracted with EtOAc. The organic extract was washed with brine and concentrated in vacuo. The residue was dissolved in THF to which was added $^1$N NaOH (0.3 mL). The mixture was stirred for 2 h and 1N HCl was added. The mixture was extracted with EtOAc, washed with brine, dried over $MgSO_4$ and concentrated in vacuo. The crude material was purified by flash chromatography to yield the title compound in 83% yield.

$^1$H NMR (DMSO-$d_6$): 1.30–1.47 (m, 4H), 1.57–1.70 (m, 2H), 2.73 (dd, J=11.5, 6.1, 2H), 4.31 (dd, J=13.1, 7.7, 1H), 7.42–7.55 (m, 3H), 7.65–7.90 (m, 7H), 8.52 (d, J=7.6, 1H), 12.40 (br s, 1H).

EXAMPLE 74

Preparation of Nα-(4-hydroxy-7-trifluoromethylquinoline-3-carbonyl)-Nε-(4-bromobenzenesulfonyl)-L-lysine (Compound No. 23)

Following the indications of example 73 and substituting benzoic acid by 4-hydroxy-7-trifluoromethylquinoline-3-carboxylic acid, the title compound was obtained in 25% yield.

$^1$H NMR (DMSO-$d_6$): 1.22–1.57 (m, 4H), 1.65–1.82 (m, 2H), 2.70 (m, 2H), 4.46 (m, 1H), 7.67–7.82 (m, 7H), 8.08 (s, 1H), 8.45 (d, J=8.5, 1H), 10.25 (d, J=7.5, 1H), 12.80 (br s, 1H).

EXAMPLE 75

Preparation of Nα-(9-Fluorenemethylcarbonyl)-Nε-(4-bromobenzenesulfonyl)-L-lysine (Compound No. 30)

Following the indications of example 73 and substituting benzoic acid by 9-fluoreneacetic acid, the title compound was obtained in 71% yield.

$^1$H NMR (DMSO-$d_6$): 1.22–1.45 (m, 4H), 1.47–1.55 (m, 1H), 1.62–1.70 (m, 1H), 2.58 (dd, J=14.5, 6.5, 2H), 2.70–2.74 (m, 2H), 4.25 (m, 1H), 4.34 (t, J=7.5, 1H), 7.20–7.38 (m, 4H), 7.48 (d, J=7.5, 1H), 7.60 (d, J=7.5, 1H), 7.70–7.90 (m, 6H), 8.12 (d, J=6.6, 1H), 12.50 (br s, 1H).

EXAMPLE 76

Preparation of Nα-(9-Fluorenecarbonyl)-Nε-(4-bromobenzenesulfonyl)-L-lysine (Compound No. 38)

Following the indications of example 73 and substituting benzoic acid by 9-fluoreneacetic acid, the title compound was obtained in 71% yield. The NMR indicates a 1:1 equilibrium between the amide form and its enol form.

$^1$H NMR (DMSO-d$_6$): 1.26–1.45 (m, 4H), 1.72–1.80 (m, 2H), 2.72 (m, 2H), 4.18 (dd, J=12.5, 6.5, 0.5H), 4.25 (dd, J=12.5, 0.5H), 6.76 (s, 0.5H, fluorene methine), 7.22–7.30 (m, 2H), 7.32–7.43 (m, 3H), 7.53 (d, J=7.6, 0.5H), 7.56 (d, J=7.5, 0.5H), 7.68–7.80 (m, 7H), 8.15 (d, J=8.4, 0.5H), 8.26 (d, J=8.0, 0.5H), 12.21 (br s, 0.5H, OH, enol), 12.71 (br s, 1H).

EXAMPLE 77

Preparation of Nα-(Diphenylhydroxyacetyl)-Nε-(4-bromobenzenesulfonyl)-L-lysine (Compound No. 37)

Following the indications of example 73 and substituting benzoic acid by benzilic acid, the title compound was obtained in 55% yield.

$^1$HNMR(DMSO-d$_6$): 1.13–1.20 (m, 2H), 1.28–1.37 (m, 2H), 1.60–1.75 (m, 2H), 2.65 (dd, 12.5, 6.1, 2H), 4.22 (dd, J=12.7, 7.8, 2H), 6.83 (s, 1H), 7.20–7.42 (m, 11H), 7.65 (t, J=5.5, 1H), 7.70 (d, J=8.1, 2H), 7.80 (d, J=8.1, 2H), 8.04 (d, J=8.3, 1H), 12.70 (br s, 1H).

EXAMPLE 78

Preparation of Nα-(Diphenylacetyl)-Nε-(4-bromobenzenesulfonyl)-L-lysine (Compound No. 36)

Following the indications of example 73 and substituting benzoic acid by diphenylacetic acid, the title compound was obtained in 67% yield.

$^1$HNMR(DMSO-d$_6$): 1.18–1.25 (m, 4H), 1.48–1.68 (m, 2H), 2.67 (dd, J=12.3, 6.3, 2H), 4.17 (dd, J=12.1, 7.3, 1H), 5.05 (s, 1H), 7.17–7.30 (m, 10H), 7.65 (t, J=5.3, 1H), 7.70 (d, J=8.4, 2H), 7.80 (d, J=8.3, 2H), 8.51 (d, J=8.3, 2H), 12.50 (br s, 1H).

EXAMPLE 79

Preparation of Nα-(3-Indoleacetyl)-Nε-(4-bromobenzenesulfonyl)-L-lysine (Compound No. 29)

Following the indications of example 73 and substituting benzoic acid by 3-indoleacetic acid, the title compound was obtained in 32% yield.

$^1$H NMR (DMSO-d$_6$): 1.20–1.40 (m, 4H), 1.45–1.70 (m, 2H), 2.70 (dd, J=12.5, 7.5, 2H), 3.55 (d, J=11.2, 2H), 4.10 (dd, J=12.5, 7.4, 1H), 6.90–7.05 (m, 2H), 7.18 (s, 1H), 7.30 (d, J=7.8, 1H), 7.52 (d, J=7.7, 1H), 7.68–7.75 (m, 3H), 7.80 (d, J=8.1, 2H), 8.05 (d, J=7.1, 1H), 10.82 (br s, 1H).

EXAMPLE 80

General Preparation of Nα-Alkyl-Nα-(Substituted Benzenesulfonyl)-Nε-benzyloxycarbonyl-L-lysine Benzyl Ester The products of reductive alkylation with isobutyraldehyde (BSP-4), 2-ethylbutyraldehyde (BSP-5) and 2-methylpentanaldehyde (BSP-6) are dissolved in CH$_2$Cl$_2$ at a concentration of 100 mg/mL and a volume of 8 mL. The three solutions are added (1 mL aliquots) to 24 reactor block tubes in the Bohdahn AWS and purged with argon. A solution of 400 mg DIPEA in 10 mL CH$_2$Cl$_2$ is made and aliquots of 1 ml are placed in all the tubes. The solution is stirred for 20 min The solutions of substituted sulfonyl chlorides are added in 2 mL aliquots. The concentrations are as follows:

| Substituted benzenesulfonyl chloride | Concentration in CH$_2$Cl$_2$ |
|---|---|
| tosyl chloride | 25 mg/mL |
| benzenesulfonyl chloride | 25 mg/mL |
| trans-β-styrenesulfonyl chloride | 25 mg/mL |
| acetamidobenzenesulfonyl chloride | 25 mg/mL |
| methoxybenzenesulfonyl chloride | 25 mg/mL |
| bromobenzenesulfonyl chloride | 30 mg/mL |
| 4-nitrobenzenesulfonyl chloride | 30 mg/mL |
| 2-nitrobenzenesulfonyl chloride | 30 mg/mL |

The solutions were then subjected to a gentle reflux and the CH$_2$Cl$_2$ was reduced to about 0.5 mL. The solutions were stirred under argon for 72 h. The CH$_2$Cl$_2$ was then removed in vacuo and replaced with 1 ml of acetone. 2 mL of 1M K$_2$CO$_3$ was then added and the tubes shaken manually. CH$_2$Cl$_2$ (4 mL) was added and the organic phase was separated and evaporated off. A small aliquot was the provided for LC-MS.

| Compound no. | MASS | YIELD mg | LC-MS purity (%) |
|---|---|---|---|
| 75 | 580.73 | 145 | >90 |
| 169 | 566.71 | 122 | >90 |
| 170 | 596.73 | 136 | >90 |
| 76 | 592.75 | 85 | >90 |
| 77 | 623.76 | 137 | >90 |
| 171 | 645.6 | 210 | >90 |
| 79 | 611.71 | 116 | >90 |
| 78 | 611.71 | 106 | >90 |
| 80 | 608.79 | 140 | >90 |
| 172 | 594.76 | 112 | >90 |
| 173 | 624.79 | 139 | >90 |
| 175 | 620.80 | 125 | >90 |
| 174 | 651.81 | 129 | >90 |
| 176 | 673.66 | 131 | >90 |
| 177 | 639.76 | 110 | >90 |
| 178 | 639.76 | 129 | Impure |
| 88 | 608.79 | 124 | >90 |
| 179 | 594.76 | 128 | >90 |
| 180 | 624.79 | 125 | >90 |
| 181 | 620.8 | 112 | >80 |
| 182 | 651.81 | 134 | >90 |
| 183 | 673.66 | 117 | >90 |
| 184 | 639.76 | 101 | ≅60 |
| 185 | 639.76 | 84 | Impure |

In some cases some DIPEA remained. Excess tosylate was hydrolyzed and extracted during work up.

EXAMPLE 81

Preparation of Nα-Isobutyl-Nα-(4-methylbenzenesulfonyl)-Nε-acyl-L-lysine

Nα-isobutyl-Nα-(4-methylbenzenesulfonyl)-L-lysine acetate salt, was weighed in Bohdahn robotic reaction vessels. The mass varied from 80 to 100 mg. These were then suspended in a 3.3M Cs$_2$CO$_3$ solution and THF (2 mL) was added. This formed a white suspension. The tubes were then stirred vigorously and the various acid chlorides dissolved in THF (1 mL) were added. In most cases gas evolution was observed. The stirring continued for 2 h.

Initial Weights:

| Product no. | Starting material mg | mmol | Carboxylic acid chloride mg (Carboxylic acid precursors) |
|---|---|---|---|
| 83 | 105 | 0.25 | 60 (9-Fluorenecarboxylic acid) |
| 84 | 94 | 0.22 | 73 (9-Fluoreneacetic acid) |
| 85 | 106 | 0.25 | 73 (Xanthene-9-carboxylic acid) |
| 86 | 87 | 0.21 | 70 (Diphenylacetic acid) |
| 87 | 81 | 0.2 | 60 (Indolyl-3-carboxylic acid) |
| 88 | 83 | 0.2 | 60 (Indolyl-2-carboxylic acid) |
| 89 | 93 | 0.22 | 60 (3-Indolepropionic acid) |
| 90 | 88 | 0.21 | 60 (trans-Cinnamic acid) |
| 91 | 86 | 0.21 | 60 (3-Phenylpropionic acid) |
| 92 | 87 | 0.21 | 112 (Cholesteryl chloroformate) |
| 93 | 86 | 0.21 | 60 (2-Quinolinecarboxylic acid) |

After 2 h, EtOAc (3 mL) was added to each flask and the two phases were separated. In the case of the reaction producing derivatives no. 90, 92, 95 and 96, an insoluble precipitate was formed. These were acidified with 1N HCl which gave two clear phases. The organic layers were separated and evacuated to leave the crude products as either acids or as the cesium salt. These were placed under high vacuum for 16 h. The flasks were weighed and tabulated above. The products were then analysed by MS to determine if the reaction had taken place and to get an estimate of the purity of the final adducts.

Results:

| Product no. | Yield | MW | % purity |
|---|---|---|---|
| 83 | 98 | 548.69 | >50 |
| 84 | 89 | 562.72 | >85 |
|  |  | 694.72 (Cs) |  |
| 85 | 95 | 564.69 | >85 |
| 86 | 90 | 550.71 | >85 |
|  |  | 682.71 (Cs) |  |
| 87 | 123 | 499.62 | >50 |
| 88 | 91 | 499.62 | >50 |
|  |  | 631.62 (Cs) |  |
| 89 | 101 | 527.68 | >85 |
| 90 | 105 | 486.62 | >85 |
|  |  | 618.62 (Cs) |  |
| 91 | 97 | 488.64 | >80 |
|  |  | 620.64 (Cs) |  |
| 92 | 115 | 511.63 | >85 |
|  |  | 643.63 (Cs) |  |
| 93 | 112 | 769.13 | >85 |
|  |  | 900.14 (Cs) |  |

EXAMPLE 82

Preparation of Nα-Isobutyl-Nα-(4-methylbenzenesulfonyl)-Nε-(9-fluorenylmethoxycarbonyl)-L-lysine Methyl Ester (Compound No. 123)

The product from example 45 was treated with excess diazomethane, yielding the title compound in 68% yield.

$^1$H NMR (DMSO-$d_6$): 0.84 (d, J=7.1, 3H), 0.87 (d, J=7.0, 3H), 1.35–1.65 (m, 5H), 1.90–2.00 (m, 2H), 2.40 (s, 3H), 2.95 and 3.04 (ABX, J=14.3, 7.7, 2H), 3.18 (m, 2H), 3.49 (s, 3H), 4.20 (t, J=7.0, 1H), 4.40 (m, 2H), 4.85 (t, J=5.5, 1H), 7.23–7.40 (m, 6H), 7.55–7.80 (m, 6H).

EXAMPLE 83

Preparation of (2R)-N-Isobutyl-N-(4-methylbenzenesulfonylamino)-6-(9-fluorenylmethoxycarboxylamino)-1-hexanol (Compound No. 124)

Step A. Preparation of (2R)-N-Isobutyl-N-(4-methylbenzenesulfonylamino)-6-(9-fluorenylmethoxycarbonylamino)-1-hexanol The product from example 35 step C was treated under conditions described in example 71 step 1 to yield the title compound in 92% yield.

$^1$H NMR (DMSO-$d_6$): 0.90 (d, J=6.5, 3H), 0.92 (d, J=6.7, 3H), 1.25–1.50 (m, 5H), 1.88–2.00 (m, 2H), 2.39 (s, 3H), 2.90 (dd, J=14.5, 7.5, 1H), 2.95–3.10 (m, 3H), 3.50–3.65 (m, 3H), 4.80 (br s, 1H), 5.10 (s, 2H), 7.26 (d, J=7.3, 2H), 7.30–7.40 (m, 5H), 7.68 (d, J=7.8, 2H).

Step B. Preparation of (2R)-N-Isobutyl-N-(4-methylbenzenesulfonylamino)-6-(9-fluorenylmethoxycarboxylamino)-1-hexanol The alcohol of step A of this example (150 mg, 0.31 mmol) was dissolved in MeOH (3 mL) and hydrogenated in the presence of 10% Pd/C (50 mg). After 1 h, N-(9-fluorenylmethoxycarbonyloxy) succinimide (177 mg, 0.34 mmol) and triethylamine (62 mg, 0.62 mmol) were added. The reaction mixture was stirred at room temperature for 1 h, then filtered and concentrated in vacuo. The residue was purified by flash chlormatography eluting with 70% EtOAc in hexane to provide 90% yield of the title compound.

$^1$H NMR (DMSO-$d_6$): 0.82 (d, J=7.0, 3H), 0.84 (d, J=7.0, 3H), 0.90–1.30 (m, 5H), 1.45–1.55 (m, 1H), 1.82–1.90 (m, 1H), 2.36 (s, 3H), 2.53 (s, 1H), 2.78 and 2.95 (ABX, J=15.0, 7.5, 2H), 2.82 (m, 2H), 3.26 and 3.55 (ABX, J=14.0, 7.0, 2H), 3.50 (m, 1H), 4.20 (t, J=7.0, 1H), 4.30 (t, J=7.0, 2H), 7.18 (t, J=5.0, 1H), 7.30–7.42 (m, 6H), 7.65 (m, 4H), 7.90 (d, J=7.4, 2H).

EXAMPLE 84

Preparation of (2R,2S)-N-Isobutyl-N-(4-methylbenzenesulfonylamino)-6-(9-fluorenylmethoxycarboxylamino)-1-hexanamide (Compound No. 125)

Step A. Preparation of (2R,2S)-N-Isobutyl-N-(4-methylbenzenesulfonylamino)-6-benzyloxycarbonylamino-1-hexanamide To a stirred solution of the product of example 35 step D (245 mg, 0.50 mmol) in DMF (4 mL) was added successively ammonium chloride (106 mg, 2.00 mmol), triethylamine (202 mg, 2.00 mmol) and EDC.HCl. The reaction mixture was stirred for 36 h, then quenched with water and extracted with EtOAc. The organic layer was dried over MgSO$_4$, concentrated and purified by flash chromatography, eluting with 10% MeOH in CH$_2$Cl$_2$, affording 190 mg (77%) of the title compound.

$^1$H NMR (DMSO-$d_6$): 0.80 (d, J=7.0, 3H), 0.81 (d, J=7.0, 3H), 1.00–1.32 (m, 5H), 1.60–2.00 (m, 2H), 2.37 (s, 3H), 2.85 (m, 2H), 2.90 and 3.17 (ABX, J=13.5, 7.5, 2H), 4.10 (t, J=7.2, 1H), 5.00 (s, 2H), 7.07 (s, 1H), 7.14 (s, 1H), 7.16 (m, 1H), 7.30–7.40 (m, 7H), 7.71 (d, J=7.8, 2H).

Step B. Preparation of (2R,2S)-N-Isobutyl-N-(4-methylbenzenesulfonylamino)-6-(9-fluorenylmethoxycarbonylamino)-1-hexanamide The title product was obtained in 61% yield by following the indications of step B of example 83, substituting the hexanol derivative by the product obtained in step A of this example.

$^1$H NMR (DMSO-$d_6$): 0.79 (d, J=6.5, 3H), 0.82 (d, J=6.5, 3H), 1.00–1.35 (m, 5H), 1.60–1.99 (m, 2H), 2.37 (s, 3H), 2.85 (m, 2H), 2.90 and 3.20 (ABX, J=13.5, 7.5, 2H), 4.10 (t, J=7.1, 1H), 4.20 (t, J=7.0, 1H), 4.27 (d, J=7.0, 2H), 7.07 (s, 1H), 7.14 (s, 1H), 7.20 (m, 1H), 7.30–7.45 (m, 5H), 7.60–7.72 (m, 6H), 7.89 (d, J=7.5, 2H).

EXAMPLE 85

Preparation of (2R,2S)-N-Isobutyl-N-(4-methylbenzenesulfonylamino)-6-(9-fluorenylmethoxycarboxylamino)-1-hydroxylhexamide (Compound No. 141)

Step A. (2R,2S)-N-Isobutyl-N-(4-methylbenzenesulfonylamino)-6-benzyloxycarbonylamino-1-benzyloxylaminohexane The product of example 35 step D was reacted under the conditions outlined in step A of example 84 substituting ammonium chloride with benzyloxyamine, the crude material (38%) was used without purification in step B.

Step B. Preparation of (2R,2S)-N-Isobutyl-N-(4-methylbenzenesulfonylamino)-6-(9-fluorenylmethoxycarboxylamino)-1-hydroxylaminohexane The title product was obtained in 82% yield by following the indications of step B of example 83, substituting the hexanol derivative by the product obtained in step A of this example.

$^1$H NMR (DMSO-d$_6$): 0.76 (d, J=6.6, 3H), 0.79 (d, J=6.6, 3H), 1.00–1.32 (m, 5H), 1.63–1.69 (m, 1H), 2.00–2.10 (m, 1H), 2.36 (s, 3H), 2.85 (m, 2H), 2.90 and 3.16 (ABX, J=13.5, 7.5, 2H), 4.05 (t, J=7.2, 1H), 4.20 (t, J=7.0, 1H), 4.28 (d, J=7.0, 2H), 7.20 (t, J=5.5, 2H), 7.30–7.45 (m, 6H), 7.70 (m, 4H), 7.90 (d, J=7.4, 2H), 8.86 (s, 1H), 10.63 (br s, 1H).

EXAMPLE 86

Preparation of Nα-Isobutyl-Nα-(4-nitrobenzenesulfonyl)-Nε-(trans-2-methoxycinnamoyl)-L-lysine (Compound No. 161)

A mixture of trans-2-methoxycinnamic acid (106 mg, 0.55 mmol) and carbonyldiimidazole (89 mg, 0.55 mmol) in THF (3 mL) was stirred at room temperature for 1 h, and then at 40° C. until gas evolution ceased. The mixture was cooled to room temperature and Nα-isobutyl-Nα-(4-nitrobenzenesulfonyl)-L-lysine (212 mg, 0.50 mmol) in solution in 1M K$_2$CO$_3$ was added. The reaction mixture was stirred at room temperature for 3 h, then diluted with 1N HCl and extracted with EtOAc. The organic layer was dried over MgSO$_4$, concentrated in vacuo and purified by flash chromatography eluting with 70% EtOAc in hexane containing 0.4% AcOH to give the title compound (71% yield).

$^1$H NMR (DMSO-d$_6$): 0.82 (d, J=6.0, 3H), 0.87 (d, J 6.4, 3H), 1.25–1.63 (m, 5H), 1.85–2.00 (m, 2H), 2.95 (dd, J=13.5, 7.5, 1H), 3.05–3.15 (m, 3H), 3.85 (s, 3H), 4.28 (t, J=7.8, 1H), 6.60 (d, J=16.3, 1H), 6.90–7.50 (m, 4H), 7.63 (d, J=16.3, 1H), 8.02 (t, J=8.7, 2H), 8.37 (d, J=8.6, 2H), 12.70 (br s, 1H). 12.70 (br s, 1H).

EXAMPLE 87

Preparation of Nα-Isobutyl-Nα-(4-nitrobenzenesulfonyl)-Nε-(cis-2-methoxycinnamoyl)-L-lysine (Compound No. 186)

Nα-isobutyl-Nα-(4-nitrobenzenesulfonyl)-L-lysine was reacted with cis-2-methoxycinnamic acid under the conditions described in example 86 to yield 32% of the desired product.

$^1$H NMR (DMSO-d$_6$): 0.82 (d, J=6.0, 3H), 0.87 (d, J=6.4, 3H), 1.20–1.64 (m, 7H), 2.95 (dd, J=13.5, 7.5, 1H), 3.00 (m, 2H), 3.10 (m, 1H), 3.78 (s, 3H), 4.25 (t, J=7.8, 1H), 5.95 (d, J=12.4, 1H), 6.80 (d, J=12.4, 1H), 6.85 (t, J=7.2, 1H), 7.00 (m, 1H), 7.26 (t, J=7.0, 1H), 7.55 (d, J=7.2, 1H), 7.95 (t, J=5.5, 1H), 8.06 (d, J=8.8, 2H), 8.37 (d, J=8.8, 2H), 12.75 (br s, 1H).

EXAMPLE 88

Preparation of Nα-Isobutyl-Nα-(4-nitrobenzenesulfonyl)-Nε-dihydrocinnamoyl-L-lysine (Compound No. 94)

Nα-isobutyl-Nα-(4-nitrobenzenesulfonyl)-L-lysine was reacted with dihydrocinnamic acid under the conditions described in example 86 to yield 81% of the desired product.

$^1$H NMR (DMSO-d$_6$): 0.82 (d, J=7.0, 3H), 0.86 (d, J=7.0, 3H), 1.18–1.60 (m, 5H), 1.80–1.95 (m, 2H), 2.33 (t, J=7.2, 2H), 2.80 (t, J=7.2, 2H), 2.91–3.00 (m, 3H), 3.10 (dd, J=13.2, 7.0, 1H), 4.27 (t, J=7.2, 1H), 7.15–7.30 (m, 5H), 7.74 (t, J=5.2, 1H), 8.06 (d, J=8.0, 2H), 8.38 (d, J=8.0, 2H), 12.70 (br s, 1H).

EXAMPLE 89

Preparation of Nα-Isobutyl-Nα-(4-nitrobenzenesulfonyl)-Nε-(9-xanthenecarbonyl)-L-lysine (Compound No. 96)

Nα-isobutyl-Nα-(4-nitrobenzenesulfonyl)-L-lysine was reacted with xanthene-9-carboxylic acid under the conditions described in example 86 to yield the desired product.

$^1$H NMR (DMSO-d$_6$): 0.75 (d, J=6.5, 3H), 0.78 (d, J=6.8, 3H), 1.2 (br s, 2H), 1.32–1.42 (m, 3H), 1.74–1.86 (m, 2H), 2.82–2.90 (m, 4H), 4.12–4.15 (t, J=14, 1H), 4.85 (s, 1H), 7.04–7.16 (q, J=6.2, 4H), 7.22–7.32 (q, J=6.2, 4H), 8.05 (d, J=14, 2H), 8.45 (d, J=5.14, 2H).

EXAMPLE 90

Preparation of Nα-Isobutyl-Nα-(4-aminobenzenesulfonyl)-Nε-(3-indolepropionyl)-L-lysine (Compound No. 98)

The product of example 69 was reduced by catalytic hydrogenation under the conditions described in example 4 to yield the desired product (95% yield).

LC-MS: 529.3 (M$^+$+H).

EXAMPLE 91

Preparation of Nα-Isobutyl-Nα-(4-nitrobenzenesulfonyl)-Nε-(3-nitrocinnamoyl)-L-lysine (Compound No. 108)

Nα-isobutyl-Nα-(4-nitrobenzenesulfonyl)-L-lysine was reacted with 3-nitrocinnamic acid under the conditions described in example 86 to yield 52% of the desired product.

$^1$H NMR (DMSO-d$_6$): 0.82 (d, J=6.3, 3H), 0.86 (d, J=6.1, 3H), 1.28–1.62 (m, 5H), 1.88–1.96 (m, 2H), 2.95 and 3.10 (ABX, J=14.3, 7.5, 2H), 3.15 (m, 2H), 4.30 (t, J=7.0, 1H), 6.60 (d, J=15.5, 1H), 7.62 (m, 1H), 7.68 (d, J=15.5, 1H), 7.80 (m, 2H), 8.00–8.10 (m, 3H), 8.20 (t, J=5.5, 1H), 8.40 (d, J=8.8, 2H), 12.80 (br s, 1H).

EXAMPLE 92

Preparation of Nα-Isobutyl-Nα-(4-nitrobenzenesulfonyl)-Nε-(2-nitrocinnamoyl)-L-lysine (Compound No. 109)

Nα-isobutyl-Nα-(4-nitrobenzenesulfonyl)-L-lysine was reacted with 2-nitrocinnamic acid under the conditions described in example 86 to yield 42% of the desired product.

¹H NMR (DMSO-d₆): 0.82 (d, J=6.7, 3H), 0.86 (d, J=7.0, 3H), 1.27–1.63 (m, 5H), 1.85–1.95 (m, 2H), 2.92 and 3.10 (ABX, J=14.3, 7.5, 2H), 3.13 (m, 2H), 4.30 (t, J=7.0, 1H), 6.80 (d, J=15.1, 1H), 7.50 (d, J=15.1, 1H), 7.70 (t, J=7.8, 1H), 8.00–8.40 (m, 8H), 12.80 (br s, 1H).

EXAMPLE 93

Preparation of Nα-Isobutyl-Nα-(4-nitrobenzenesulfonyl)-Nε-(2,3-dimethoxycinnamoyl)-L-lysine (Compound No. 110)

Nα-isobutyl-Nα-(4-nitrobenzenesulfonyl)-L-lysine was reacted with 2,3-dimethoxycinnamic acid under the conditions described in example 86 to yield 70% of the desired product.

¹H NR (DMSO-d₆): 0.81 (d, J=6.5, 3H), 0.86 (d, J=6.5, 3H), 1.15–1.60 (m, 5H), 1.82–1.95 (m, 2H), 2.53 (s, 3H), 2.90 (dd,J=14.3, 7.3, 1H), 3.10–3.18 (m, 3H), 3.74 (s, 3H), 4.30 (t, J=7.2, 1H), 6.60 (d, J=15.5, 1H), 7.05–7.15 (m, 3H), 7.60 (d, J=15.5, 1H), 8.10 (m, 3H), 8.36 (d, J=8.0, 1H), 12.80 (br s, 1H).

EXAMPLE 94

Preparation of Nα-Isobutyl-Nα-(4-nitrobenzenesulfonyl)-Nε-(3,5-dimethoxycinnamoyl)-L-lysine (Compound No. 189)

Nα-isobutyl-Nα-(4-nitrobenzenesulfonyl)-L-lysine was reacted with 3,5-dimethoxycinnamic acid under the conditions described in example 86 to yield 66% of the desired product.

¹H NMR (DMSO-d₆): 0.79 (d, J=7.0, 3H), 0.82 (d, J=6.1, 3H), 1.25–1.60 (m, 5H), 1.85–2.00 (m, 2H), 2.90 (dd, J=13.5, 7.5, 1H), 3.05–3.15 (m, 3H), 3.76 (s, 6H), 4.27 (t, J=7.0, 1H), 6.51 (s, 1H), 6.60 (d, J=16.5, 1H), 6.71 (s, 2H), 7.30 (d, J=16.5, 1H), 8.02 (t, J=5.5, 1H), 8.10 (d, J=8.2, 2H), 8.38 (d, J=8.2, 2H), 12.70 (br s, 1H).

EXAMPLE 95

Preparation of Nα-Isobutyl-Nα-(4-nitrobenzenesulfonyl)-Nε-(2,5-dimethoxycinnamoyl)-L-lysine (Compound No. 190)

Nα-isobutyl-Nα-(4-nitrobenzenesulfonyl)-L-lysine was reacted with 2,5-dimethoxycinnamic acid under the conditions described in example 86 to yield 69% of the desired product.

¹H NMR (DMSO-d₆): 0.82 (d, J=6.8, 3H), 0.87 (d, J=6.8, 3H), 1.25–1.62 (m, 5H), 1.82–1.98 (m, 2H), 2.95 (dd, J=13.5, 7.3, 1H), 3.10–3.18 (m, 3H), 3.73 (s, 3H), 3.78 (s, 3H), 4.28 (t, J=7.2, 1H), 6.60 (d, J=16.5, 1H), 6.90–7.05 (m, 3H), 7.60 (d, J=16.5, 1H), 8.00 (t, J=5.5, 1H), 8.10 (d, J=8.3, 2H), 8.40 (d, J=8.2, 2H), 12.70 (br s, 1H).

EXAMPLE 96

Preparation of Nα-Isobutyl-Nα-(4-nitrobenzenesulfonyl)-Nε-(2,4-dimethoxycinnamoyl)-L-lysine (Compound No. 191)

Nα-isobutyl-Nα-(4-nitrobenzenesulfonyl)-L-lysine was reacted with 2,4-dimethoxycinnamic acid under the conditions described in example 86 to yield 72% of the desired product.

¹H NMR (DMSO-d₆): 0.81 (d, J=6.0, 3H), 0.86 (d, J=6.2, 3H), 1.25–1.62 (m, 5H), 1.85–1.98 (m, 2H), 2.95 (dd, J=13.5, 7.5, 1H), 3.05–3.12 (m, 3H), 3.80 (s, 3H), 3.84 (s, 3H), 4.30 (t, J=7.2, 1H), 6.48 (d, J=16.5, 1H), 6.60 (m, 2H), 7.42 (d, J=8.6, 1H), 7.55 (d, J=16.2, 1H), 7.89 (t, J=5.5, 1H), 8.10 (d, J=8.8, 2H), 8.38 (d, J=8.8, 2H), 12.70 (br s, 1H).

EXAMPLE 97

Preparation of Nα-Isobutyl-Nα-(4-nitrobenzenesulfonyl)-Nε-(4-nitrocinnamoyl)-L-lysine (Compound No. 111)

Nα-isobutyl-Nα-(4-nitrobenzenesulfonyl)-L-lysine was reacted with 4-nitrocinnamic acid under the conditions described in example 86 to yield 49% of the desired product.

¹H NMR (DMSO-d₆): 0.81 (d, J=6.0, 3H), 0.86 (d, J=6.0, 3H), 1.25–1.60 (m, 5H), 1.85–1.95 (m, 2H), 2.72 (m, 2H), 2.90 and 3.10 (ABX, J=14.3, 7.5, 2H), 4.15 (m, 2H), 6.80 (d, J=15.5, 1H), 7.50 (d, J=15.5, 1H), 7.82 (d, 8.7, 2H), 8.10 (d, J=8.5, 2H), 8.22 (t, J=5.0, 1H), 8.25 (d, J=8.8, 2H), 8.38 (d, J=8.8, 2H), 12.80 (br s, 1H).

EXAMPLE 98

Preparation of Nα-Isobutyl-Nα-(4-nitrobenzenesulfonyl)-Nε-(trans-4-phenylbuten-2-oyl)-L-lysine (Compound No. 187)

Nα-isobutyl-Nα-(4-nitrobenzenesulfonyl)-L-lysine was reacted with trans-4-phenylbuten-2-oic acid under the conditions described in example 86 to yield 45% of the desired product.

¹H NMR (DMSO-d₆): 0.81 (d, J=6.1, 3H), 0.86 (d, J=6.7, 3H), 1.22–1.62 (m, 5H), 1.84–1.95 (m, 2H), 2.92 and 3.10 (ABX, J=13.5, 7.5, 2H), 3.00 (m, 2H), 4.28 (t, J=7.1, 1H), 6.30 (dt, 16.3, 7.6 1H), 6.45 (d, J=16.0, 1H), 7.20–7.40 (m, 5H), 7.85 (t, J=5.3, 1H), 8.06 (d, J=8.0, 2H), 8.38 (d, J=8.0, 2H), 12.70 (br s, 1H).

EXAMPLE 99

Preparation of Nα-Isobutyl-Nα-(4-nitrobenzenesulfonyl)-Nε-(4-methoxycinnamoyl)-L-lysine (Compound No. 113)

Nα-isobutyl-Nα-(4-nitrobenzenesulfonyl)-L-lysine was reacted with 4-methoxycinnamic acid under the conditions described in example 86 to yield 65% of the desired product.

¹H NMR (DMSO-d₆): 0.81 (d, J=6.0, 3H), 0.86 (d, J=6.9, 3H), 1.25–1.62 (m, 5H), 1.85–1.97 (m, 2H), 2.90 (dd, J=14.5, 7.5, 1H), 3.05–3.14 (m, 3H), 3.78 (s, 3H), 4.30 (t, J=7.0, 1H), 6.42 (d, J=15.3, 1H), 7.00 (d, J=8.0, 2H), 7.34 (d, J=15.3, 1H), 7.50 (d, J=8.0, 2H), 7.95 (t, J=5.5, 1H), 8.02–8.40 (m, 4H), 12.70 (br s, 1H).

EXAMPLE 100

Preparation of Nα-Isobutyl-Nα-(4-nitrobenzenesulfonyl)-Nε-benzylsulfonyl-L-lysine (Compound No. 115)

Nα-isobutyl-Nα-(4-nitrobenzenesulfonyl)-L-lysine was reacted with benzylsulfonyl chloride under the conditions described in example 2 to yield 24% of the desired product.

¹H NMR (DMSO-d₆): 0.82 (d, J=6.5, 3H), 0.88 (d, J=6.5, 3H), 1.22–1.60 (m, 5H), 1.80–1.98 (m, 2H), 2.80 (m, 2H), 2.92 and 3.10 (ABX, J=14.5, 7.3, 2H), 4.25 (m, 1H), 4.28 (s, 2H), 7.00 (t, J=5.5, 1H), 7.30–7.40 (m, 5H), 8.08 (d, J=8.7, 2H), 8.40 (d, J=8.5, 2H), 12.70 (br s, 1H).

EXAMPLE 101

Preparation of Nα-Isobutyl-Nα,Nε-di-(4-nitrobenzenesulfonyl)-L-lysine (Compound No. 116)

Nα-isobutyl-Nα-(4-nitrobenzenesulfonyl)-L-lysine was reacted with 4-nitrobenzenesulfonyl chloride under the conditions described in example 2 to yield 32% of the desired product.

$^1$H NMR (DMSO-d$_6$): 0.80 (d, J=6.2, 3H), 0.84 (d, J=7.1, 3H), 1.18–1.55 (m, 5H), 1.75–1.90 (m, 2H), 2.72 (m, 2H), 2.90 and 3.07 (ABX, J=14.5, 7.5, 2H), 4.20 (dd, J=8.5, 6.0, 1H), 7.90 (t, J=5.5, 1H), 8.02 (d, J=8.0, 2H), 8.06 (d, J=8.0, 2H), 8.35 (d, J=8.2, 2H), 8.42 (d, J=8.0, 2H), 12.80 (br s, 1H)

EXAMPLE 102

Preparation of Nα-Isobutyl-Nα-(4-nitrobenzenesulfonyl)-Nε-(4-methylbenzenesulfonyl)-L-lysine (Compound No. 199)

Nα-isobutyl-Nα-(4-nitrobenzenesulfonyl)-L-lysine was reacted with 4-methylbenzylsulfonyl chloride under the conditions described in example 2 to yield 28% of the desired product.

$^1$H NMR (DMSO-d$_6$): 0.80 (d, J=7.0, 3H), 0.84 (d, J=6.2, 3H), 1.18–1.55 (m, 5H), 1.72–1.95 (m, 2H), 2.38 (s, 3H), 2.62 (m, 2H), 2.90 and 3.10 (ABX, J=14.5, 7.5, 2H), 4.22 (t, J=6.1, 1H), 7.37 (d, J=8.2, 2H), 7.40 (t, J=5.5, 2H), 7.65 (d, J=8.2, 2H), 8.10 (d, J=8.0, 2H), 8.40 (d, J=8.2, 2H), 12.70 (br s, 1H).

EXAMPLE 103

Preparation of Nα-Isobutyl-Nα-(4-nitrobenzenesulfonyl)-Nε-phenylthioacetyl-L-lysine (Compound No. 154)

Nα-isobutyl-Nα-(4-nitrobenzenesulfonyl)-L-lysine was reacted with (phenylthio)acetyl chloride under the conditions described in example 2 to yield 74% of the desired product.

$^1$H NMR (DMSO-d$_6$): 0.81 (d, J=5.8, 3H), 0.85 (d, J=6.9, 3H), 1.16–1.55 (m, 5H), 1.80–1.95 (m, 2H), 2.90 and 3.10 (ABX, J=14.5, 7.5, 2H), 3.00 (m, 2H), 3.60 (s, 3H), 4.23 (t, J=7.0, 1H), 7.18 (t, J=5.5, 1H), 7.27–7.35 (m, 4H), 8.05 (m, 3H), 8.40 (d, J=8.0, 2H), 12.75 (br s, 1H).

EXAMPLE 104

Preparation of Nα-Isobutyl-Nα-(4-nitrobenzenesulfonyl)-Nε-phenoxyacetyl-L-lysine (Compound No. 160)

Nα-isobutyl-Nα-(4-nitrobenzenesulfonyl)-L-lysine was reacted with phenoxyacetyl chloride under the conditions described in example 2 to yield 88% of the desired product.

$^1$H NMR (DMSO-d$_6$): 0.82 (d, J=6.0, 3H), 0.85 (d, J=6.0, 3H), 1.20–1.60 (m, 5H), 1.80–1.96 (m, 2H), 2.92 (dd, J=14.2, 7.5, 1H), 3.05–3.12 (m, 3H), 4.28 (t, J=7.0, 1H), 4.45 (s, 2H), 6.90–7.00 (m, 3H), 7.30 (m, 2H), 8.00 (t, J=4.5, 1H), 8.08 (d, J=8.8, 2H), 8.37 (d, J=8.5, 2H), 12.50 (br s, 1H).

EXAMPLE 105

Preparation of Nα-Isobutyl-Nα-(4-nitrobenzenesulfonyl)-Nε-(3-methoxycinnamoyl)-L-lysine (Compound No. 162)

Nα-isobutyl-Nα-(4-nitrobenzenesulfonyl)-L-lysine was reacted with 3-methoxycinnamic acid under the conditions described in example 86 to yield 50% of the desired product.

$^1$H NMR (DMSO-d$_6$): 0.82 (d, J=7.0, 3H), 0.87 (d, J=7.0, 3H), 1.27–1.62 (m, 5H), 1.85–1.95 (m, 2H), 2.95 and 3.10 (ABX, J=14.3, 7.3, 2H), 3.12 (m, 2H), 3.78 (s, 3H), 4.30 (t, J=6.5, 1H), 6.60 (d, J=16.4, 1H), 6.95 (m, 1H), 7.10 (m, 2H), 7.30–7.40 (m, 2H), 8.03 (t, J=5.0, 1H), 8.08 (d, J=9.0, 2H), 8.38 (d, J=8.8, 2H), 12.70 (br s, 1H).

EXAMPLE 106

Preparation of Nα-Isobutyl-Nα-(4-nitrobenzenesulfonyl)-Nε-(3,4-methylenedioxycinnamoyl)-L-lysine (Compound No. 163)

Nα-isobutyl-Nα-(4-nitrobenzenesulfonyl)-L-lysine was reacted with 3,4-methylenedioxycinnamic acid under the conditions described in example 86 to yield 76% of the desired product.

$^1$H NMR (DMSO-d$_6$): 0.81 (d, J=6.0, 3H), 0.86 (d, J=6.8, 3H), 1.25–1.60 (m, 5H), 1.84–2.00 (m, 2H), 2.93 and 3.10 (ABX, J=14.8, 7.4, 2H), 3.13 (m, 2H), 4.30 (t, J=6.2, 1H), 6.05 (s, 2H), 6.42 (d, J=15.2, 1H), 6.93 (d, J=7.5, 1H), 7.05 (d, J=7.5, 1H), 7.12 (s, 1H), 7.30 (d, J=15.3, 1H), 7.90 (t, J=5.2, 1H), 8.10 (d, J=8.0, 2H), 8.37 (d, J=8.3, 2H), 12.70 (br s, 1H).

EXAMPLE 107

Preparation of Nα-Isobutyl-Nα-(4-nitrobenzenesulfonyl)-Nε-(3,4-dimethoxycinnamoyl)-L-lysine (Compound No. 193)

Nα-isobutyl-Nα-(4-nitrobenzenesulfonyl)-L-lysine was reacted with 3,4-dimethoxycinnamic acid under the conditions described in example 86 to yield 73% of the desired product.

$^1$H NMR (DMSO-d$_6$): 0.82 (d, J=7.0, 3H), 0.87 (d, J=7.0, 3H), 1.20–1.60 (m, 5H), 1.82–1.98 (m, 2H), 2.95 (dd, J=13.5, 7.5, 2H), 3.10–3.17 (m, 2H), 3.78 (s, 3H), 3.79 (s, 3H), 4.30 (m, 1H), 6.56 (d, J=16.5, 1H), 7.00 (d, J=8.0, 1H), 7.10 (d, J=8.2, 1H), 7.13 (s, 1H), 7.32 (d, J=16.5, 1H), 7.93 (t, J=5.5, 1H), 8.10 (d, J=8.3, 2H), 8.38 (d, J=8.0, 2H), 12.70 (br s, 1H).

EXAMPLE 108

Preparation of Nα-Isobutyl-Nα-(4-nitrobenzenesulfonyl)-Nε-(trans-3-(3-pyridyl)acryloyl)-L-lysine (Compound No. 164)

Nα-isobutyl-Nα-(4-nitrobenzenesulfonyl)-L-lysine was reacted with trans-3-(3-pyridyl)acrylic acid under the conditions described in example 86 to yield 60% of the desired product.

$^1$H NMR (DMSO-d$_6$): 0.82 (d, J=7.0, 3H), 0.87 (d, J=6.1, 3H), 1.25–1.62 (m, 5H), 1.88–1.92 (m, 2H), 2.93 and 3.08 (ABX, J=13.5, 7.3, 2H), 3.15 (m, 2H), 4.30 (t, J=6.3, 1H), 6.70 (d, J=15.2, 1H), 7.45 (m, 2H), 7.95 (m, 1H), 8.08 (d, J=8.8, 2H), 8.12 (t, J=5.4, 1H), 8.40 (d, J=8.5, 2H), 12.70 (br s, 1H).

EXAMPLE 109

Preparation of Nα-Isobutyl-Nα-(4-methylbenzenesulfonyl)-Nε-(trans-4-hydroxycinnamoyl)-L-lysine (Compound No. 188)

Nα-isobutyl-Nα-(4-methylbenzenesulfonyl)-L-lysine was reacted with trans-4-hydroxycinnamic acid under the conditions described in example 86 to yield 45% of the desired product.

$^1$H NMR (DMSO-d$_6$): 0.80 (d, J=6.1, 3H), 0.82 (d, J=6.2, 3H), 1.20–1.55 (m, 5H), 1.78–1.95 (m, 2H), 2.37 (s, 3H), 2.90 and 3.00 (ABX, J=14.3, 7.0, 2H), 3.10 (m, 2H), 4.17 (t, J=6.5, 1H), 6.40 (d, J=16.0, 1H), 6.80 (d, J=7.5, 2H), 7.30 (d, J=16.0, 1H), 7.38 (m, 4H), 7.78 (d, J=7.0, 2H), 7.90 (t, J=5.0, 1H), 9.80 (s, 1H), 12.70 (br s, 1H).

EXAMPLE 110

Preparation of Nα-Isobutyl-Nα-(4-aminobenzenesulfonyl)-Nε-(3-aminodihydrocinnamoyl)-L-lysine (Compound No. 118)

The product of example 91 was reduced by catalytic hydrogenation under the conditions described in example 4 to yield the desired product. The yields of the catalytic hydrogenation were usually ranging form 85% to 100%.

$^1$H NMR (DMSO-d$_6$): 0.78 (d, J=7.2, 3H), 0.80 (d, J=7.0, 3H), 1.15–1.46 (m, 5H), 1.72–1.90 (m, 2H), 2.30 (t, J=7.0, 2H), 2.62 (t, J=7.0, 2H), 2.90 (m, 2H), 3.00 (m, 2H), 4.10 (t, J=7.0, 1H), 5.90 (br s, 2H), 6.42–6.60 (m, 4H), 6.88 (m, 2H), 7.40 (d, J=7.2, 2H), 7.80 (t, J=5.0, 1H), 12.70 (br s, 1H).

EXAMPLE 111

Preparation of Nα-Isobutyl-Nα-(4-aminobenzenesulfonyl)-Nε-(2,3-dimethoxydihydrocinnamoyl)-L-lysine (Compound No. 119)

The product of example 93 was reduced by catalytic hydrogenation under the conditions described in example 4 to yield the desired product.

$^1$H NMR (DMSO-d$_6$): 0.78 (d, J=6.5, 3H), 0.80 (d, J=6.5, 3H), 1.15–1.42 (m, 5H), 1.72–1.90 (m, 2H), 2.30 (t, J=7.2, 2H), 2.76 (t, J=7.2, 2H), 2.82–3.00 (m, 4H), 3.71 (s, 3H), 3.77 (s, 3H), 4.10 (t, J=7.2, 1H), 5.95 (s, 2H), 6.60 (d, J=7.6, 2H), 6.73 (d, J=7.5, 1H), 6.86 (d, J=7.4, 1H), 6.95 (t, J=8.5, 1H), 7.40 (d, J=7.7, 2H), 7.75 (br s, 1H), 12.55 (br s, 1H).

EXAMPLE 112

Preparation of Nα-Isobutyl-Nα-(4-aminobenzenesulfonyl)-Nε-(4-methoxydihydrocinnamoyl)-L-lysine (Compound No. 120)

The product of example 99 was reduced by catalytic hydrogenation under the conditions described in example 4 to yield the desired product.

$^1$H NMR (DMSO-d$_6$): 0.78 (d, J=7.0, 3H), 0.80 (d, J=6.5, 3H), 1.15–1.48 (m, 5H), 1.70–1.90 (m, 2H), 2.30 (t, J=7.0, 2H), 2.75 (t, J=7.0, 2H), 2.70–3.00 (m, 4H), 3.73 (s, 3H), 4.10 (t, J=7.0, 1H), 5.95 (s, 2H), 6.46 (d, J=7.5, 2H), 6.57 (d, J=7.5, 2H) 6.82 (d, J=7.8, 2H), 7.40 (d, J=7.5, 2H), 7.69 (t, J=5.2, 1H), 12.60 (br s, 1H).

EXAMPLE 113

Preparation of Nα-Isobutyl-Nα-(4-aminobenzenesulfonyl)-Nε-(2-aminodihydrocinnamoyl)-L-lysine (Compound No. 122)

The product of example 92 was reduced by catalytic hydrogenation under the conditions described in example 4 to yield the desired product.

$^1$H NMR (DMSO-d$_6$): 0.78 (d, J=6.0, 3H), 0.80 (d, J=6.0, 3H), 1.18–1.50 (m, 5H), 1.72–1.90(m, 2H), 2.27 (t, J=7.0, 2H), 2.60 (t, J=7.0, 2H), 2.85–3.00 (m, 4H), 4.00 (t, J=7.0, 1H), 5.94 (s, 2H), 6.31–6.37 (m, 3H), 6.58 (d, J=8.2, 2H), 6.89 (t, J=8.2, 1H), 7.39 (d, J=8.2, 2H), 7.73 (t, J=4.9, 1H).

EXAMPLE 114

Preparation of Nα-Isobutyl-Nα-(4-aminobenzenesulfonyl)-Nε-( 3,4-methylenedioxydihydrocinnamoyl)-L-lysine (Compound No. 155)

The product of example 106 was reduced by catalytic hydrogenation under the conditions described in example 4 to yield the desired product.

$^1$H NMR (DMSO-d$_6$): 0.78 (d, J=7.0, 3H), 0.80 (d, J=6.2, 3H), 1.18–1.50 (m, 5H), 1.70–1.90 (m, 2H), 2.30 (t, J=7.2, 2H), 2.70 (t, J=7.2, 2H), 2.80–3.00 (m, 4H), 4.12 (t, J=7.0, 1H), 5.93 (s, 2H), 5.95 (s, 2H), 6.80 (m, 2H), 7.38 (d, J=8.4, 2H), 7.78 (t, J=4.5, 1H), 12.55 (br s, 1H).

EXAMPLE 115

Preparation of Nα-Isobutyl-Nα-(4-aminobenzenesulfonyl)-Nε-(3,4-dimethoxydihydrocinnamoyl)-L-lysine (Compound No. 200)

The product of example 107 was reduced by catalytic hydrogenation under the conditions described in example 4 to yield the desired product.

$^1$NMR (DMSO-d$_6$): 0.78 (d, J=6.5, 3H), 0.80 (d, J=6.5, 3H), 1.17–1.50 (m, 5H), 1.72–1.90 (m, 2H), 2.30 (t, J=7.2, 2H), 2.72 (t, J=7.2, 2H), 2.80–3.00 (m, 4H), 3.69 (s, 3H), 3.72 (s, 3H), 4.10 (t, J=6.7, 1H), 5.94 (br s, 2H), 6.55–6.82 (m, 5H), 7.40 (d, J=8.2, 2H), 7.74 (t, J=4.5, 1H), 12.45 (br s, 1H).

EXAMPLE 116

Preparation of Nα-Isobutyl-Nα-(4-aminobenzenesulfonyl)-Nε-(3-methoxydihydrocinnamoyl)-L-lysine (Compound No. 156)

The product of example 105 was reduced by catalytic hydrogenation under the conditions described in example 4 to yield the desired product.

$^1$H NMR (DMSO-d$_6$): 0.78 (d, J=7.0, 3H), 0.80 (d, J=7.0, 3H), 1.12–1.48 (m, 5H), 1.71–1.82 (m, 2H), 2.33 (t, J=7.2, 2H), 2.78 (t, J=7.2, 2H), 2.80–3.00 (m, 4H), 3.70 (s, 3H), 4.10 (t, J=7.0, 1H), 5.95 (s, 2H), 6.60 (d, J=8.0, 2H), 6.75 (m, 3H), 7.17 (m, 1H), 7.40 (d, J=8.0, 2H), 7.75 (t, J=5.5, 1H), 12.60 (br s, 1H).

EXAMPLE 117

Preparation of Nα-Isobutyl-Nα-(4-aminobenzenesulfonyl)-Nε-(2-methoxydihydrocinnamoyl)-L-lysine (Compound No. 157)

The product of example 86 was reduced by catalytic hydrogenation under the conditions described in example 4 to yield the desired product.

$^1$H NMR (DMSO-d$_6$): 0.78 (d, J=6.1, 3H), 0.80 (d, J=6.5, 3H), 1.15–1.48 (m, 5H), 1.71–1.92 (m, 2H), 2.30 (t, J=7.6, 2H), 2.75 (t, J=7.6, 2H), 2.80–3.00 (m, 4H), 3.80 (s, 3H), 4.10 (t, J=6.0, 1H), 5.95 (s, 2H), 6.57 (d, J=7.8, 2H), 6.82 (t, J=7.2, 1H), 6.92 (d, J=8.0, 1H), 7.11 (d, J=8.1, 1H), 8.17 (t, J=7.2, 1H), 7.70 (t, J=5.0, 1H), 12.50 (br s, 1H).

EXAMPLE 118

Preparation of Nα-Isobutyl-Nα-(4-aminobenzenesulfonyl)-Nε-(4-phenylbutanoyl)-L-lysine (Compound No. 121)

The product of example 98 was reduced by catalytic hydrogenation under the conditions described in example 4 to yield the desired product.

$^1$H NMR (DMSO-d$_6$): 0.76 (d, J=7.0, 3H), 0.79 (d, J=7.0, 3H), 1.18–1.50 (m, 5H), 1.72–1.80 (m, 4H), 2.06 (t, J=7.0, 2H), 2.54 (t, J=7.2, 2H), 2.82–2.92 (m, 2H), 2.97 (m, 2H), 4.10 (t, J=7.0, 1H), 5.95 (s, 2H), 6.60 (d, J=8.2, 2H), 7.18 (d, J=8.0, 3H), 7.26 (m, 2H), 7.47 (d, J=7.5, 2H), 7.70 (d, J=4.2, 1H), 12.70 (br s, 1H).

EXAMPLE 119

Preparation of Nα-Isobutyl-Nα-(4-aminobenzenesulfonyl)-Nε-(4-aminodihydrocinnamoyl)-L-lysine (Compound No. 194)

The product of example 97 was reduced by catalytic hydrogenation under the conditions described in example 4 to yield the desired product.

$^1$H NMR (DMSO-d$_6$): 0.78 (d, J=7.0, 3H), 0.80 (d, J=6.5, 3H), 1.15–1.48 (m, 5H), 1.70–1.90 (m, 2H), 2.21 (t, J=7.6, 2H), 2.62 (t, J=7.6, 2H), 2.70–3.00 (m, 4H), 4.12 (t, J=7.0, 1H), 5.94 (s, 2H), 6.46 (d, J=7.5, 2H), 6.57 (d, J=7.5, 2H), 6.82 (d, J=7.5, 2H), 7.40 (d, J=7.2, 2H), 7.69 (t, J=5.2, 1H), 12.60 (br s, 1H).

EXAMPLE 120

Preparation of Nα-Isobutyl-Nα-(4-aminobenzenesulfonyl)-Nε-[3-(3-pyridyl)propionyl]-L-lysine (Compound No. 195)

The product of example 108 was reduced by catalytic hydrogenation under the conditions described in example 4 to yield the desired product.

$^1$H NMR (DMSO-d$_6$): 0.77 (d, J=6.2, 3H), 0.80 (d, J=6.5, 3H), 1.10–1.48 (m, 5H), 1.70–1.90 (m, 2H), 2.38 (t, J=7.5, 2H), 2.80 (t, J=7.5, 2H), 2.84–3.00 (m, 4H), 4.10 (t, J=7.0, 1H), 5.95 (s, 2H), 6.58 (d, J=7.0, 2H), 7.28 (m, 1H), 7.40 (d, J=7.1, 2H), 7.60 (d, J=8.0, 1H), 7.78 (d, J=5.5, 2H), 8.38 (d, J=4.3, 1H), 8.41 (s, 1H), 12.70 (br s, 1H).

EXAMPLE 121

Preparation of Nα-Isobutyl-Nα-(4-aminobenzenesulfonyl)-Nε-(2,4-dimethoxydihydrocinnamoyl)-L-lysine (Compound No. 196)

The product of example 96 was reduced by catalytic hydrogenation under the conditions described in example 4 to yield the desired product.

$^1$H NMR (DMSO-d$_6$): 0.78 (d, J=7.0, 3H), 0.80 (d, J=6.5, 3H), 1.17–1.50 (m, 5H), 1.70–1.95 (m, 2H), 2.22 (t, J=7.0, 2H), 2.68 (t, J=7.0, 2H), 2.82–3.00 (m, 4H), 3.71 (s, 3H), 3.75 (s, 3H), 4.10 (t, J=7.0, 1H), 5.95 (s, 2H), 6.40 (m, 1H), 6.50 (s, 1H), 6.58 (d, J=8.7, 2H), 6.99 (d, J=8.6, 1H), 7.40 (d, J=8.7, 2H), 7.70 (t, J=5.0, 1H), 12.70 (br s, 1H).

EXAMPLE 122

Preparation of Nα-Isobutyl-Nα-(4-aminobenzenesulfonyl)-Nε-(2,5-dimethoxydihydrocinnamoyl)-L-lysine (Compound No. 197)

The product of example 95 was reduced by catalytic hydrogenation under the conditions described in example 4 to yield the desired product.

$^1$H NMR (DMSO-d$_6$): 0.78 (d, J=7.0, 3H), 0.80 (d, J=7.0, 3H), 1.15–1.50 (m, 5H), 1.72–1.90 (m, 2H), 2.26 (t, J=7.6, 2H), 2.70 (t, J=7.6, 2H), 2.82–3.00 (m, 4H), 3.66 (s, 3H), 3.72 (s, 3H), 4.10 (t, J=7.0, 1H), 5.95 (s, 2H), 6.58 (d, J=7.9, 2H), 6.70 (s, 2H), 6.84 (m, 1H), 7.70 (t, J=5.0, 2H), 12.70 (br s, 1H).

EXAMPLE 123

Preparation of Nα-Isobutyl-Nα-(4-aminobenzenesulfonyl)-Nε-3,5-dimethoxydihydrocinnamoyl-L-lysine (Compound No. 198)

The product of example 94 was reduced by catalytic hydrogenation under the conditions described in example 4 to yield the desired product.

$^1$H NMR (DMSO-d$_6$): 0.78 (d, J=6.7, 3H), 0.80 (d, J=7.0, 3H), 1.15–1.50 (m, 5H), 1.70–1.90 (m, 2H), 2.30 (t, J=7.2, 2H), 2.75 (t, J=7.2, 2H), 2.82–2.99 (m, 4H), 3.70 (s, 6H), 5.95 (s, 2H), 6.30 (s, 1H), 6.35 (s, 2H), 6.57 (d, J=8.0, 2H), 7.40 (d, J=8.0, 2H), 7.75 (t, J=5.5, 1H), 12.50 (br s, 1H).

EXAMPLE 124

Preparation of Nα-Isobutyl-Nα-(4-aminobenzenesulfonyl)-Nε-dihydrocinnamoyl-L-lysine (Compound No. 158)

The product of example 88 was reduced by catalytic hydrogenation under the conditions described in example 4 to yield the desired product.

$^1$H NMR (DMSO-d$_6$): 0.78 (d, J=6.2, 3H), 0.81 (d, J=6.2, 3H), 1.12–1.46 (m, 5H), 1.70–1.80 (m, 1H), 1.81–1.92 (m, 1H), 2.32 (t, J=7.0, 2H), 2.78 (t, J=7.0, 2H), 2.80–3.00 (m, 4H), 4.12 (t, J=7.0, 1H), 5.95 (br s, 2H), 6.60 (d, J=8.7, 2H), 7.13–7.25 (m, 5H), 7.40 (d, J=8.5, 2H), 7.70 (t, J=4.0, 1H), 12.70 (br s, 1H).

EXAMPLE 125

Preparation of Nα-Isobutyl-Nα-(4-methylbenzenesulfonyl)-Nε-(4-hydroxydihydrocinnamoyl)-L-lysine (Compound No. 126)

The product of example 109 was reduced by catalytic hydrogenation under the conditions described in example 4 to yield the desired product.

$^1$H NMR (DMSO-d$_6$): 0.80 (d, J=6.1, 3H), 0.82 (d, J=6.0, 3H), 1.15–1.50 (m, 5H), 1.70–1.92 (m, 2H), 2.26 (t, J=7.5, 2H), 2.37 (s, 3H), 2.67 (t, J=7.5, 2H), 2.88–3.02 (m, 4H), 4.17 (t, J=7.0, 1H), 6.63 (d, J=8.5, 2H), 6.95 (d, J=7.5, 2H), 7.36 (d, J=8.2, 2H), 7.66 (d, J=7.5, 2H), 7.70 (t, J=5.0, 1H), 9.10 (s, 1H), 12.70 (br s, 1H).

EXAMPLE 126

Preparation of Nα-Isobutyl-Nα-(4-methylbenzenesulfonyl)-Nε-dihydrothiocinnamoyl-DL-lysine (Compound No. 153)

Step A. Preparation of Nα-Isobutyl-Nα-(4-methylbenzenesulfonyl)-Nε-dihydrocinnamoyl-L-lysine Methyl Ester Nα-isobutyl-Nα-(4-methylbenzenesulfonyl)-Nε-dihydrocinnamoyl-L-lysine was esterified with diazomethane following indications found in example 82 to provide a quantitative yield of the title methyl ester.

$^1$H NMR (DMSO-d$_6$): 0.83 (d, J=6.8, 3H), 0.87 (d, J=7.0, 3H), 1.32–1.75 (m, 5H), 1.88–2.00 (m, 2H), 2.42 (s, 3H), 2.50 (t, J=7.2, 2H), 2.90 and 3.05 (dd, J=14.5, 7.4, 2H), 3.00 (t, J=7.0, 2H), 3.50 (s, 3H), 4.40 (t, J=7.0, 1H), 5.60 (br s, 1H), 7.18–7.32 (m, 7H), 7.69 (d, J=7.8, 2H).

Step B. Preparation of Nα-Isobutyl-Nα-(4-methylbenzenesulfonyl)-Nε-dihydrothiocinnamoyl-L-lysine Methyl Ester To a stirred solution of the product from step A of this example (1.0 g, 2.0 mmol) in THF (20 mL) was added Lawesson's reagent (808 mg, 2.00 mmol). The reaction mixture was stirred ar room temperature for 3 h, concentrated in vacuo and purified by flash chromatography eluting with 60% EtOAc in hexane, providing 980 mg (95%) of the desired thioamide.

$^1$H NMR (DMSO-d$_6$): 0.82 (d, J=7.2, 3H), 0.86 (d, J=6.2, 3H), 1.35–1.45 (m, 2H), 1.55–1.98 (m, 5H), 2.45 (s, 3H), 2.88 and 3.05 (dd, J=14.8, 7.5, 2H), 2.95 (t, J=7.7, 2H), 3.12 (t, J=7.5, 2H), 3.50 (s, 3H), 3.60 (m, 2H), 4.42 (t, J=7.2, 1H), 7.20–7.32 (m, 7H), 7.50 (br s, 1H), 7.72 (d, J=7.6, 2H).

Step C. Preparation of Nα-Isobutyl-Nα-(4-methylbenzenesulfonyl)-Nε-dihydrothiocinnamoyl-DL-lysine The product from step B of this example was saponified according to the indications of example 35 step D to afford the title compound quantitatively.

$^1$H NMR (DMSO-d$_6$): 0.79 (d, J=6.7, 3H), 0.82 (d, J=6.5, 3H), 1.40–1.50 (m, 4H), 1.78–1.92 (m, 3H), 2.37 (s, 3H), 2.80 (t, J=7.2, 2H), 2.90 (dd, J=14.3, 7.5, 2H), 2.94–3.05 (m, 3H), 4.20 (t, J=7.0, 1H), 7.17–7.30 (m, 5H), 7.37 (d, J=7.7, 2H), 7.67 (d, J=7.5, 2H), 9.90 (br s, 1H), 12.70 (br s, 1H).

EXAMPLE 127

Preparation of Nα,Nδ-di-(4-Bromobenzenesulfonyl)-Nδ-(4-fluorobenzyl)-L-ornithine (Compound No. 59)

To a stirred solution of Nα,Nδ-di-(4-bromobenzenesulfonyl)-L-ornithine (145 mg, 0.25 mmol) in DMF (2.5 mL) was added NaH. The reaction was stirred at room temperature until the hydrogen evolution stoped. 4-fluorobenzyl bromide (57 mg, 0.3 mmol) in solution in DMF (0.5 mL) was added and the mixture was allowed to stirr at room temperature for 1 h. HCl (1N) was added until acidic pH (~3) and the reaction was extracted with EtOAc. The organic layer was dried (MgSO$_4$) and concentrated. The crude material was purified by flash chromatography eluting with hexanes:EtOAc:AcOH, 50:50:00; 25:75:00 and then 25:70:0.5 to afford 142 mg (84%) of the title compound.

$^1$H NMR (DMSO-d$_6$): 1.20–1.50 (m, 4H), 2.98–3.10 (m, 2H), 3.55 (m, 1H), 4.20 (s, 2H), 7.10 –7.33 (m, 4H), 7.60–7.80 (m, 8H), 8.18 (d, J=9.0, 1H), 12.60 (br s, 1H).

EXAMPLE 128

Preparation of Nα,Nε-di-(4-bromobenzenesulfonyl)-Nε-(4-fluorobenzyl)-L-lysine (Compound No. 60)

Nα,Nε-di-(4-bromobenzenesulfonyl)-L-lysine was reacted with 4-fluorobenzyl bromide under the conditions described in example 127 to yield 85% of the desired product.

$^1$H NMR (DMSO-d$_6$): 1.05–1.45 (m, 6H), 2.92–3.05 (m, 2H), 3.55 (m, 1H), 4.26 (s, 2H), 7.12–7.37 (m, 4H), 7.60–7.85 (m, 8H), 8.17 (d, J=8.1, 1H), 12.30 (br s, 1H).

EXAMPLE 129

Preparation of Nα, Nε-diisobutyl-Nα-(4-methylbenzenesulfonyl)-Nε-(3-phenylpropanoyl)-DL-lysine (Compound No. 159)

Step A. Preparation of Nα,Nε-diisobutyl-Nα-(4-methylbenzenesulfonyl)-Nε-(phenylpropanoyl)-L-lysine Methyl Ester The product of example 35 (step C) (Nα-isobutyl-Nα-(4-methylbenzenesulfonyl)-Nε-benzyloxycarbonyl-L-lysine methyl ester) was reduced by catalytic hydrogenation under the conditions described in example 4 to yield the free amine which was subjected to reductive alkylation under the conditions described in example 35 (step B) followed by acylation with 3-phenylpropionyl chloride under the conditions described in example 35 (step C) to give the title compound (75% yield).

$^1$H NMR (CDCl$_3$): 0.83–0.89 (m, 12H, 4 CH$_3$), 1.15–1.65 (m, 5H), 1.82–2.00 (m, 3H), 2.42 (s, 3H), 2.60 (m, 2H), 2.70 (m, 2H), 2.93–3.05 (m, 5H), 3.17 (m, 1H), 3.22–3.40 (m, 1H), 5.5 (s, 3H), 4.40 (m, 1H), 7.22–7.33 (m, 3H).

Step B. Preparation of Nα,Nε-Diisobutyl-Nα-(4-methylbenzenesulfonyl)-Nε-(3-phenylpropanoyl)-DL-lysine The product from step A of this example was saponified according to the indications of example 35 step D to afford the title compound quantitatively.

$^1$H NMR (DMSO-d$_6$): 0.76–0.83 (m, 12H, 4 CH$_3$), 1.09–1.50 (m, 5H), 1.78–1.92 (m, 3H), 2.38 (s, 3H), 2.52 (m, 2H), 2.80 (m, 2H), 2.85–3.15 (m, 6H), 4.20 (t, J=7.0, 1H), 7.38 (m, 2H), 7.67 (t, J=8.8, 2H), 12.65 (br s, 1H).

EXAMPLE 130

Preparation of Nα-Isobutyl-Nα-(4-aminobenzenesulfonyl)-Nε-phenoxyacetyl-L-lysine (Compound No. 192)

The product of example 104 was reduced by catalytic hydrogenation under the conditions described in example 4 to yield 100% of the title compound.

$^1$H NMR (DMSO-d$_6$): 0.78 (d, J=6.0, 3H), 0.80 (d, J=6.0, 3H), 1.17–1.50 (m, 5H), 1.72–1.90 (m, 2H), 2.82 and 2.90 (ABX, J=14.0, 7.5, 2H), 3.08 (m, 2H), 4.10 (t, J=7.2, 1H), 4.43 (s, 2H), 5.95 (br s, 2H), 6.60 (d, J=7.6, 2H), 6.90–7.00 (m, 3H), 7.30 (m, 2H), 7.39 (d, J=7.5, 2H), 8.02 (t, J=5.0, 1H), 12.70 (br s, 1H).

EXAMPLE 131

Preparation of Nα-Isobutyl-Nα-(4-methylbenzenesulfonyl)-Nε-(2,3-dimethoxydihydrocinnamoyl)-L-lysine (Compound No. 201)

Step A. Preparation of Nα-isobutyl-Nα-(4-methylbenzenesulfonyl)-Nε-(2,3-dimethoxycinnamoyl)-L-lysine Nα-isobutyl-Nα-(4-methylbenzenesulfonyl)-L-lysine was reacted with 2,3-dimethoxycinnamic acid under the conditions described in example 86. The crude material was purified by flash chromatography (CH$_2$Cl$_2$:MeOH, 49:1 to 9:1) to yield 18% of the desired product.

$^1$H NMR (DMSO-d$_6$): 0.81 (m, 6H), 1.24 (m, 2H), 1.40 (m, 3H), 1.87 (m, 2H), 2.37 (s, 3H), 2.95 (m, 2H), 3.09 (s,

2H), 3.74 (s, 3H), 3.82 (s, 3H), 4.19 (s, 1H), 6.60 (d, J=16.0, 1H), 7.10 (m, 3H), 7.36 (d, J=7.0, 2H), 7.58 (d, J=15.0, 1H), 7.68 (d, J=7.0, 2H), 8.07 (s, 1H), 12.65 (br s, 1H).

Step B. Preparation of Nα-Isobutyl-Nα-(4-methylbenzenesulfonyl)-Nε-(2,3-dimethoxydihydrocinnamoyl)-L-lysine The product of step A was reduced by catalytic hydrogenation under the conditions described in example 4 to yield 95% of the title compound.

$^1$H NMR (CDCl$_3$): 0.87 (s, 6H), 1.16 (m, 2H), 1.37 (m, 2H), 1.56 (m, 1H), 1.90 (m, 2H), 2.34 (t, J=8.0, 2H), 2.40 (s, 3H), 2.82 (t, J=8.0, 2H), 2.99 (m, 2H), 3.75 (s, 3H), 3.81 (s, 3H), 4.23 (t, J=7.0, 1H), 6.79 (d, J=7.0, 1H), 6.90 (d, J=8.0, 1H), 6.99 (t, J=8.0, 1H), 7.40 (d, J=8.0, 2H), 7.72 (d, J=8.0, 2H), 7.78 (s, 1H).

EXAMPLE 132

Preparation of Nα-Isobutyl-Nα-(4-methylbenzenesulfonyl)-Nε-phenylthioacetyl-L-lysine (Compound No. 202)

Nα-isobutyl-Nα-(4-methylbenzenesulfonyl)-L-lysine was reacted with (phenylthio)acetyl choride under conditions described in example 2. The crude material was purified by flash chromatography (CH$_2$Cl$_2$:MeOH, 19:1 to 9:1) to yield 38% of the desired product.

$^1$H NMR (CDCl$_3$): 0.85 (s, 6H), 1.01 (s, 2H), 1.32 (m, 2H), 1.47 (m, 1H), 1.86 (m, 2H), 2.41 (s, 3H), 3.02 (d, J=10.0, 2H), 3.07 (m, 1H), 3.13 (m, 1H), 3.62 (s, 2H), 4.13 (m, 1H), 6.80 (s, 1H), 7.20–7.30 (m, 7H), 7.69 (d, J=10.0, 2H).

EXAMPLE 133

Preparation of Nα-Isobutyl-Nα-(4-methylbenzenesulfonyl)-Nε-phenoxyacetyl-L-lysine (Compound No. 203)

Nα-isobutyl-Nα-(4-methylbenzenesulfonyl)-L-lysine was reacted with phenoxyacetyl chloride under the conditions described in example 2. The crude material was purified by flash chromatography (CH$_2$Cl$_2$:MeOH, 19:1 to 9:1) to yield 77% of the desired product.

$^1$H NMR (CDCl$_3$): 0.87 (s, 6H), 1.33 (s, 2H), 1.54 (m, 2H), 1.64 (m, 1H), 1.95 (m, 2H), 2.40 (s, 3H), 2.98 (m, 1H), 3.04 (m, 1H), 3.30 (s, 2H), 4.34 (m, 1H), 4.50 (s, 2H), 6.78 (s, 1H), 6.94 (d, J=7.0, 2H), 7.04 (t, J=7.0, 1H), 7.29 (m, 2H), 7.33 (m, 2H), 7.72 (d, J=7.0, 1H), 8.47 (br s, 1H).

EXAMPLE 134

Preparation of Nα-Isobutyl-Nα-(4-methylbenzenesulfonyl)-Nε-(dihydrothiocinnamoyl-N-cyanoamidine)-DL-lysine (Compound No. 204)

To a stirred solution of Nα-isobutyl-Nα-(4-methylbenzenesulfornyl)-Nε-dihydrothiocinnamoyl-L-lysine methyl ester (example 126 step B) (170 mg, 0.33 mmol) in MeOH (3 mL) was added cyanamide (28 mg, 0.66 mmol). The mixture was stirred for 5 min, then mercuric acetate (209 mg, 0.66 mmol) was added. The reaction mixture was stirred for 3 h, then diluted with a saturated solution of NH$_4$Cl and extracted with EtOAc. The organic layer was concentrated then diluted with THF/MeOH (1 mL/1 mL) and treated with 1N NaOH (1.2 mL). After stirring for 4 h, the reaction was acidified with 1N HCl (pH~1–2) and extracted with EtOAc. The organic layer was dried, concentrated and purified by flash chromatography (hexane: EtOAc: AcOH, 30:70:0.4) to give 110 mg (65%) of the title compound.

$^1$H NMR (DMSO-d$_6$): 0.79 (d, J=6.0, 3H), 0.83 (d, J=6.0, 3H), 1.10–1.20 (m, 2H), 1.22–1.35 (m, 2H), 1.40–1.50 (m, 1H), 1.78 (m, 1H), 1.90 (m, 1H), 2.33 (t, J=7.6, 2H), 2.80 (t, J=7.5, 2H), 2.88–3.00 (m, 4H), 4.20 (t, J=7.2, 1H), 7.15–7.30 (m, 5H), 7.37 (d, J=7.6, 2H), 7.66 (d, J=7.5, 2H), 7.73 (t, J=5.3, 1H), 12.70 (br s, 1H).

EXAMPLE 135

Preparation of (2R,2S)-2-[N-Isobutyl-N-(4-methylbenzenesulfonyl)]-3-[2'-(N'-dihydrocinnamoyl)ethylamino]-propionic Acid (Compound No. 206)

Step A. Preparation of Nα-Isobutyl-L-serine Methyl Ester

L-serine methyl ester was subjected to reductive alkylation under the conditions described in example 35 step B to give 66% of the desired product.

$^1$H NMR (CDCl$_3$): 0.89 (d, J=6.3, 3H), 0.91 (d, J=6.3, 3H), 1.70 (h, J=7.0, 3H), 2.28 and 2.50 (ABX, J=11.1, 7.3, 2H), 3.33 (m, 1H), 3.20–3.40 (br s, 1H), 3.58 (mn, 1H), 3.73 (m, 3H), 3.76 (m, 1H).

Step B. Preparation of Nα-Isobutyl-Nα-4-methylbenzenesulfonyl-L-serine Methyl Ester To a stirred solution of Nα-isobutyl-L-serine methyl ester (1.2 g, 6.93 mmol) in dioxane/water (20 mL/10 mL) was added NaHCO$_3$ (614 mg, 7.63 mmol). The mixture was stirred at 40° C. overnight, then acidified with 1N HCl (pH~1) and extracted with EtOAc. The organic layer was dried (MgSO$_4$) and concentrated. The crude was purified by flash chromatography (hexane: EtOAc, 70:30) to yield 1.3 g (81%) oft he tosylate.

$^1$H NMR (CDCl$_3$): 0.82 (d, J=6.3, 3H), 0.85 (d, J=6.2, 3H), 1.85–1.92 (m, 1H), 2.41 (s, 3H), 2.52 (br s, 1H), 2.90 and 3.10 (ABX, J=15.2, 7.4, 2H), 3.58 (s, 3H), 3.80 (m, 1H), 4.11 (t, J=8.0, 1H), 4.39 (t, J=7.2, 1H), 7.28 (d, J=8.2, 2H), 7.70 (d, J=8.0, 2H).

Step C. Preparation of 2-[N-Isobutyl-N-(4-methylbenzenesulfonyl)]methyl Acrylate To a stirred solution of the tosylate (330 mg, 1 mmol) in CH$_2$Cl$_2$ (10 mL) was added triethylamine (153 µL, 1.1 mmol) and tosyl chloride (209 mg, 1, 1, mmol). The reaction was stirred for 4 h, then triethylamine (306 µL, 2.2 mmol) was added. The reaction mixture was allowed to stir overnight. It was diluted with 1N HCl and EtOAc, the organic layer was collected and concentrated. The crude was purified by flash chromatography (hexane:EtOAc, 4:1) to yield 220 mg (71%) of the acrylate.

$^1$H NMR (CDCl$_3$): 0.89 (d, J=6.7, 6H), 1.70 (h, J=7.0, 1H), 2.41 (s, 3H), 3.15 (d, J=7.5, 2H), 3.65 (s, 3H), 5.71 (s, 1H), 6.36 (s, 1H), 7.28 (d, J=8.0, 2H), 6.67 (d, J=8.0, 2H).

Step D. Preparation of (2R,2S)-2-[N-Isobutyl-N-(4-methylbenzenesulfonyl)]-3-[2'-(N'-dihydrocinnamoyl)ethylamino]-propionic Acid Methyl Ester Triethylamine (55 µL, 0.4 mmol) was added to a stirred solution of the acrylate (104 mg, 0.33 mmol) and N-dihydrocinnamoyl ethylenediamine trifluoroacetic acid salt (111 mg, 0.36 mmol) in MeOH. The mixture was stirred for 2 days then concentrated and purified by flash chromatography (CH$_2$Cl$_2$:MeOH, 95:05) to yield the amine ester (80 mg, 50%).

$^1$H NMR (DMSO-d$_6$): 0.79 (d, J=7.2, 3H), 0.80 (d, J=7.0, 3H), 1.65 (br s, 1H), 1.88 (h, J=7.2, 1H), 2.30–2.36 (m, 2H), 2.38 (s, 3H), 2.42 (t, J=6.1, 2H), 2.65 (dd, J=12.5, 7.0, 1H), 2.80 (m, 3H), 2.90–3.10 (m, 5H), 3.46 (s, 3H), 4.35 (t, J=7.2, 1H), 7.14–7.30 (m, 5H), 7.39 (d, J=8.4, 2H), 7.70 (d, J=8.2, 2H), 7.73 (t, J=5.0, 1H).

Step E. Preparation of (2R,2S)-2-[N-Isobutyl-N-(4-methylbenzenesulfonyl)]-3-[2'-(N'-dihydrocinnamoyl) ethylamino]-propionic Acid NaOH (100 μL, 1N) was added to a stirred solution of aminoester (45 mg, 0.089 mmol) in THF/MeOH (1 mL/1 mL). The reaction was stirred for 3 h then acidified with TFA and concentrated. The crude was purified by flash chromatography (CH$_2$Cl$_2$:MeOH, 4:1) to yield the desired product (35 mg, 80%).

$^1$H NMR (DMSO-d$_6$): 0.75 (d, J=6.4, 3H), 0.78 (d, J=7.1, 3H), 1.80 (h, J=7.0, 1H), 2.36 (s, 3H), 2.39 (m, 2H), 2.80–2.88 (m, 4H), 2.90 and 3.00 (ABX, J=14.5, 7.4, 2H), 3.12 (t, J=8.0, 1H), 3.20–3.28 (m, 1H), 4.20 (dd, J=11.0, 5.0, 1H), 7.16–7.28 (m, 5H), 7.33 (d, J=8.0, 2H), 7.73 (d, J=8.0, 2H), 7.99 (t, J=5.0, 1H), 9.25–9.75 (br s, 1H).

We claim:

1. A compound of formula Ia

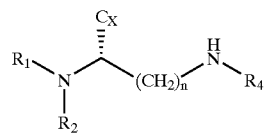

(Ia)

wherein n is 1, 2, 3, 4 or 5 wherein Cx is selected from the group consisting of —COOH, —COOR$_5$, —CH$_2$OH, and —CONHOH, wherein R$_1$ is selected from the group consisting of a straight or branched alkyl group of 1 to 6 carbon atoms, cyclopropylmethyl and benzyl, wherein R$_2$ is selected from the group consisting of 4-C$_6$H$_5$CH$_2$CH$_2$CONHC$_6$H$_4$SO$_2$—, 1-naphthyl-SO$_2$—, and a sulfonyl group of formula (3)

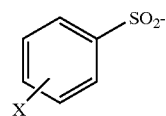

(3)

wherein R$_4$ is selected from the group consisting of 9-fluorenylmethoxycarbonyl, tert-butoxycarbonyl, benzyloxycarbonyl, C$_6$H$_5$OCH$_2$CO—, C$_6$H$_5$SCH$_2$CO—, 4-NO$_2$C$_6$H$_4$CHCHCO—, 9-fluorene-CH$_2$CO—, 9-fluorene-CO—, C$_6$H$_5$CH$_2$CH$_2$CO—, 3-NH$_2$C$_6$H$_4$CH$_2$CH$_2$CO—, 4-CH$_3$OC$_6$H$_4$CH$_2$CH$_2$CO—, 3-CH$_3$OC$_6$H$_4$CH$_2$CH$_2$CO—, 2-CH$_3$OC$_6$H$_4$CH$_2$CH$_2$CO—, 3,4-(CH$_3$O)$_2$C$_6$H$_3$CH$_2$CH$_2$CO—, 2,3-(CH$_3$O)$_2$C$_6$H$_3$CH$_2$CH$_2$CO—, 2,4-(CH$_3$O)$_2$C$_6$H$_3$CH$_2$CH$_2$CO—, 2,5-(CH$_3$O)$_2$C$_6$H$_3$CH$_2$CH$_2$CO—, 3,5-(CH$_3$O)$_2$C$_6$H$_3$CH$_2$CH$_2$CO—, C$_6$H$_3$CH$_2$CH$_2$CO—, 2-CH$_3$OC$_6$H$_4$CHCHCO—, 3,5-(CH$_3$O)$_2$C$_6$H$_3$CHCHCO—, 2,5-(CH$_3$O)$_2$C$_6$H$_3$CHCHCO—, 2,4-(CH$_3$O)$_2$C$_6$H$_3$CHCHCO—, and 3,4-(CH$_3$O)$_2$C$_6$H$_3$CHCHCO—, wherein X, is selected from the group consisting of H, a straight or branched alkyl group of 1 to 6 carbon atoms, F, Cl, Br, I, —NO$_2$, and —NH$_2$ and wherein R$_5$ is selected from the group consisting of straight and branched alkyl groups of 1 to 6 carbon atoms and when Cx is —COOH pharmaceutically acceptable alkali metal salts thereof, and when R$_2$ R$_4$ or both R$_2$ and R$_4$ comprises an amino group, pharmaceutically acceptable ammonium salts thereof.

2. A compound of formula Ia as defined in claim 1 and the pharmaceutically acceptable salts thereof, wherein n is 3 or 4, the alkali metal salts being selected from the group consisting of K, Na and Cs salts.

3. A compound of formula Ia as defined in claim 1 and the pharmaceutically acceptable salts thereof, wherein n is 4, the alkali metal salts being selected from the group consisting of K, Na and Cs salt.

4. A compound of formula Ia and the pharmaceutically acceptable salts thereof, as defined in claim 2, wherein R$_1$ is selected from the group consisting of isobutyl, cyclopropylmethyl and benzyl, and wherein Cx is selected from the group consisting of —COOH, and —CH$_2$OH.

5. A compound of formula Ia and the pharmaceutically acceptable salts thereof, as defined in claim 3, wherein R$_1$ is selected from the group consisting of isobutyl, cyclopropylmethyl and benzyl, and wherein Cx is selected from the group consisting of —COOH, and —CH$_2$OH.

6. A compound of formula Ia and the pharmaceutically acceptable salts thereof, as defined in claim 5 wherein X is selected from the group consisting of H, a straight or branched alkyl group of 1 to 6 carbon atoms, Br, NO$_2$, and NH$_2$, and wherein R$_4$ is selected from the group consisting of 9-fluorenylmethoxycarbonyl, 2,3-(CH$_3$O)$_2$C$_6$H$_3$CH$_2$CH$_2$CO—, 2,4-(CH$_3$O)$_2$C$_6$H$_3$CH$_2$CH$_2$CO—, C$_6$H$_5$SCH$_2$CO—, C$_6$H$_5$CH$_2$CO-, C$_6$H$_5$OCH$_2$CO—, 4-CH$_3$OC$_6$H$_4$CH$_2$CH$_2$CO—, 3-CH$_3$OC$_6$H$_4$CH$_2$CH$_2$CO—, 2-CH$_3$OC$_6$H$_4$CH$_2$CH$_2$CO—, and 3-NH$_2$C$_6$H$_4$CH$_2$CH$_2$CO—.

7. A compound of formula Ia and the pharmaceutically acceptable salts thereof, as defined in claim 6, wherein Cx is —COOH.

8. A compound of formula I

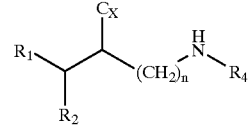

I wherein n is 1, 2, 3, 4 or 5 wherein Cx is selected from the group consisting of —COOH, —COOR$_5$, —CH$_2$OH, —CONHOH, wherein R$_1$ is selected from the group consisting of a straight or branched alkyl group of 1 to 6 carbon atoms, cyclopropylmethyl and benzyl, wherein R$_2$ is selected from the group consisting of 4-C$_6$H$_5$CH$_2$CH$_2$CONHC$_6$H$_4$SO$_2$—, 1-naphthyl-SO$_2$—, and a sulfonyl group of formula (3)

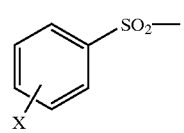

(3)

wherein R$_4$ is selected from the group consisting of 9-fluorenylmethoxycarbonyl, tert-butoxycarbonyl, benzyloxycarbonyl, C$_6$H$_5$OCH$_2$CO—, C₆H₅SCH₂CO—, 4-NO₂C₆H₄CHCHCO—, 9-fluorene-CH₂CO—, 9-fluorene-CO—, C₆H₅CH₂CH₂CO—, 3-NH₂C₆H₄CH₂CH₂CO—, 4-CH₃OC₆H₄CH₂CH₂CO—, 3-CH₃OC₆H₄CH₂CH₂CO—, 2-CH₃OC₆H₄CH₂CH₂CO—, 3,4-(CH₃O)₂C₆H₃CH₂CH₂CO—, 2,3-(CH₃O)₂C₆H₃CH₂CH₂CO—, 2,4-(CH₃O)₂C₆H₃CH₂CH₂CO—, 2,5-(CH₃O)₂C₆H₃CH₂CH₂CO—, 3,5-(CH₃O)₂C₆H₃CH₂CH₂CO—, 2-CH₃OC₆H₄CHCHCO—, 3,5-(CH₃O)₂C₆H₃CHCHCO—, 2,5-(CH₃O)₂C₆H₃CHCHCO—, 2,4-(CH₃O)₂C₆H₃CHCHCO—, 3,4-(CH₃O)₂C₆H₃CHCHCO—, and C₆H₄CH₂CH₂C=N—CN wherein X, is selected from the group consisting of H, a straight or branched alkyl group of 1 to 6 carbon atoms, F, Cl, Br, I, —NO₂, and —NH₂ and wherein $R_5$ is selected from the group consisting of straight and branched alkyl groups of 1 to 6 carbon atoms and when Cx is —COOH pharmaceutically acceptable alkali metal salts thereof, and when $R_2$, $R_4$ or both $R_2$ and $R_4$ comprises an amino group, pharmaceutically acceptable ammonium salts thereof.

9. A compound of formula

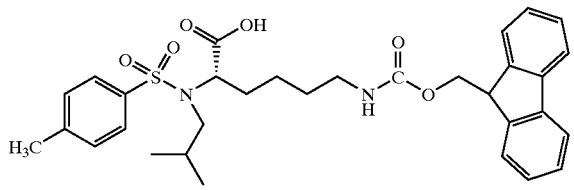

and K, Na and Cs salts thereof.

10. A compound of formula

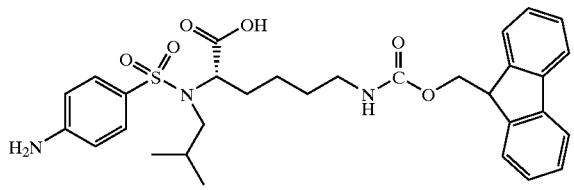

pharmaceutically acceptable ammonium salts thereof and K, Na and Cs salts thereof.

11. A compound of formula

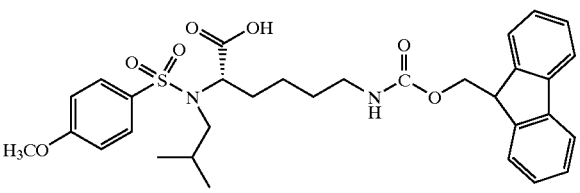

and K, Na and Cs salts thereof.

12. A compound of formula

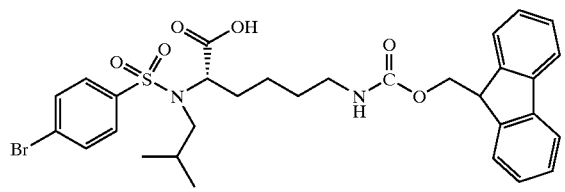

and K, Na and Cs salts thereof.

13. A compound of formula

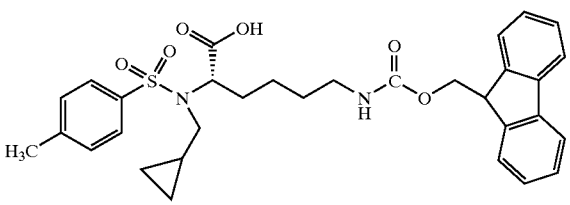

and K, Na and Cs salts thereof.

14. A compound of formula

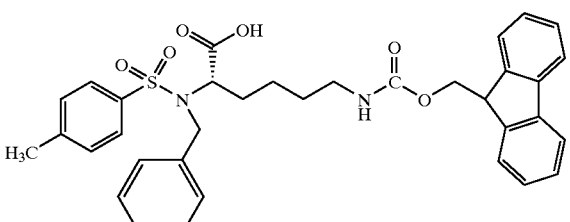

and K, Na and Cs salts thereof.

15. A compound of formula

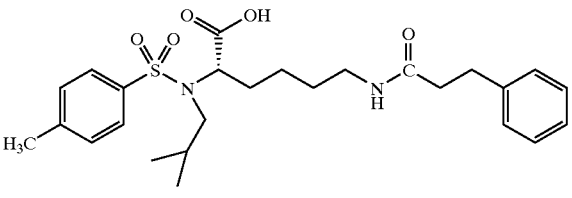

and K, Na and Cs salts thereof.

16. A compound of formula

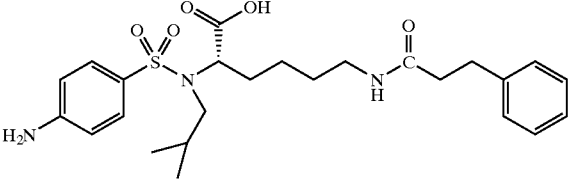

pharmaceutically acceptable ammonium salts thereof and K, Na and Cs salts thereof.

17. A compound of formula

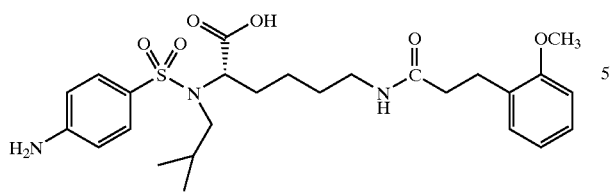

pharmaceutically acceptable ammonium salts thereof and K, Na or Cs salts thereof.

18. A compound of formula

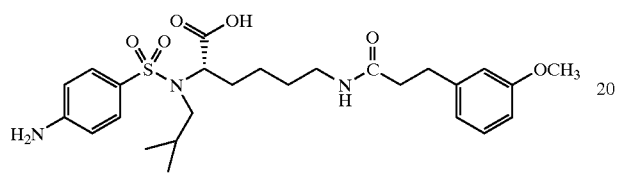

pharmaceutically acceptable ammonium salts thereof and K, Na and Cs salts thereof.

19. A compound of formula

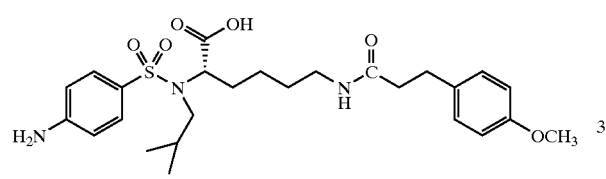

pharmaceutically acceptable ammonium salts thereof and K, Na and Cs salts thereof.

20. A compound of formula

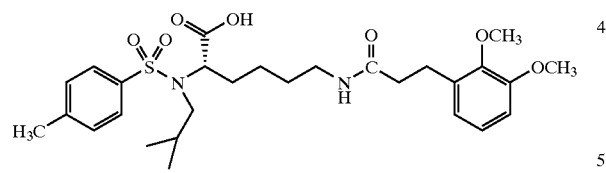

and K, Na and Cs salts thereof.

21. A compound of formula

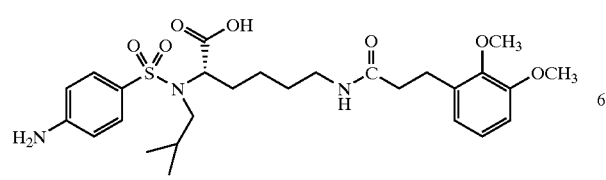

pharmaceutically acceptable ammonium salts thereof and K, Na and Cs salts thereof.

22. A compound of formula

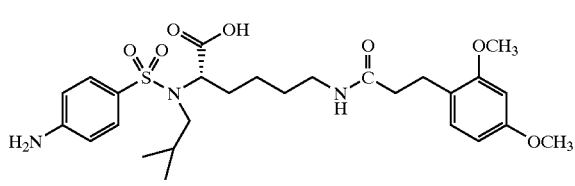

pharmaceutically acceptable ammonium salts thereof and K, Na and Cs salts thereof.

23. A compound of formula

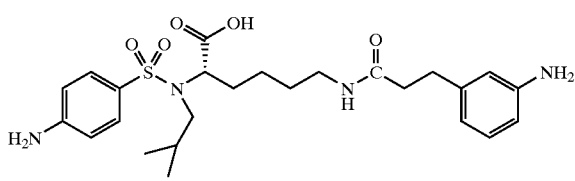

pharmaceutically acceptable ammonium salts thereof and K, Na and Cs salts thereof.

24. A compound of formula

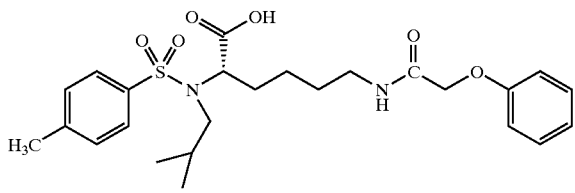

and K, Na and Cs salts thereof.

25. A compound of formula

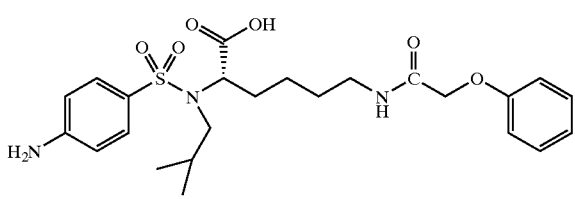

pharmaceutically acceptable ammonium salts thereof and K, Na and Cs salts thereof.

26. A compound of formula
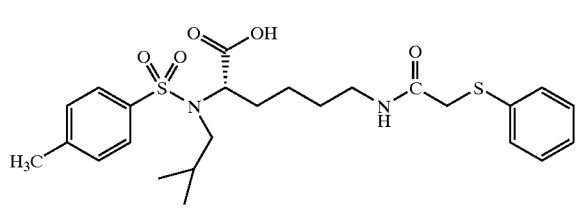
and K, Na and Cs salts thereof.
27. A compound of formula
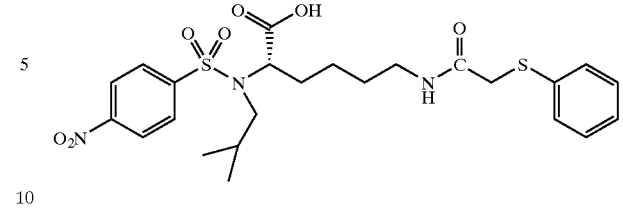
and K, Na and Cs salts thereof.
* * * * *